(12) United States Patent
Lubisch et al.

(10) Patent No.: US 7,951,807 B2
(45) Date of Patent: May 31, 2011

(54) SUBSTITUTED OXINDOL DERIVATIVES AND MEDICAMENTS CONTAINING THE SAME

(75) Inventors: Wilfried Lubisch, Heidelberg (DE); Thorsten Oost, Heidelberg (DE); Wolfgang Wernet, Neustadt (DE); Liliane Unger, Ludwigshafen (DE); Wilfried Hornberger, Neustadt (DE); Herve Geneste, Neuhofen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 406 days.

(21) Appl. No.: 11/632,462

(22) PCT Filed: Jul. 13, 2005

(86) PCT No.: PCT/EP2005/007631
§ 371 (c)(1),
(2), (4) Date: May 12, 2008

(87) PCT Pub. No.: WO2006/005609
PCT Pub. Date: Jan. 19, 2006

(65) Prior Publication Data
US 2009/0005397 A1 Jan. 1, 2009

Related U.S. Application Data

(60) Provisional application No. 60/587,407, filed on Jul. 13, 2004.

(30) Foreign Application Priority Data
Jul. 13, 2004 (DE) .......................... 10 2004 033 834

(51) Int. Cl.
A61K 31/404 (2006.01)
A61K 31/454 (2006.01)
C07D 209/34 (2006.01)
C07D 401/12 (2006.01)

(52) U.S. Cl. ..................... 514/253.09; 544/364; 544/61; 544/121; 544/129; 544/144; 544/373; 540/575; 540/597; 540/598; 540/602; 546/187; 546/194; 546/201; 546/256; 546/277.7

(58) Field of Classification Search .......................... None
See application file for complete search history.

(56) References Cited

U.S. PATENT DOCUMENTS
5,594,023 A 1/1997 Wagnon et al.

FOREIGN PATENT DOCUMENTS
WO WO 03/008407 A2 1/2003

OTHER PUBLICATIONS

Banker et al. "Modern Pharmaceutics", 3rd Ed. p. 596 (1996).*
Wolff, Manfred E. Burger's Medicinal Chemistry, 5th Ed. Part 1, pp. 975-977 (1995).*
Thibonnier, Exp.OPin.Invest.Drugs, vol. 7(5), p. 729-740 (1998).*
Hays, New England Journal of Medicine, vol. 355(20), p. 2146-2148 (2006).*
International Search Report in W02006/005609A2 mailed on Jan. 17, 2006.
Griebel, et al., Anxiolytic- and antidepressant-like effects of the non-peptide vasopressin V1b receptor antagonist, SSR149415, suggest an innovative approach for the treatment of stress-related disorders, www.pnas.org, Apr. 30, 2002, pp. 6370-6375, vol. 99, No. 9.
Griebel, et al., The Vasopressin V1b Receptor as a Therapeutic Target in Stress-related Disorders, Current Drug Targets-CNS & Neurological Disorders, 2003, 2, pp. 191-200.
Arnaldi, et al, Vasopressin Receptors Modulate the Pharmacological Phenotypes of Cushing's Syndrome, Endocrine Research, 1998, 24, pp. 807-816.
Wersinger, et al., Vasopressin V1b receptor knockout reduces aggressive behavior in male mice, Molecular Psychiatry, 2002, 7, pp. 975-984.
Umegaki, et al., Plasma cortisol levels in elderly female subjects with Alzheimer's disease: a cross-sectional and longitudinal study, Brain Research, 2000, 881, pp. 241-243.
Bielsky, Profound Impairment in Social Recognition and Reduction in Anxiety-Like Behavior in Vasopressin V I a Receptor Knockout Mice, Neuropsychopharmacology, 2004, 29, pp. 483-493.
Alonso, et al., Blockade of CRF1 or Vlb receptors reverses stress-induced suppression of neurogenesis in a mouse model of depression, Molecular Psychiatry, 2004, 9, pp. 278-286.
Wersinger, et al., Social motivation is reduced in vasopressin 1b receptor null mice despite normal performance in an olfactory discrimination task, Hormones and Behavior, 2004, 46, pp. 638-645.
Ward, et al., DDAVP in Treatment of Vasopressin-sensitive Diabetes Insipidus, British Medical Journal, 1974, 3, pp. 86-89.
Derick, et al., [1-Deamino-4-Cyclohexylalanine] Arginine Vasopressin: A Potent and Specific Agonist for Vasopressin V1b Receptors, Endocrinology, 143(12), pp. 4655-4664, (2002).
Zhou, et al., Drug-induced and genetic alterations in stress-responsive systems: Implications for specific addictive diseases, Brain Research, 2010, 1314, pp. 235-252.
Koob, A Role for Brain Stress Systems in Addiction, Neuron Review, Jul. 10, 2008, 59, pp. 11-34.
Zhou, et al., Involvement of Arginine Vasopressin and V I b Receptor in Heroin Withdrawal and Heroin Seeking Precipitated by Stress and by Heroin, Neuropsychopharmacology, 2008, 33, pp. 226-236.
Buyukcoskun, et al., Role of Intracerebroventricular Vasopressin in the Development of Sress-Induced Gastric Lesions in Rats, Physiological Research, 1999, 48, pp. 451-455.

(Continued)

Primary Examiner — Emily Bernhardt
(74) Attorney, Agent, or Firm — Lisa V. Mueller; Polsinelli Shughart PC

(57) ABSTRACT

The present invention relates to novel oxindole derivatives of the general formula (I),

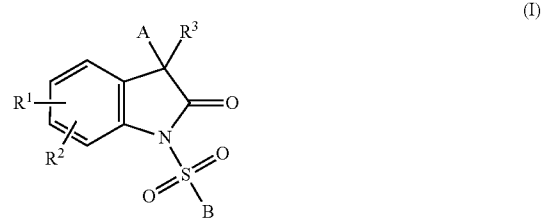

wherein the substituents A, B, $R^1$, $R^2$ and $R^3$ are as defined in Claim 1, and medicaments containing the same for the prophylaxis and/or treatment of vasopressin-dependent or oxytocin-dependent diseases.

7 Claims, No Drawings

OTHER PUBLICATIONS

Honda, et al., Role of endogenous vasopressin in development of gastric ulcer induced by restraint and water immersion, Division of Endocrinology and Metabolism, Department of Medicine, Jichi Medical School, Kawachi-gun, Tochigi, 329-04, Japan, p. R1448-R1453, (1994).

Kalamatianos, et al., Ageing and the Diurnal Expression of the mRNAs for Vasopressin and for the V1a and V1b Vasopressin Receptors in the Suprachiasmatic Nucleus of Male Rats, Journal of Neuroendocrinology, 2004, vol. 16, pp. 493-501.

Saito, et al., 1-Desamino-8-D-Arginine Vasopressin (DDAVP) as an Agonist on V1b Vasopressin Receptor, Biochemical Pharmacology, vol. 53, 1997, pp. 1711-1717.

Saito, et al., Evidence that atypical vasopressin V2 receptor in inner medulla of kidney is V1B receptor, European Journal of Pharmacology, 401, 2000, pp. 289-296.

Itoh, et al., Attenuated stress-induced catecholamine release in mice lacking the vasopressin V1b receptor, Am J Physiol Endocrinol Metab 291: E147-E151, 2006.

Steiger A. Sleep and the hypothalamo-pituitary-adrenocortical system. Sleep Med. Rev. 2002;6(2):125-38. Abstract Only.

Monstein HJ et al. Vasopressin receptor mRNA expression in the human gastrointestinal tract. Eur Surg Res 2008;40(1):34-40. Abstract Only.

* cited by examiner

SUBSTITUTED OXINDOL DERIVATIVES AND MEDICAMENTS CONTAINING THE SAME

CROSS-REFERENCE TO RELATED APPLICATIONS

This application is a §371 National Stage application of international application no. PCT/EP2005/007631, filed Jul. 13, 2005, which claims priority of German application no. 10 2004 033 834.5 filed Jul. 13, 2004 and U.S. Provisional application No. 60/587,407 filed Jul. 13, 2004, the contents of which are incorporated herein by reference.

The present invention relates to novel oxindole derivatives and medicaments containing the same for the treatment of diseases.

Vasopressin is an endogenous hormone that has a very wide range of effects on organs and tissue. It is suspected that the vasopressin system plays a role in various health conditions, such as cardiac insufficiency and high blood pressure. Currently, three receptors (V1a, V1b or V3 and V2) are known, by means of which vasopressin imparts its numerous effects. For this reason, antagonists of these receptors are being examined as possible new therapeutic approaches for the treatment of diseases (M. Thibonnier, Exp. Opin. Invest. Drugs 1998, 7(5), 729-740).

In the application under consideration, novel substituted oxindoles are described that carry an arylsulfonyl group in the 1-position. 1-phenyl-sulfonyl-1,3-dihydro-2H-indole-2-ones have already been described as ligands of the vasopressin receptors. In WO 93/15051, WO95/18105, WO 98/25901, WO 01/55130, WO 01/55134, WO 01/164668 and WO 1/98295, derivatives have been described that are derived from the oxindole skeleton and that carry arylsulfonyl groups in the 1-position. These compounds essentially differ in the substitution in the 3-position.

In particular, in WO 93/15051 and WO 98/25901, 1-phenyl-sulfonyl-1,3-dihydro-2H-indole-2-ones are described as ligands of the vasopressin receptors in which two alkyl radicals, which likewise can be a cycloalkyl radical (spiro union), substitute for the oxindole skeleton in the 3-position. As alternatives, the spiro ing can contain heteroatoms, such as oxygen and nitrogen (optionally with substituents).

WO 95/18105 describes 1-phenylsulfonyl-1,3-dihydro-2H-indole-2-ones as ligands of the vasopressin receptors that have a nitrogen atom in the 3-position. In addition, radicals, which can be alkyl, cycloalkyl, phenyl or benzyl radicals (each optionally with substituents), are bound in the 3-position.

Other publications, such as WO 01/55130, describe compounds that have nitrogen-containing rings (e.g., proline, homoproline, morpholine, tetrahydroisoquinoline or dihydroindole, each optionally with substituents) that are bound to the 3-position of the oxindole skeleton via their nitrogen atom, but that are substituted with phenylsulfonyl or phenyl groups (optionally with substituents) in both the 1-position and the 3-position on the oxindole ring.

In WO 03/008407, 1-phenylsulfonyl-oxindoles are described in which pyridylpiperazines are bound to the oxindole in the 3-position via an oxycarbonyl group and analogous functional groups.

The object of the present invention is to provide additional compounds for the treatment or prophylaxis of various vasopressin-dependent or oxytocin-dependent diseases, wherein these compounds display a high level of selective activity.

The object is solved by a compound or compounds having the general formula (I),

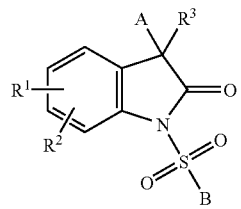

(I)

where

A is $C_{6-10}$ aryl that can be substituted with a maximum of four residues $R^4$ that are selected independently of one another from the group consisting of hydrogen, chlorine, bromine, iodine, fluorine, $(CH_2)_{0-2}$—CN, $CF_3$, $OCF_3$, $CONH_2$, $CONH(C_1$-$C_4$ alkyl), $CON(C_1$-$C_4$ alkyl)($C_1$-$C_4$ alkyl), NHCHO, $NHCONH_2$, $N(C_0$-$C_4$ alkylene)$CONH_2$, $N(C_0$-$C_4$ alkylene) $CONH(C_1$-$C_4$ alkyl), $NHCOCH_3$, $NO_2$, $(CH_2)_{0-2}$—OH, O—$C_1$-$C_6$ alkyl, $(CH_2)_{0-2}$—O—$C_1$-$C_4$ alkyl, O—$C_0$-$C_4$ alkylene-phenyl, phenyl, $C_1$-$C_6$ alkyl, $C_2$-$C_6$ alkenyl and $C_2$-$C_6$ alkynyl, B is an aromatic or partly aromatic monocyclic or bicyclic $C_{6-10}$ that can be substituted with the residues $R^6$, $R^7$, $R^8$ and/or $R^9$, wherein $R^6$, $R^7$, $R^8$ and $R^9$ are selected independently of one another from the group consisting of hydrogen, chlorine, bromine, iodine, fluorine, $(CH_2)_{0-2}$—CN, $CF_3$, $OCF_3$, $CONH_2$, $CONH(C_1$-$C_4$ alkyl), $CON(C_1$-$C_4$ alkyl)($C_1$-$C_4$ alkyl), NHCHO, $N(C_{0-4}$ alkylene)$CONH(C_1$-$C_4$ alkyl), $NHCOCH_3$, $NO_2$, OH, O—$C_1$-$C_4$ alkyl, $(CH_2)_{0-2}$—O—$(CH_2)_{0-3}$—$CH_3$, O—$C_0$-$C_4$ alkylene-phenyl, phenyl, $C_1$-$C_6$ alkyl, $C_2$-$C_6$ alkenyl and $C_2$-$C_6$ alkynyl, $R^1$ is hydrogen, $C_1$-$C_6$ alkyl, OH, O—($C_1$-$C_4$ alkyl), N($C_1$-$C_4$ alkyl)($C_1$-$C_4$ alkyl), CN, $CONH_2$, $OCF_3$, $CF_3$, Br, F, Cl, J, $NO_2$, NHCHO, NHCO($C_1$-$C_4$ alkyl) or $NHCONH_2$, $R^2$ is hydrogen, $C_1$-$C_4$ alkyl, O—($C_1$-$C_4$ alkyl), Cl or F, $R^3$ is a residue (W)—(X)—(Y)—Z, wherein W is $C_1$-$C_4$ alkylene, ($C_0$-$C_4$ alkylene)-O—($C_0$-$C_4$ alkylene) or ($C_0$-$C_4$ alkylene)-$NR^{15}$—($C_0$-$C_4$ alkylene), wherein $R^{15}$ is hydrogen or $C_1$-$C_4$ alkyl, X is CO, $SO_2$, (C═NH) or (C═N—CN) and Y is a residue selected from the group consisting of

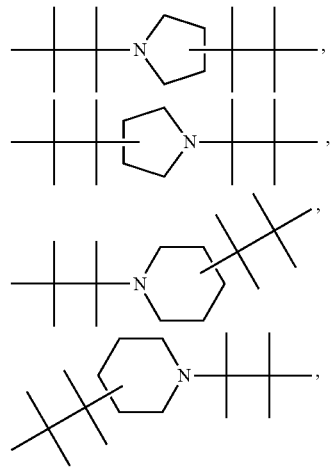

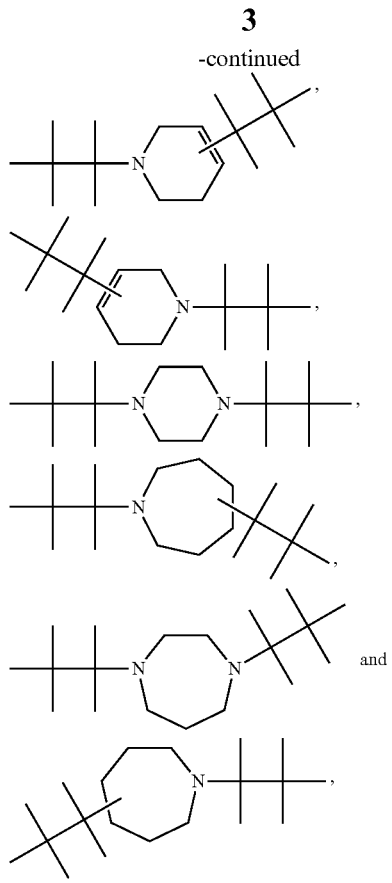

wherein Y can additionally be substituted with $R^{10}$ and/or $R^{11}$, and $R^{10}$ is hydrogen, $C_1$-$C_6$ alkyl, $C_2$-$C_6$ alkenyl, $C_2$-$C_6$ alkynyl, OH, O—$C_1$-$C_4$ alkyl, O—$C_0$-$C_4$ alkylene-phenyl, $NH_2$, $NH(C_1$-$C_4$ alkyl) or $N(C_1$-$C_4$ alkyl)($C_1$-$C_4$ alkyl), $R^{11}$ is hydrogen, $C_1$-$C_6$ alkyl, $C_2$-$C_6$ alkenyl, $C_2$-$C_6$ alkynyl, OH, O—$C_1$-$C_4$ alkyl, O—$C_0$-$C_4$ alkylene-phenyl, $NH_2$, $NH(C_1$-$C_4$ alkyl) or $N(C_1$-$C_4$ alkyl)($C_1$-$C_4$ alkyl), and Z is a residue selected from the group consisting of

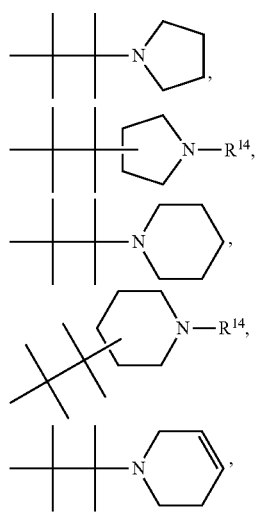

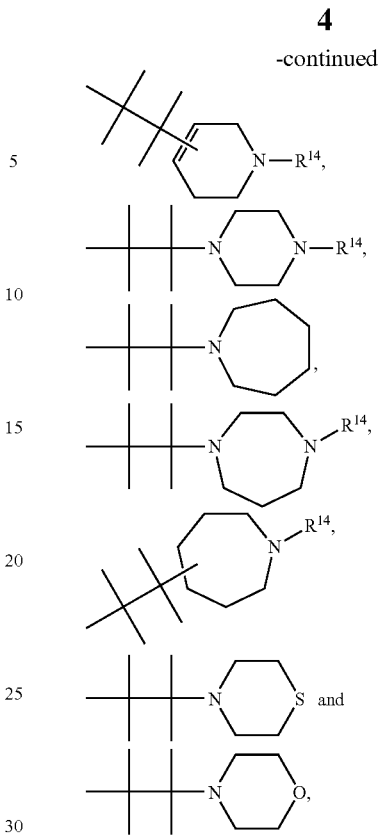

and Z can additionally be substituted with $R^{12}$ and/or $R^{13}$, wherein $R^{12}$ is hydrogen, $C_1$-$C_6$ alkyl, $C_2$-$C_6$ alkenyl, $C_2$-$C_6$ alkynyl, OH, O—$C_1$-$C_4$ alkyl, O—$C_0$-$C_4$ alkylene-phenyl, $NH_2$, $NH(C_1$-$C_4$ alkyl) or $N(C_1$-$C_4$ alkyl)($C_1$-$C_4$ alkyl), $R^{13}$ is hydrogen, $C_1$-$C_6$ alkyl, $C_2$-$C_6$ alkenyl, $C_2$-$C_6$ alkynyl, OH, O($C_1$-$C_4$ alkyl), O—$C_0$-$C_4$ alkylene-phenyl, $NH_2$, $NH(C_1$-$C_4$ alkyl) or $N(C_1$-$C_4$ alkyl)($C_1$-$C_4$ alkyl), $R^{14}$ is hydrogen, $C_1$-$C_6$ alkyl, $C_2$-$C_6$ alkenyl, $C_2$-$C_6$ alkynyl or $C_0$-$C_4$ alkylene-phenyl, and their tautomeric, enantiomeric and/or diastereomeric forms, and their prodrugs, as well as the physiologically compatible salts of the aforementioned compound or compounds.

In a preferred embodiment, in the compounds of the general formula (I), A is a phenyl ring that can be substituted with a maximum of four residues $R^4$, and B is a phenyl ring that can be substituted with the residues $R^6$, $R^7$, $R^8$ and/or $R^9$.

Furthermore, a compound or compounds with the general formula (I) are preferred wherein A is a phenyl ring that can be substituted with a maximum of two residues $R^4$, which are selected independently of one another from the group consisting of hydrogen, chlorine, O—$C_1$-$C_4$ alkyl, $(CH_2)_{0-2}$—O—$(CH_2)_{0-2}$—$CH_3$ and $C_1$-$C_6$ alkyl, B is a phenyl ring that can be substituted with the residues $R^6$, $R^7$, $R^8$ and/or $R^9$, wherein $R^6$, $R^7$, $R^8$ and $R^9$ are selected independently of one another from the group consisting of hydrogen, fluorine, chlorine, O—$C_1$-$C_4$ alkyl, $(CH_2)_{0-2}$—O—$(CH_2)_{0-2}$—$CH_3$ and $C_1$-$C_6$ alkyl, $R^1$ is hydrogen, CN, F, Cl, $C_{1-4}$ alkyl, OH or O—($C_{1-4}$ alkyl), $R^2$ is hydrogen, $R^3$ is a residue (W)—(X)—(Y)—Z, wherein W is O, $CH_2NH$, $NHCH_2$, $OCH_2$, $CH_2O$ or NH, X is CO, Y is a residue selected from the group consisting of

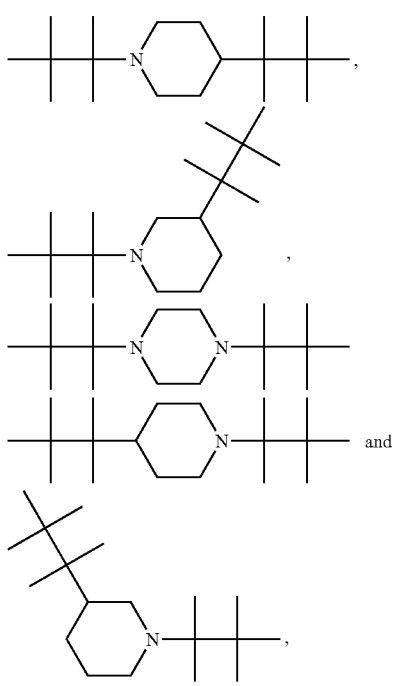

Z is a residue selected from the group consisting of

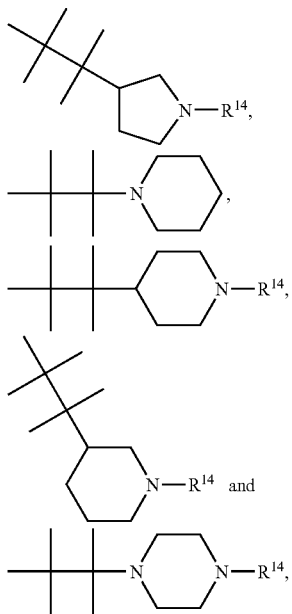

wherein Z can additionally be substituted with $R^{12}$ and/or $R^{13}$,
wherein
$R^{12}$ is hydrogen or $C_1$-$C_4$ alkyl,
$R^{13}$ is hydrogen or $C_1$-$C_4$ alkyl and
$R^{14}$ is hydrogen, $C_1$-$C_4$ alkyl, $C_2$-$C_4$ alkenyl or $C_2$-$C_4$ alkynyl.

Particularly preferred are a compound or compounds of the general formula (I), wherein
A is a phenyl ring that can be substituted with a maximum of two residues $R^4$ that are selected independently of one another from the group consisting of hydrogen, chlorine, O—$C_1$-$C_4$ alkyl, $(CH_2)_{0-2}$—O—$(CH_2)_{0-2}$—$CH_3$ and $C_1$-$C_6$ alkyl,
B is a phenyl ring that can be substituted with the residues $R^6$ and/or $R^7$, wherein $R^6$ and $R^7$ can be selected independently of one another from the group consisting of hydrogen, fluorine, chlorine, O—$C_1$-$C_4$ alkyl and $C_1$-$C_6$ alkyl,
$R^1$ is hydrogen, F, Cl, $CH_3$, CN, $CH_2CH_3$, $OCH_3$ or $OCH_2CH_3$,
$R^2$ is hydrogen,
$R^3$ is a residue (W)—(X)—(Y)—Z, wherein
  W is O, $CH_2$ or NH,
  X is CO,
  Y is a residue selected from the group

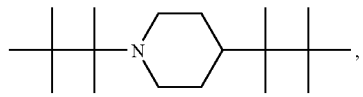

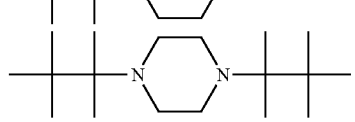

and
Z is a residue selected from the group

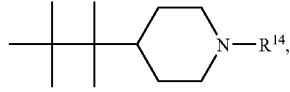

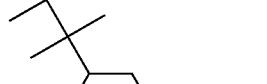

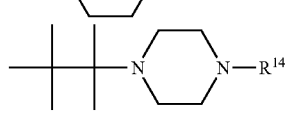

wherein Z can be substituted with $R^{12}$ and/or $R^{13}$, wherein
$R^{12}$ is hydrogen or $C_1$-$C_4$ alkyl,
$R^{13}$ is hydrogen or $C_1$-$C_4$ alkyl and
$R^{14}$ is hydrogen, $C_1$-$C_4$ alkyl, $C_2$-$C_4$ alkenyl or $C_2$-$C_4$ alkynyl.

Particularly preferred are furthermore compounds of the general formula (I), wherein
A is a phenyl ring that can be substituted with a maximum of two residues $R^4$ that are selected independently of one another from the group consisting of hydrogen, chlorine, O—$C_0$-$C_4$ alkyl, $(CH_2)_{0-2}$—O—$(CH_2)_{0-2}$—$CH_3$ and $C_1$-$C_6$ alkyl,
B is a phenyl ring that can be substituted with the residues $R^6$ and/or $R^7$, wherein $R^6$ and $R^7$ are selected independently of one another from the group consisting of hydrogen, fluorine, chlorine, O—$C_1$-$C_4$ alkyl and $C_1$-$C_6$ alkyl, $R^1$ is Cl, $CH_3$, CN, $CH_2CH_3$ or $OCH_3$,
$R^2$ is hydrogen,
$R^3$ is a residue (W)—(X)—(Y)—Z, wherein
W is $CH_2$, O or NH,
X is CO,
Y is a residue

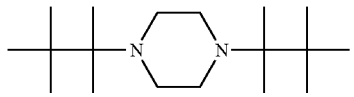

Z is a residue

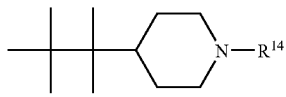

wherein
$R^{14}$ is hydrogen, $C_1$-$C_4$ alkyl, $C_2$-$C_4$ alkenyl or $C_2$-$C_4$ alkynyl.

Furthermore, a compound or compounds with the general formula (I) are particularly preferred wherein
A is a phenyl ring that can be substituted with a maximum of two residues $R^4$ that are selected independently of one another from the group consisting of hydrogen, chlorine, O—$C_1$-$C_4$ alkyl and $C_1$-$C_4$ alkyl,
B is a phenyl ring that is substituted with the residues $R^6$ and/or $R^7$, wherein $R^6$ and $R^7$ are selected independently of one another from the group consisting of hydrogen, fluorine, chlorine, O—$C_1$-$C_4$ alkyl and $C_1$-$C_6$ alkyl,
$R^1$ is hydrogen, Cl, $CH_3$, CN, $CH_2CH_3$, $OCH_3$ or $OCH_2CH_3$,
$R^2$ is hydrogen,
$R^3$ is a residue (W)—(X)—(Y)—Z, wherein
W is $CH_2$, O or NH,
X is CO,
Y is a residue

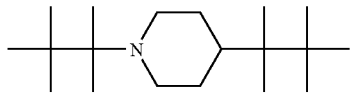

and
Z is a residue

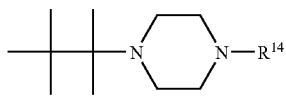

wherein
$R^{14}$ is hydrogen, $C_1$-$C_4$ alkyl, $C_2$-$C_4$ alkenyl or $C_1$-$C_4$ alkynyl.

The expression "maximum of four residues $R^4$" in connection with variable A means the presence of no, one, two, three or four substituents on A, wherein the residues $R^4$ can be the same or different.

The expression "maximum of two residues $R^4$" in connection with variable A means the presence of no, one or two substituents on A, wherein the residues $R^4$ can be the same or different.

The expression "$R^{10}$ and/or $R^{11}$" in connection with variable Y means one or two identical or different residues selected from the group consisting of $R^{10}$ and $R^{11}$.

The expression "$R^{12}$ and/or $R^{13}$" in connection with variable Z means one or two identical or different residues selected from the group consisting of $R^{12}$ and $R^{13}$.

The variables that identify the compounds of formula (I) according to the invention have the following preferred meanings, independently of one another.

A is preferably a phenyl ring that can be substituted with a maximum of four residues $R^4$, even more preferably a phenyl ring that can be substituted with a maximum of two residues $R^4$. In one embodiment, A is unsubstituted phenyl.

In another embodiment, A is substituted with a substituent. If A is substituted, the substituents $R^4$ are selected independently of one another from the group consisting of hydrogen, chlorine, bromine, iodine, fluorine, $(CH_2)_{0-2}$—CN, $CF_3$, $OCF_3$, $CONH_2$, $CONH(C_1$-$C_4$ alkyl), $CON(C_1$-$C_4$ alkyl)($C_1$-$C_4$ alkyl), NHCHO, $NHCONH_2$, $N(C_0$-$C_4$ alkylene)$CONH_2$, $N(C_0$-$C_4$ alkylene)$CONH(C_1$-$C_4$ alkyl), $NHCOCH_3$, $NO_2$, $(CH_2)_{0-2}$—OH, O—$C_1$-$C_6$ alkyl, $(CH_2)_{0-2}$—O—$C_1$-$C_4$ alkyl, O—$C_0$-$C_4$ alkylene-phenyl, phenyl, $C_1$-$C_6$ alkyl, $C_2$-$C_6$ alkenyl and $C_2$-$C_6$ alkynyl, preferably hydrogen, chlorine, O—$C_1$-$C_4$ alkyl, $(CH_2)_{0-2}$—O—$(CH_2)_{0-2}$—$CH_3$ and $C_1$-$C_6$ alkyl, even more preferably hydrogen, chlorine, O—$C_1$-$C_4$ alkyl and $C_1$-$C_4$ alkyl. If A is a phenyl ring, a substituent is preferably to be found in the 2-position, wherein other substituents can be in the 3-, 4- or 5-position, or even more preferably, a substituent is located in the 2-position and a further one is located in the 3-, 4- or 5-position, and most preferably a substituent is located in the 2-position.

B is preferably a phenyl ring that can be substituted with the residues $R^6$, $R^7$, $R^8$ and/or $R^9$. Preferably, B is substituted with no, one, two, three or four identical or different residues selected from $R^6$, $R^7$, $R^8$ and $R^9$. More preferably, B is a phenyl ring that can be substituted with the residues $R^6$ and/or $R^7$. In one embodiment, B is unsubstituted phenyl. In another embodiment, B is substituted with a substituent $R^6$. If B is substituted, the substituents $R^6$, $R^7$, $R^8$ and/or $R^9$ are selected independently of one another from the group consisting of hydrogen, chlorine, bromine, iodine, fluorine, $(CH_2)_{0-2}$—CN, $CF_3$, $OCF_3$, $CONH_2$, $CONH(C_1$-$C_4$ alkyl), $CON(C_0$-$C_4$ alkyl)($C_1$-$C_4$ alkyl), NHCHO, $N(C_{0-4}$ alkylene)$CONH(C_1$-$C_4$ alkyl), $NHCOCH_3$, $NO_2$, OH, O—$C_1$-$C_4$ alkyl, $(CH_2)_{0-2}$—O—$(CH_2)_{0-3}$—$CH_3$, O—$C_0$-$C_4$ alkylene-phenyl, phenyl, $C_1$-$C_6$ alkyl, $C_2$-$C_6$ alkenyl and $C_2$-$C_6$ alkynyl, preferably hydrogen, fluorine, chlorine, O—$C_1$-$C_4$ alkyl, $(CH_2)_{0-2}$—O—$(CH_2)_{0-2}$—$CH_3$ and $C_1$-$C_6$ alkyl, and even more preferably hydrogen, fluorine, chlorine, O—$C_1$-$C_4$ alkyl and $C_1$-$C_6$ alkyl. If B is a phenyl ring, the substituents are preferably located in the 2-, 3-, 4-, 5- and/or 6-position, preferably there are a maximum of 4 substituents, of which two substituents are in the 2- and 4-positions or one substituent is either in the 2- or 4-position, and even more preferably, two substituents are in the 2- and 4-positions or one substituent is either in the 2- or 4-position.

$R^1$ is preferably hydrogen, CN, F, Cl, $C_{1-4}$ alkyl or O—($C_{1-4}$ alkyl), even more preferably hydrogen, F, Cl, $CH_3$, CN, $CH_2CH_3$, $OCH_3$ or $OCH_2CH_3$, and most preferably Cl, $CH_3$, CN, $CH_2CH_3$ or $OCH_3$. $R^1$ is preferably located in the 4-, 5- or 6-position, even more preferably in the 4- or 5-position, and most preferably in the 5-position.

$R^2$ is preferably hydrogen.

$R^3$ is a residue (W)—(X)—(Y)—Z, wherein preferred definitions of $R^3$ result from the definitions of W, X, Y and Z, in which at least one of the definitions of W, X, Y and Z represents any preferred embodiment, as explained in the following. Preferably, all definitions of W, X, Y and Z represent any preferred embodiment. Most preferably, $R^3$ is a residue (W)—(X)—(Y)—Z, wherein all definitions of W, X, Y and Z represent the most preferred embodiment in each case.

W is preferably O, ($C_1$-$C_4$ alkylene)NH, NH($C_1$-$C_4$ alkylene), O($C_1$-$C_4$ alkylene), ($C_1$-$C_4$ alkylene)O or NH, even more preferably O, $CH_2NH$, $NHCH_2$, $OCH_2$, $CH_2O$ or NH, and most preferably $CH_2$, O or NH.

X is preferably CO or $SO_2$, most preferably CO.

Y is preferably

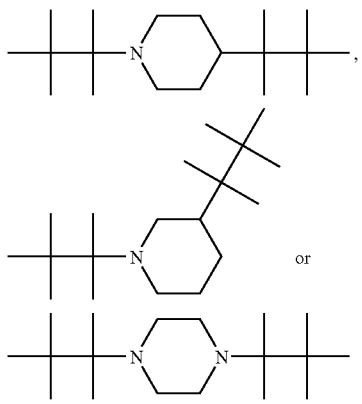

and most preferably

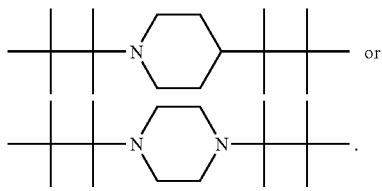

$R^{10}$ is preferably hydrogen or $C_1$-$C_4$ alkyl, wherein the alkyl group can be in the 2-, 3-, 5- or 6-position, preferably hydrogen or a $C_1$-$C_4$ alkyl group that is in the 2-position and especially preferably hydrogen.

$R^{11}$ is preferably hydrogen or $C_1$-$C_4$ alkyl, wherein the alkyl group can be in the 2-, 3-, 5- or 6-position, preferably hydrogen or a $C_1$-$C_4$ alkyl group that is in the 2-position and especially preferably hydrogen.

Z is preferably

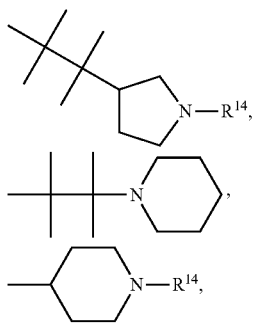

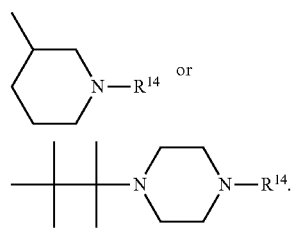

Even more preferably, Z is

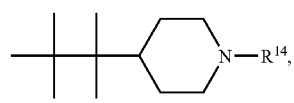

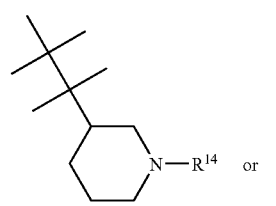

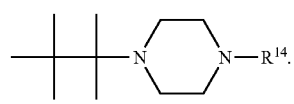

In one embodiment, Z is

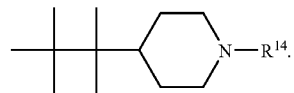

In another embodiment, Z is

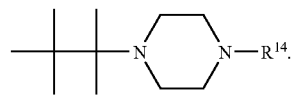

$R^{12}$ is preferably hydrogen or $C_1$-$C_4$ alkyl, wherein the alkyl group can be in the 2-, 3-, 4- or 6-position, preferably hydrogen or a $C_1$-$C_4$ alkyl group that is in the 2-position and especially preferably hydrogen.

$R^{13}$ is preferably hydrogen or $C_1$-$C_4$ alkyl, wherein the alkyl group can be in the 2-, 3-, 4- or 6-position, preferably hydrogen or a $C_1$-$C_4$ alkyl group that is in the 2-position and especially preferably hydrogen.

$R^{14}$ is preferably hydrogen, $C_1$-$C_4$ alkyl, $C_2$-$C_4$ alkenyl or $C_2$-$C_4$ alkynyl, even more preferably hydrogen, $CH_3$, $CH_2CH_3$, $CH_2CH_2CH_3$ or $CH(CH_3)_2$, most preferably $CH_3$.

$R^{15}$ is preferably hydrogen or $C_1$-$C_4$ alkyl, preferably hydrogen, $CH_3$, $CH_2CH_3$ or $CH_2CH_2CH_3$, and most preferably hydrogen or $CH_3$.

This results in the following especially preferred groups for R³:

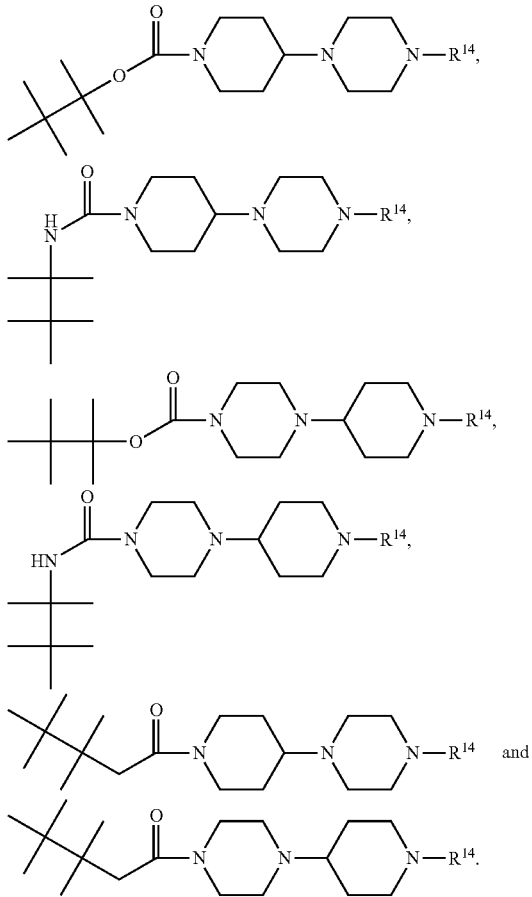

Each of these preferred definitions of a variable can be combined with any definitions of the other variables.

Likewise especially preferred are the following compounds:

4-(4-Methyl-piperidine-1-yl)-piperazine-1-carboxylic acid-[1-benzenesulfonyl-5-chloro-2-oxo-3-(2-methoxy-phenyl)-2,3-dihydro-1H-indole-3-yl] ester 4-(1-Methyl-piperidine-4-yl)-piperazine-1-carboxylic acid-[1-(2,4-dimethoxy-benzenesulfonyl)-5-methoxy-2-oxo-3-(2-propoxyphenyl)-2,3-dihydro-1H-indole-3-yl] ester 4-(1-Methyl-piperidine-4-yl)-piperazine-1-carboxylic acid-[1-(2,4-dimethoxy-benzenesulfonyl)-5-chloro-2-oxo-3-(2-methoxyphenyl)-2,3-dihydro-1H-indole-3-yl] amide dihydrochloride 4-(1-Methyl-piperidine-4-yl)-piperazine-1-carboxylic acid-[1-benzenesulfonyl-5-chloro-2-oxo-3-phenyl-2,3-dihydro-1H-indole-3-yl-ester]-dihydrochloride 4-(4-Methyl-piperazine-1-yl)-piperidine-1-carboxylic acid-[1-benzenesulfonyl-5-chloro-2-oxo-3-phenyl-2,3-dihydro-1H-indole-3-yl] ester 4-(1-Methyl-piperidine-4-yl)-piperazine-1-carboxylic acid-[1-(2,4-dimethoxy-benzenesulfonyl)-5-methoxy-2-oxo-3-(2-methoxyphenyl)-2,3-dihydro-1H-indole-3-yl] ester 4-(4-Methyl-piperazine-1-yl)-piperidine-1-carboxylic acid-[1-benzenesulfonyl-5-methyl-2-oxo-3-phenyl-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2-methylphenyl)-2,3-dihydro-1H-indole-3-yl] ester dihydrochloride 4-(Piperidine-4-yl)-piperazine-1-carboxylic acid-[1-(2,4-dimethoxy-benzenesulfonyl)-5-methoxy-2-oxo-3-(2-methoxyphenyl)-2,3-dihydro-1H-indole-3-yl] ester 4-(1-Methyl-piperidine-4-yl)-piperazine-1-carboxylic acid-[1-(2,4-dimethoxy-benzenesulfonyl)-5-fluoro-2-oxo-3-(2-methoxyphenyl)-2,3-dihydro-1H-indole-3-yl] ester 4-(1-Methyl-piperidine-4-yl)-piperazine-1-carboxylic acid-[1-(2-cyano-benzenesulfonyl)-5-methoxy-2-oxo-3-(2-methylphenyl)-2,3-dihydro-1H-indole-3-yl] ester dihydrochloride 4-(1-Methyl-piperidine-4-yl)-piperazine-1-carboxylic acid-[1-(4-bromo-2-methyl-benzenesulfonyl)-5-methoxy-2-oxo-3-(2-methylphenyl)-2,3-dihydro-1H-indole-3-yl] ester dihydrochloride 4-(1-Benzyl-piperidine-4-yl)-piperazine-1-carboxylic acid-[1-(2,4-dimethoxy-benzenesulfonyl)-5-methoxy-2-oxo-3-(2-methoxyphenyl)-2,3-dihydro-1H-indole-3-yl] ester 4-(1-Methyl-piperidine-4-yl)-piperazine-1-carboxylic acid-[1-(2,4-dimethoxy-benzenesulfonyl)-5-methyl-2-oxo-3-(2-methylphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-cyano-2-oxo-3-(2-methylphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2-methoxyphenyl)-2,3-dihydro-1H-indole-3-yl] amide dihydrochloride 4-(1-Methyl-piperidine-4-yl)-piperazine-1-carboxylic acid-[1-(2,4-dimethoxy-benzenesulfonyl)-5-Methyl-2-oxo-3-(2-methoxyphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2-isopropylphenyl)-2,3-dihydro-1H-indole-3-yl] ester dihydrochloride 4-(1-Methyl-piperidine-4-yl)-piperazine-1-carboxylic acid-[1-(4-methoxy-benzenesulfonyl)-5-methoxy-2-oxo-3-(2-isopropylphenyl)-2,3-dihydro-1H-indole-3-yl] ester dihydrochloride 4-(1-Methyl-piperidine-4-yl)-piperazine-1-carboxylic acid-[1-(3,4-dimethoxy-benzenesulfonyl)-5-methoxy-2-oxo-3-(2-isopropylphenyl)-2,3-dihydro-1H-indole-3-yl] ester dihydrochloride 4-(1-Methyl-piperidine-4-yl)-piperazine-1-carboxylic acid-[1-(4-isopropyl-benzenesulfonyl)-5-methoxy-2-oxo-3-(2-isopropylphenyl)-2,3-dihydro-1H-indole-3-yl] ester dihydrochloride 4-(1-Methyl-piperidine-4-yl)-piperazine-1-carboxylic acid-[1-(2-cyano-benzenesulfonyl)-5-methoxy-2-oxo-3-(2-isopropylphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-2-oxo-3-(2-methoxyphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2-isopropoxyphenyl)-2,3-dihydro-1H-indole-3-yl] ester dihydrochloride 4-(1-Methyl-piperidine-4-yl)-piperazine-1-carboxylic acid-[1-(2-cyano-benzenesulfonyl)-5-methoxy-2-oxo-3-(2-isopropoxyphenyl)-2,3-dihydro-1H-indole-3-yl] ester dihydrochloride 4-(1-Methyl-piperidine-4-yl)-piperazine-1-carboxylic acid-[1-(2-methoxy-4-methyl-benzene)-sulfonyl-5-methoxy-2-oxo-3-(2-isopropoxyphenyl)-2,3-dihydro-1H-indole-3-yl] ester dihydrochloride 4-(1-Methyl-piperidine-4-yl)-piperazine-1-carboxylic acid-[1-(2-methyl-benzenesulfonyl)-5-methoxy-2-oxo-3-(2-isopropylphenyl)-2,3-dihydro-1H-indole-3-yl] ester dihydrochloride 4-(1-Methyl-piperidine-4-yl)-piperazine-1-carboxylic acid-[1-(2-methyl-benzenesulfonyl)-5-methoxy-2-oxo-3-(2-isopropoxyphenyl)-2,3-dihydro-1H-indole-3-yl] ester dihydrochloride 4-(1-Methyl-piperidine-4-yl)-piperazine-1-carboxylic acid-[1-(2-methyl-benzenesulfonyl)-5-methoxy-2-oxo-3-(2-ethoxyphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2-ethoxyphenyl)-2,3-dihydro-1H-indole-3-yl] ester dihydrochloride 4-(1-Methyl-piperidine-4-yl)-piperazine-1-carboxylic acid-[1-(2-methyl-benzenesulfonyl)-5-methoxy-2-oxo-3-(2-methoxyphenyl)-2,3-dihydro-1H-indole-3-yl] ester dihydrochloride 4-(1-Methyl-piperidine-4-yl)-piperazine-1-carboxylic acid-[1-(3-cyano-benzenesulfonyl)-5-methoxy-2-oxo-3-(2-ethoxyphenyl)-2,3-dihydro-1H-indole-3-yl] ester dihydrochloride 4-(1-Methyl-piperidine-4-yl)-piperazine-1-carboxylic acid-[1-(4-ethyl-benzenesulfonyl)-5-methoxy-2-oxo-3-(2-ethoxyphenyl)-2,3-dihydro-1H-indole-3-yl] ester dihydrochloride 4-(1-Methyl-piperidine-4-yl)-piperazine-1-carboxylic acid-[1-(2-methyl-benzenesulfonyl)-5-methoxy-2-oxo-3-(2-propoxyphenyl)-2,3-dihydro-1H-indole-3-yl] ester dihydrochloride 4-(1-Methyl-piperidine-4-yl)-piperazine-1-carboxylic acid-[1-(2-methoxy-4-methyl-benzenesulfonyl)-5-methoxy-2-oxo-3-(2-propoxyphenyl)-2,3-dihydro-1H-indole-3-yl] ester dihydrochloride 4-(1-Methyl-piperidine-4-yl)-piperazine-1-carboxylic acid-[1-benzenesulfonyl-5-methyl-2-oxo-3-phenyl-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2-ethylphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2,5-dimethoxyphenyl)-2,3-dihydro-1H-indole-3-yl] ester dihydrochloride 4-(1-Methyl-piperidine-4-yl)-piperazine-1-carboxylic acid-[1-(2-methyl-benzenesulfonyl)-5-methoxy-2-oxo-3-(2,5-dimethoxyphenyl)-2,3-dihydro-1H-indole-3-yl] ester dihydrochloride 4-(1-Methyl-piperidine-4-yl)-piperazine-1-carboxylic acid-[1-(benzenesulfonyl)-5-methoxy-2-oxo-3-(2,5-dimethoxyphenyl)-2,3-dihydro-1H-indole-3-yl] ester dihydrochloride -(4-Methyl-piperidine-1-yl)-piperazine-1-carboxylic acid-[1-benzenesulfonyl-5-chloro-2-oxo-3-(2-methoxy-phenyl)-2,3-dihydro-1H-indole-3-yl] ester 4-(1-Methyl-piperidine-4-yl)-piperazine-1-carboxylic acid-[1-(2,4-dimethoxy-benzenesulfonyl)-5-methoxy-2-oxo-3-(2-propoxyphenyl)-2,3-dihydro-1H-indole-3-yl] ester 4-(1-Methyl-piperidine-4-yl)-piperazine-1-carboxylic acid-[1-(2,4-dimethoxy-benzenesulfonyl)-5-chloro-2-oxo-3-(2-methoxyphenyl)-2,3-dihydro-1H-indole-3-yl] amide dihydrochloride 4-(1-Methyl-piperidine-4-yl)-piperazine-1-carboxylic acid-[1-benzenesulfonyl-5-chloro-2-oxo-3-phenyl-2,3-dihydro-1H-indole-3-yl] ester dihydrochloride 4-(4-Methyl-piperazine-1-yl)-piperidine-1-carboxylic acid-[1-benzenesulfonyl-5-chloro-2-oxo-3-phenyl-2,3-dihydro-1H-indole-3-yl] ester 4-(1-Methyl-piperidine-4-yl)-piperazine-1-carboxylic acid-[1-(2,4-dimethoxy-benzenesulfonyl)-5-methoxy-2-oxo-3-(2-methoxyphenyl)-2,3-dihydro-1H-indole-3-yl] ester dihydrochloride 4-(4-Methyl-piperazine-1-yl)-piperidine-1-carboxylic acid-[1-benzenesulfonyl-5-methyl-2-oxo-3-phenyl-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2-methylphenyl)-2,3-dihydro-1H-indole-3-yl] ester dihydrochloride 4-(Piperidine-4-yl)-piperazine-1-carboxylic acid-[1-(2,4-dimethoxy-benzenesulfonyl)-5-methoxy-2-oxo-3-(2-methoxyphenyl)-2,3-dihydro-1H-indole-3-yl] ester 4-(1-Methyl-piperidine-4-yl)-piperazine-1-carboxylic acid-[1-(2,4-dimethoxy-benzenesulfonyl)-5-fluoro-2-oxo-3-(2-methoxyphenyl)-2,3-dihydro-1H-indole-3-yl] ester 4-(1-Methyl-piperidine-4-yl)-piperazine-1-carboxylic acid-[1-(2-cyano-benzenesulfonyl)-5-methoxy-2-oxo-3-(2-methylphenyl)-2,3-dihydro-1H-indole-3-yl] ester dihydrochloride 4-(1-Methyl-piperidine-4-yl)-piperazine-1-carboxylic acid-[1-(4-bromo-2-methyl-benzenesulfonyl)-5-methoxy-2-oxo-3-(2-methylphenyl)-2,3-dihydro-1H-indole-3-yl] ester dihydrochloride 4-(1-Benzyl-piperidine-4-yl)-piperazine-1-carboxylic acid-[1-(2,4-dimethoxy-benzenesulfonyl)-5-methoxy-2-oxo-3-(2-methoxyphenyl)-2,3-dihydro-1H-indole-3-yl] ester 4-(1-Methyl-piperidine-4-yl)-piperazine-1-carboxylic acid-[1-(2,4-dimethoxy-benzenesulfonyl)-5-methyl-2-oxo-3-(2-methylphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-cyano-2-oxo-3-(2-methylphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2-methoxyphenyl)-2,3-dihydro-1H-indole-3-yl] amide dihydrochloride 4-(1-Methyl-piperidine-4-yl)-piperazine-1-carboxylic acid-[1-(2,4-dimethoxy-benzenesulfonyl)-5-methyl-2-oxo-3-(2-methoxyphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2-isopropyl phenyl)-2,3-dihydro-1H-indole-3-yl] ester dihydrochloride 4-(1-Methyl-piperidine-4-yl-piperazine-1-carboxylic acid-[1-(4-methoxy-benzenesulfonyl)-5-methoxy-2-oxo-3-(2-isopropylphenyl)-2,3-dihydro-1H-indole-3-yl] ester dihydrochloride 4-(1-Methyl-piperidine-4-yl)-piperazine-1-carboxylic acid-[1-(3,4-dimethoxy-benzenesulfonyl)-5-methoxy-2-oxo-3-(2-isopropylphenyl)-2,3-dihydro-1H-indole-3-yl] ester dihydrochloride 4-(1-Methyl-piperidine-4-yl)-piperazine-1-carboxylic acid-[1-(4-isopropyl-benzenesulfonyl)-5-methoxy-2-oxo-3-(2-isopropylphenyl)-2,3-dihydro-1H-indole-3-yl] ester dihydrochloride 4-(1-Methyl-piperidine-4-yl)-piperazine-1-carboxylic acid-[1-(2-cyano-benzenesulfonyl)-5-methoxy-2-oxo-3-(2-isopropylphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-2-oxo-3-(2-methoxyphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2-isopropoxyphenyl)-2,3-dihydro-1H-indole-3-yl] ester dihydrochloride 4-(1-Methyl-piperidine-4-yl)-piperazine-1-carboxylic acid-[1-(2-cyano-benzenesulfonyl)-5-methoxy-2-oxo-3-(2-isopropoxyphenyl)-2,3-dihydro-1H-indole-3-yl] ester dihydrochloride 4-(1-Methyl-piperidine-4-yl)-piperazine-1-carboxylic acid-[1-(2-methoxy-4-methyl-benzene)-sulfonyl-5-methoxy-2-oxo-3-(2-isopropoxyphenyl)-2,3-dihydro-1H-indole-3-yl] ester dihydrochloride 4-(1-Methyl-piperidine-4-yl)-piperazine-1-carboxylic acid-[1-(2-methyl-benzenesulfonyl)-5-methoxy-2-oxo-3-(2-isopropyl phenyl)-2,3-dihydro-1H-indole-3-yl] ester dihydrochloride 4-(1-Methyl-piperidine-4-yl)-piperazine-1-carboxylic acid-[1-(2-methyl-benzenesulfonyl)-5-methoxy-2-oxo-3-(2-isopropoxyphenyl)-2,3-dihydro-1H-indole-3-yl] ester dihydrochloride 4-(1-Methyl-piperidine-4-yl)-piperazine-1-carboxylic acid-[1-(2-methyl-benzenesulfonyl)-5-methoxy-2-oxo-3-(2-ethoxyphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2-ethoxyphenyl)-2,3-dihydro-1H-indole-3-yl] ester dihydrochloride 4-(1-Methyl-piperidine-4-yl)-piperazine-1-carboxylic acid-[1-(2-methyl-benzenesulfonyl)-5-methoxy-2-oxo-3-(2-methoxyphenyl)-2,3-dihydro-1H-indole-3-yl] ester dihydrochloride 4-(1-Methyl-piperidine-4-yl)-piperazine-1-carboxylic acid-[1-(3-cyano-benzenesulfonyl)-5-methoxy-2-oxo-3-(2-ethoxyphenyl)-2,3-dihydro-1H-indole-3-yl] ester dihydrochloride 4-(1-Methyl-piperidine-4-yl)-piperazine-1-carboxylic acid-[1-(4-ethyl-benzenesulfonyl)-5-methoxy-2-oxo-3-(2-ethoxyphenyl)-2,3-dihydro-1H-indole-3-yl] ester dihydrochloride 4-(1-Methyl-piperidine-4-yl)-piperazine-1-carboxylic acid-[1-(2-methyl-benzenesulfonyl)-5-methoxy-2-oxo-3-(2-propoxyphenyl)-2,3-dihydro-1H-indole-3-yl] ester dihydrochloride 4-(1-Methyl-piperidine-4-yl)-piperazine-1-carboxylic acid-[1-(2-methoxy-4-methyl-benzenesulfonyl)-5-methoxy-2-oxo-3-(2-propoxyphenyl)-2,3-dihydro-1H-indole-3-yl] ester dihydrochloride 4-(1-Methyl-piperidine-4-yl)-piperazine-1-carboxylic acid-[1-benzenesulfonyl-5-methyl-2-oxo-3-phenyl-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2-ethylphenyl)-2,3-dihydro-1H-indole-3-yl] ester dihydrochloride 4-(1-Methyl-piperidine-4-yl)-piperazine-1-carboxylic acid-[1-(2,4-dimethoxy-benzenesulfonyl)-5-methoxy-2-oxo-3-(2,5-dimethoxyphenyl)-2,3-dihydro-1H-indole-3-yl] ester dihydrochloride 4-(1-Methyl-piperidine-4-yl)-piperazine-1-carboxylic acid-[1-(2-methyl-benzenesulfonyl)-5-methoxy-2-oxo-3-(2,5-dimethoxyphenyl)-2,3-dihydro-1H-indole-3-yl] ester dihydrochloride 4-(1-Methyl-piperidine-4-yl)-piperazine-1-carboxylic acid-[1-(benzenesulfonyl)-5-methoxy-2-oxo-3-(2,5-dimethoxyphenyl)-2,3-dihydro-1H-indole-3-yl] ester dihydrochloride 4-(1-Methyl-piperidine-4-yl)-piperazine-1-carboxylic acid-[1-(4-cyano-1-benzenesulfonyl)-5-chloro-2-oxo-3-(2-ethoxyphenyl)-2,3-dihydro-1H-indole-3-yl] ester 4-(1-Methyl-piperidine-4-yl)-piperazine-1-carboxylic acid-[1-(2-methoxy-1-benzenesulfonyl)-5-chloro-2-oxo-3-(2-ethoxyphenyl)-2,3-dihydro-1H-indole-3-yl] ester 4-(1-Methyl-piperidine-4-yl)-piperazine-1-carboxylic acid-[1-(2-methoxy-4-methyl-1-benzenesulfonyl)-5-chloro-2-oxo-3-(2-ethoxyphenyl)-2,3-dihydro-1H-indole-3-yl] ester 4-(1-Methyl-piperidine-4-yl)-piperazine-1-carboxylic acid-[1-benzenesulfonyl-5-chloro-2-oxo-3-(2-ethoxyphenyl)-2,3-dihydro-1H-indole-3-yl] ester 4-(1-Methyl-piperidine-4-yl)-piperazine-1-carboxylic acid-[1-(2,4-dimethoxy-1-benzenesulfonyl)-5-chloro-2-oxo-3-(2-ethoxyphenyl)-2,3-dihydro-1H-indole-3-yl] ester 4-(1-Methyl-piperidine-4-yl)-piperazine-1-carboxylic acid-[1-(2,4-dimethoxy-1-benzenesulfonyl)-5-chloro-2-oxo-3-(2-methoxyphenyl)-2,3-dihydro-1H-indole-3-yl] ester dihydrochloride 4-(1-Methyl-piperidine-4-yl)-piperazine-1-carboxylic acid-[1-(2-methoxy-4-methyl-1-benzenesulfonyl)-5-chloro-2-oxo-3-(2-ethoxyphenyl)-2,3-dihydro-1H-indole-3-yl] amide 4-(1-Methyl-piperidine-4-yl)-piperazine-1-carboxylic acid-[1-(2,4,6-trimethyl-1-benzenesulfonyl)-5-chloro-2-oxo-3-(2-ethoxyphenyl)-2,3-dihydro-1H-indole-3-yl] ester 4-(1-Methyl-piperidine-4-yl)-piperazine-1-carboxylic acid-[1-(2,4-dichloro-1-benzenesulfonyl)-5-methoxy-2-oxo-3-(2-ethoxyphenyl)-2,3-dihydro-1H-indole-3-yl] ester 4-(1-Methyl-piperidine-4-yl)-piperazine-1-carboxylic acid-[1-(2-trifluoromethoxy-1-benzenesulfonyl)-5-methoxy-2-oxo-3-(2-ethoxyphenyl)-2,3-dihydro-1H-indole-3-yl] ester 4-(1-Methyl-piperidine-4-yl)-piperazine-1-carboxylic acid-[1-(2-methoxy-1-benzenesulfonyl)-5-methoxy-2-oxo-3-(2-ethoxyphenyl)-2,3-dihydro-1H-indole-3-yl] ester 4-(1-Methyl-piperidine-4-yl)-piperazine-1-carboxylic acid-[1-benzenesulfonyl-5-methoxy-2-oxo-3-(2-ethoxyphenyl)-2,3-dihydro-1H-indole-3-yl] ester 1-(2,4-Dimethoxy-1-benzenesulfonyl)-5-methoxy-3-(2-methoxyphenyl)-3{2-[(4-methyl-piperidine-1-yl)-piperazine-1-yl]-2-oxo-ethoxy}-1,3-dihydroindolone dihydrochloride 1-(2,4-Dimethoxy-1-benzenesulfonyl)-5-methoxy-3-(2-methoxyphenyl)-3{2-[(4-methyl-piperazine-1-yl)-piperidine-1-yl]-2-oxo-ethoxy}-1,3-dihydroindolone 4-(4-Methyl-piperazine-1-yl)-piperidine-1-carboxylic acid-[1-(2,4-dimethoxy-1-benzenesulfonyl)-5-methoxy-2-oxo-3-(2-methoxyphenyl)-2,3-dihydro-1H-indole-3-yl] ester dihydrochloride 4-(1-Methyl-piperidine-4-yl)-piperazine-1-carboxylic acid-[1-(2-methyl-1-benzenesulfonyl)-5-methoxy-2-oxo-3-[2-(2-methoxyethyl)phenyl]-2,3-dihydro-1H-indole-3-yl] ester dihydrochloride 4-(1-Methyl-piperidine-4-yl)-piperazine-1-carboxylic acid-[1-(2-methoxy-4-methyl-1-benzenesulfonyl)-5-methoxy-2-oxo-3-[2-(2-methoxyethyl)phenyl]-2,3-dihydro-1H-indole-3-yl] ester dihydrochloride 4-(1-Methyl-piperidine-4-yl)-piperazine-1-carboxylic acid-[1-(2,4-dimethoxy-1-benzenesulfonyl)-5-methoxy-2-oxo-3-[2-(2-methoxyethyl)phenyl]-2,3-dihydro-1H-indole-3-yl] ester dihydrochloride 4-(1-Methyl-piperidine-4-yl)-piperazine-1-carboxylic acid-[5-chloro-1-(2,4-dimethoxy-benzenesulfonyl)-3-(2-methoxymethyl-phenyl)-2-oxo-2,3-dihydro-1H-indole-3-yl] ester 4-(1-Methyl-piperidine-4-yl)-piperazine-1-carboxylic acid-[1-(2,4-dimethoxy-benzenesulfonyl)-5-methoxy-2-oxo-3-(2-ethoxyphenyl)-2,3-dihydro-1H-indole-3-yl] amide 4-(1-Methyl-piperidine-4-yl)-piperazine-1-carboxylic acid-[1-benzenesulfonyl-5-methoxy-2-oxo-3-(2-ethoxyphenyl)-2,3-dihydro-1H-indole-3-yl] amide dihydrochloride 4-(1-Methyl-piperidine-4-yl)-piperazine-1-carboxylic acid-[1-benzenesulfonyl-5-cyano-2-oxo-3-(2-ethoxyphenyl)-2,3-dihydro-1H-indole-3-yl] ester 4-(1-Methyl-piperidine-4-yl)-piperazine-1-carboxylic acid-[1-(2,4-dimethoxy-1-benzenesulfonyl)-5-cyano-2-oxo-3-(2-ethoxyphenyl)-2,3-dihydro-1H-indole-3-yl] ester 4-(1-Methyl-piperidine-4-yl)-piperazine-1-carboxylic acid-[1-(2,4-dichloro-1-benzenesulfonyl)-5-cyano-2-oxo-3-(2-ethoxyphenyl)-2,3-dihydro-1H-indole-3-yl] ester 4-(1-Methyl-piperidine-4-yl)-piperazine-1-carboxylic acid-[1-(2-methoxy-1-benzenesulfonyl)-5-cyano-2-oxo-3-(2-ethoxyphenyl)-2,3-dihydro-1H-indole-3-yl] ester 4-(1-Methyl-piperidine-4-yl)-piperazine-1-carboxylic acid-[1-(2,4-dimethoxy-benzenesulfonyl)-5-chloro-2-oxo-3-(2-ethoxyphenyl)-2,3-dihydro-1H-indole-3-yl] amide dihydrochloride 4-(1-Methyl-piperidine-4-yl)-piperazine-1-carboxylic acid-[1-benzenesulfonyl-5-chloro-2-oxo-3-(2-ethoxyphenyl)-2,3-dihydro-1H-indole-3-yl] amide dihydrochloride 4-(1-Methyl-piperidine-4-yl)-piperazine-1-carboxylic acid-[1-(2,4,6-trimethyl-1-benzenesulfonyl)-5-chloro-2-oxo-3-(2-ethoxyphenyl)-2,3-dihydro-1H-indole-3-yl] amide dihydrochloride 4-(1-Methyl-piperidine-4-yl)-piperazine-1-carboxylic acid-[1-(4-isopropyl-1-benzenesulfonyl)-5-chloro-2-oxo-3-(2-ethoxyphenyl)-2,3-dihydro-1H-indole-3-yl] amide 4-(1-Methyl-piperidine-4-yl)-piperazine-1-carboxylic acid-[1-(4-cyano-1-benzenesulfonyl)-5-chloro-2-oxo-3-(2-ethoxyphenyl)-2,3-dihydro-1H-indole-3-yl] amide 4-(1-Methyl-piperidine-4-yl)-piperazine-1-carboxylic acid-[5-chloro-3-(2-ethoxy-phenyl)-1-(2-methoxy-benzenesulfonyl)-2-oxo-2,3-dihydro-1H-indole-3-yl] amide 4-(1-Methyl-piperidine-4-yl)-piperazine-1-carboxylic acid-[1-(2,4-dimethoxy-benzenesulfonyl)-3-(2-ethoxy-phenyl)-5-fluoro-2-oxo-2,3-dihydro-1H-indole-3-yl] ester 4-(1-Methyl-piperidine-4-yl)-piperazine-1-carboxylic acid-[1-benzenesulfonyl-3-(2-ethoxy-phenyl)-5-fluoro-2-oxo-2,3-dihydro-1H-indole-3-yl] ester 4-(1-Methyl-piperidine-4-yl)-piperazine-1-carboxylic acid-[3-(2-ethoxy-phenyl)-5-methoxy-1-(4-methoxy-benzenesulfonyl)-2-oxo-2,3-dihydro-1H-indole-3-yl] ester 4-(1-Methyl-piperidine-4-yl)-piperazine-1-carboxylic acid-[3-(2-isopropoxyphenyl)-5-methoxy-1-(4-methoxy-benzenesulfonyl)-2-oxo-2,3-dihydro-1H-indole-3-yl] ester 4-(1-Methyl-piperidine-4-yl)-piperazine-1-carboxylic acid-[5-methoxy-1-(4-methoxy-benzenesulfonyl)-2-oxo-3-(2-propoxy-phenyl)-2,3-dihydro-1H-indole-3-yl] ester 4-(1-Methyl-piperidine-4-yl)-piperazine-1-carboxylic acid-[5-chloro-3-(2-ethoxy-phenyl)-1-(4-methoxy-benzenesulfonyl)-2-oxo-2,3-dihydro-1H-indole-3-yl] amide 4-(1-Methyl-piperidine-4-yl)-piperazine-1-carboxylic acid-{5-methoxy-1-(2-methoxy-benzenesulfonyl)-3-[2-(2-methoxy-ethyl)-phenyl]-2-oxo-2,3-dihydro-1H-indole-3-yl}-amide dihydrochloride 4-(1-Methyl-piperidine-4-yl)-piperazine-1-carboxylic acid-[5-methoxy-1-(2-methoxy-benzenesulfonyl)-2-oxo-3-(2-propoxy-phenyl)-2,3-dihydro-1H-indole-3-yl] ester 4-(1-Methyl-piperidine-4-yl)-piperazine-1-carboxylic acid-[3-(2-isopropoxy-phenyl)-5-methoxy-1-(2-methoxy-benzenesulfonyl)-2-oxo-2,3-dihydro-1H-indole-3-yl] ester 4-(1-Methyl-piperidine-4-yl)-piperazine-1-carboxylic acid-[5-methoxy-1-(4-methoxy-benzenesulfonyl)-3-(2-methoxymethyl-phenyl)-2-oxo-2,3-dihydro-1H-indole-3-yl] ester 4-(1-Methyl-piperidine-4-yl)-piperazine-1-carboxylic acid-[1-benzenesulfonyl-5-chloro-3-(2-methoxymethyl-phenyl)-2-oxo-2,3-dihydro-1H-indole-3-yl] ester 4-(4-Methyl-piperazine-1-yl)-piperidine-1-carboxylic acid-[3-(2-ethoxy-phenyl)-5-methoxy-1-(2-methoxy-benzenesulfonyl)-2-oxo-2,3-dihydro-1H-indole-3-yl] ester 4-(4-Methyl-piperazine-1-yl)-piperidine-1-carboxylic acid-[1-(2,4-dimethoxy-benzenesulfonyl)-3-(2-ethoxy-phenyl)-5-methoxy-2-oxo-2,3-dihydro-1H-indole-3-yl] ester 4-(4-Methyl-piperazine-1-yl)-piperidine-1-carboxylic acid-[3-(2-ethoxy-phenyl)-5-methoxy-1-(4-methoxy-benzenesulfonyl)-2-oxo-2,3-dihydro-1H-indole-3-yl] ester 4-(4-Methyl-piperazine-1-yl)-piperidine-1-carboxylic acid-[3-(2-isopropoxy-phenyl)-5-methoxy-1-(2-methoxy-benzenesulfonyl)-2-oxo-2,3-dihydro-1H-indole-3-yl] ester 4-(4-Methyl-piperazine-1-yl)-piperidine-1-carboxylic acid-[1-(2,4-dimethoxy-benzenesulfonyl)-3-(2-isopropoxy-phenyl)-5-methoxy-2-oxo-2,3-dihydro-1H-indole-3-yl] ester 4-(4-Methyl-piperazine-1-yl)-piperidine-1-carboxylic acid-[5-chloro-3-(2-ethoxy-phenyl)-1-(4-methoxy-benzenesulfonyl)-2-oxo-2,3-dihydro-1H-indole-3-yl] ester 4-(4-Methyl-piperazine-1-yl)-piperidine-1-carboxylic acid-[3-(2-isopropoxy-phenyl)-5-methoxy-1-(4-methoxy-benzenesulfonyl)-2-oxo-2,3-dihydro-1H-indole-3-yl] ester 4-(4-Methyl-piperazine-1-yl)-piperidine-1-carboxylic acid-[5-chloro-3-(2-ethoxy-phenyl)-1-(2-methoxy-benzenesulfonyl)-2-oxo-2,3-dihydro-1H-indole-3-yl] ester 4-(4-Methyl-piperazine-1-yl)-piperidine-1-carboxylic acid-[5-chloro-1-(2,4-dimethoxy-benzenesulfonyl)-3-(2-ethoxy-phenyl)-2-oxo-2,3-dihydro-1H-indole-3-yl]-ester 4-(1-Methyl-piperidine-4-yl)-piperazine-1-carboxylic acid-[1-(2-methoxy-benzenesulfonyl)-3-(2-methoxy-phenyl)-2-oxo-6-trifluoromethyl-2,3-dihydro-1H-indole-3-yl] ester 4-(1-Methyl-piperidine-4-yl)-piperazine-1-carboxylic acid-[3-(2-ethoxy-phenyl)-5-fluoro-1-(2-methoxy-benzenesulfonyl)-2-oxo-2,3-dihydro-1H-indole-3-yl] ester 4-(1-Methyl-piperidine-4-yl)-piperazine-1-carboxylic acid-[3-(2-ethoxy-phenyl)-5-fluoro-1-(4-methoxy-benzenesulfonyl)-2-oxo-2,3-dihydro-1H-indole-3-yl] ester dihydrochloride 4-(1-Methyl-piperidine-4-yl)-piperazine-1-carboxylic acid-[1-(4-cyano-benzenesulfonyl)-3-(2-ethoxy-phenyl)-5-fluoro-2-oxo-2,3-dihydro-1H-indole-3-yl] ester 4-(1-Methyl-piperidine-4-yl)-piperazine-1-carboxylic acid-[5-chloro-3-(2-ethoxy-phenyl)-1-(4-methoxy-benzenesulfonyl)-2-oxo-2,3-dihydro-1H-indole-3-yl] ester dihydrochloride 4-(1-Methyl-piperidine-4-yl)-piperazine-1-carboxylic acid-[5-chloro-1-(2-methoxy-benzenesulfonyl)-3-(2-methoxymethyl-phenyl)-2-oxo-2,3-dihydro-1H-indole-3-yl] ester 4-(1-Methyl-piperidine-4-yl)-piperazine-1-carboxylic acid-[3-(2-ethoxy-phenyl)-5-methoxy-1-(2-methoxy-benzenesulfonyl)-2-oxo-2,3-dihydro-1H-indole-3-yl] amide 4-(1-Methyl-piperidine-4-yl)-piperazine-1-carboxylic acid-[3-(2-ethoxy-phenyl)-5-methoxy-1-(4-methoxy-benzenesulfonyl)-2-oxo-2,3-dihydro-1H-indole-3-yl] amide 4-(1-Methyl-piperidine-4-yl)-piperazine-1-carboxylic acid-[1-(2,4-dimethoxy-benzenesulfonyl)-3-(2-methoxy-phenyl)-2-oxo-6-trifluoromethyl-2,3-dihydro-1H-indole-3-yl] ester 4-(4-Methyl-piperazine-1-yl)-piperidine-1-carboxylic acid-[5-chloro-3-(2-ethoxy-phenyl)-1-(4-methoxy-benzenesulfonyl)-2-oxo-2,3-dihydro-1H-indole-3-yl] amide dihydrochloride 4-(4-Methyl-piperazine-1-yl)-piperidine-1-carboxylic acid-[5-chloro-1-(2,4-dimethoxy-benzenesulfonyl)-3-(2-ethoxy-phenyl)-2-oxo-2,3-dihydro-1H-indole-3-yl] amide dihydrochloride 4-(4-Methyl-piperazine-1-yl)-piperidine-1-carboxylic acid-[5-chloro-3-(2-ethoxy-phenyl)-1-(2-methoxy-benzenesulfonyl)-2-oxo-2,3-dihydro-1H-indole-3-yl] amide 4-(4-Methyl-piperazine-1-yl)-piperazine-1-carboxylic acid-[5-cyano-3-(2-ethoxy-phenyl)-2-oxo-1-(toluene-2-sulfonyl)-2,3-dihydro-1H-indole-3-yl] ester 4-(1-Methyl-piperidine-4-yl)-piperazine-1-carboxylic acid-[5-cyano-3-(2-ethoxy-phenyl)-2-oxo-1-(toluene-4-sulfonyl)-2,3-dihydro-1H-indole-3-yl] ester 4-(1-Methyl-piperidine-4-yl)-piperazine-1-carboxylic acid-[1-(2-chloro-benzenesulfonyl)-5-cyano-3-(2-ethoxy-phenyl)-2-oxo-2,3-dihydro-1H-indole-3-yl] ester 4-(1-Methyl-piperidine-4-yl)-piperazine-1-carboxylic acid-[5-cyano-1-(2,5-dimethoxy-benzenesulfonyl)-3-(2-ethoxy-phenyl)-2-oxo-2,3-dihydro-1H-indole-3-yl] ester 4-(1-Methyl-piperidine-4-yl)-piperazine-1-carboxylic acid-[5-cyano-1-(2-cyano-benzenesulfonyl)-3-(2-ethoxy-phenyl)-2-oxo-2,3-dihydro-1H-indole-3-yl] ester 4-(1-Methyl-piperidine-4-yl)-piperazine-1-carboxylic acid-[5-cyano-1-(2,4-difluoro-benzenesulfonyl)-3-(2-ethoxy-phenyl)-2-oxo-2,3-dihydro-1H-indole-3-yl] ester 4-(1-Methyl-piperidine-4-yl)-piperazine-1-carboxylic acid-[5-cyano-1-(4-fluoro-benzenesulfonyl)-3-(2-ethoxy-phenyl)-2-oxo-2,3-dihydro-1H-indole-3-yl] ester 4-(1-Methyl-piperidine-4-yl)-piperazine-1-carboxylic acid-[5-cyano-3-(2-ethoxy-phenyl)-1-(4-isopropyl-benzenesulfonyl)-2-oxo-2,3-dihydro-1H-indole-3-yl] ester 4-(1-Methyl-piperidine-4-yl)-piperazine-1-carboxylic acid-[5-cyano-3-(2-ethoxy-phenyl)-1-(2-fluoro-benzenesulfonyl)-2-oxo-2,3-dihydro-1H-indole-3-yl] ester 4-(1-Methyl-piperidine-4-yl)-piperazine-1-carboxylic acid-1-[5-chloro-2-methoxy-benzenesulfonyl)-5-cyano-3-(2-ethoxy-phenyl)-2-oxo-2,3-dihydro-1H-indole-3-yl] ester 4-(1-Methyl-piperidine-4-yl)-piperazine-1-carboxylic acid-[5-cyano-3-(2-ethoxy-phenyl)-1-(2-methoxy-5-methyl-benzenesulfonyl)-2-oxo-2,3-dihydro-1H-indole-3-yl] ester 4-(1-Methyl-piperidine-4-yl)-piperazine-1-carboxylic acid-[5-cyano-3-(2-ethoxy-phenyl)-1-(2-methoxy-4-methyl-benzenesulfonyl)-2-oxo-2,3-dihydro-1H-indole-3-yl] ester 4-(1-Methyl-piperidine-4-yl)-piperazine-1-carboxylic acid-[1-benzenesulfonyl-5-cyano-3-(2-ethoxy-phenyl)-2-oxo-2,3-dihydro-1H-indole-3-yl] amide dihydrochloride 4-(1-Methyl-piperidine-4-yl)-piperazine-1-carboxylic acid-[5-cyano-3-(2-ethoxy-phenyl)-1-(4-methoxy-benzenesulfonyl)-2-oxo-2,3-dihydro-1H-indole-3-yl] amide 4-(1-Methyl-piperidine-4-yl)-piperazine-1-carboxylic acid-[5-cyano-3-(2-ethoxy-phenyl)-1-(2-methoxy-benzenesulfonyl)-2-oxo-2,3-dihydro-1H-indole-3-yl] amide dihydrochloride 4-(1-Methyl-piperidine-4-yl)-piperazine-1-carboxylic acid-[5-cyano-3-(2-ethoxy-phenyl)-1-(2,4-dimethoxy-benzenesulfonyl)-2-oxo-2,3-dihydro-1H-indole-3-yl] amide 4-(1-Methyl-piperidine-4-yl)-piperazine-1-carboxylic acid-[1-(4-acetylamino-benzenesulfonyl)-5-cyano-3-(2-ethoxy-phenyl)-2-oxo-2,3-dihydro-1H-indole-3-yl] ester 4-(1-Methyl-piperidine-4-yl)-piperazine-1-carboxylic acid-[1-(2,4-dimethoxy-benzenesulfonyl)-3-(2-ethoxy-phenyl)-5-fluoro-2-oxo-2,3-dihydro-1H-indole-3-yl] amide 4-(1-Methyl-piperidine-4-yl)-piperazine-1-carboxylic acid-[1-(2-methoxy-benzenesulfonyl)-3-(2-ethoxy-phenyl)-5-fluoro-2-oxo-2,3-dihydro-1H-indole-3-yl] amide 4-(1-Methyl-piperidine-4-yl)-piperazine-1-carboxylic acid-[1-(4-methoxy-benzenesulfonyl)-3-(2-ethoxy-phenyl)-5-fluoro-2-oxo-2,3-dihydro-1H-indole-3-yl] amide dihydrochloride 4-(1-Methyl-piperidine-4-yl)-piperazine-1-carboxylic acid-[3-(2-ethoxy-phenyl)-5-isopropyl-1-(2-methoxy-benzenesulfonyl)-2-oxo-2,3-dihydro-1H-indole-3-yl] ester 4-(1-Methyl-piperazine-4-yl)-piperidine-1-carboxylic acid-[5-cyano-3-(2-ethoxy-phenyl)-1-(2-methoxy-benzenesulfonyl)-2-oxo-2,3-dihydro-1H-indole-3-yl] amide 4-(1-Methyl-piperidine-4-yl)-piperazine-1-carboxylic acid-[3-(2-ethoxy-phenyl)-5-fluoro-1-(2-methoxy-benzenesulfonyl)-2-oxo-2,3-dihydro-1H-indole-3-yl] amide 4-(1-Methyl-piperidine-4-yl)-piperazine-1-carboxylic acid-[3-(2-ethoxy-phenyl)-5-isopropyl-1-(4-methoxy-benzenesulfonyl)-2-oxo-2,3-dihydro-1H-indole-3-yl] ester 4-(1-Methyl-piperazine-4-yl)-piperidine-1-carboxylic acid-[5-cyano-3-(2-ethoxy-phenyl)-1-(2,4-dimethoxy-benzenesulfonyl)-2-oxo-2,3-dihydro-1H-indole-3-yl] amide (−)-4-(1-Methyl-piperidine-4-yl)-piperazine-1-carboxylic acid-[5-cyano-3-(2-ethoxy-phenyl)-1-(2-methoxy-benzenesulfonyl)-2-oxo-2,3-dihydro-1H-indole-3-yl] ester (+)-4-(1-Methyl-piperidine-4-yl)-piperazine-1-carboxylic acid-[5-cyano-3-(2-ethoxy-phenyl)-1-(2-methoxy-benzenesulfonyl)-2-oxo-2,3-dihydro-1H-indole-3-yl] ester (−)-4-(1-Methyl-piperidine-4-yl)-piperazine-1-carboxylic acid-[5-cyano-3-(2-ethoxy-phenyl)-1-(2,4-dimethoxy-benzenesulfonyl)-2-oxo-2,3-dihydro-1H-indole-3-yl] ester (+)-4-(1-Methyl-piperidine-4-yl)-piperazine-1-carboxylic acid-[5-cyano-3-(2-ethoxy-phenyl)-1-(2,4-dimethoxy-benzenesulfonyl)-2-oxo-2,3-dihydro-1H-indole-3-yl] ester 4-(4-Methyl-piperazine-1-yl)-piperidine-1-carboxylic acid-[1-benzenesulfonyl-5-cyano-3-(2-ethoxy-phenyl)-2-oxo-2,3-dihydro-1H-indole-3-yl] amide 4-(1-Methyl-piperidine-4-yl)-piperazine-1-carboxylic acid-[1-benzenesulfonyl-3-(2-ethoxy-phenyl)-5-isopropyl-2-oxo-2,3-dihydro-1H-indole-3-yl] ester 4-(1-Methyl-piperidine-4-yl)-piperazine-1-carboxylic acid-[4-chloro-3-(2-methoxy-phenyl)-1-(2,4-dimethoxy-benzenesulfonyl)-2-oxo-2,3-dihydro-1H-indole-3-yl] ester 4-(1-Methyl-piperidine-4-yl)-piperazine-1-carboxylic acid-[4-chloro-3-(2-methoxy-phenyl)-1-(4-methoxy-benzenesulfonyl)-2-oxo-2,3-dihydro-1H-indole-3-yl]-ester 4-(1-Methyl-piperazine-4-yl)-piperidine-1-carboxylic acid-[3-(2-ethoxy-phenyl)-5-methoxy-1-(2-methoxy-benzenesulfonyl)-2-oxo-2,3-dihydro-1H-indole-3-yl] amide dihydrochloride 4-(1-Methyl-piperazine-4-yl)-piperidine-1-carboxylic acid-[3-(2-ethoxy-phenyl)-5-methoxy-1-(2,4-dimethoxy-benzenesulfonyl)-2-oxo-2,3-dihydro-1H-indole-3-yl] amide dihydrochloride 4-(1-Methyl-piperazine-4-yl)-piperidine-1-carboxylic acid-[3-(2-ethoxy-phenyl)-5-methoxy-1-(4-methoxy-benzenesulfonyl)-2-oxo-2,3-dihydro-1H-indole-3-yl] amide dihydrochloride 4-(4-Methyl-piperazine-1-yl)-piperidine-1-carboxylic acid-[1-benzenesulfonyl-3-(2-ethoxy-phenyl)-5-methoxy-2-oxo-2,3-dihydro-1H-indole-3-yl] amide dihydrochloride 4-(1-Methyl-piperidine-4-yl)-piperazine-1-carboxylic acid-[6-chloro-3-(2-methoxy-phenyl)-1-(4-methoxy-benzenesulfonyl)-2-oxo-2,3-dihydro-1H-indole-3-yl] ester 4-(1-Methyl-piperidine-4-yl)-piperazine-1-carboxylic acid-[1-(2,4-dimethoxy-benzenesulfonyl)-3-(2-ethoxy-phenyl)-5-isopropyl-2-oxo-2,3-dihydro-1H-indole-3-yl] ester 4-Piperidine-4-yl-piperazine-1-carboxylic acid-[5-cyano-1-(2,4-dimethoxy-benzenesulfonyl)-3-(2-ethoxy-phenyl)-2-oxo-2,3-dihydro-1H-indole-3-yl] ester dihydrochloride 4-(4-Methyl-piperazine-1-yl)-piperidine-1-carboxylic acid-[5-cyano-3-(2-ethoxy-phenyl)-1-(4-methoxy-benzenesulfonyl)-2-oxo-2,3-dihydro-1H-indole-3-yl] amide 4-(4-ethyl-piperidine-1-yl)-piperazine-1-carboxylic acid-[5-cyano-3-(2-ethoxy-phenyl)-1-(2,4-dimethoxy-benzenesulfonyl)-2-oxo-2,3-dihydro-1H-indole-3-yl] ester 4-(4-propyl-piperidine-1-yl)-piperazine-1-carboxylic acid-[5-cyano-3-(2-ethoxy-phenyl)-1-(2,4-dimethoxy-benzenesulfonyl)-2-oxo-2,3-dihydro-1H-indole-3-yl] ester 4-(4-isopropyl-piperidine-1-yl)-piperazine-1-carboxylic acid-[5-cyano-3-(2-ethoxy-phenyl)-1-(2,4-dimethoxy-benzenesulfonyl)-2-oxo-2,3-dihydro-1H-indole-3-yl] ester 4-(4-Methyl-piperidine-1-yl)-piperazine-1-carboxylic acid-[4-methyl-3-(2-ethoxy-phenyl)-1-(2,4-dimethoxy-benzenesulfonyl)-2-oxo-2,3-dihydro-1H-indole-3-yl] ester 4-(4-Methyl-piperidine-1-yl)-piperazine-1-carboxylic acid-[5-cyano-3-(2-ethoxy-phenyl)-1-(3,4-dibromo-benzenesulfonyl)-2-oxo-2,3-dihydro-1H-indole-3-yl] ester 4-(4-Methyl-piperidine-1-yl)-piperazine-1-carboxylic acid-[4-methoxy-3-(2-methoxy-phenyl)-1-(2-methoxy-benzenesulfonyl)-2-oxo-2,3-dihydro-1H-indole-3-yl] ester 4-(4-Methyl-piperidine-1-yl)-piperazine-1-carboxylic acid-[4-methoxy-3-(2-methoxy-phenyl)-1-(2,4-dimethoxy-benzenesulfonyl)-2-oxo-2,3-dihydro-1H-indole-3-yl] ester 4-(4-Methyl-piperidine-1-yl)-piperazine-1-carboxylic acid-[5-methoxy-3-(2-ethoxy-phenyl)-1-(2,4-dimethoxy-benzenesulfonyl)-2-oxo-2,3-dihydro-1H-indole-3-yl] ester 4-piperazine-1-yl-piperidine-1-carboxylic acid-[5-cyano-1-(2,4-dimethoxy-benzenesulfonyl)-3-(2-ethoxy-phenyl)-2-oxo-2,3-dihydro-1H-indole-3-yl] amide dihydrochloride 4-(4-Ethyl-piperazine-1-yl)-piperidine-1-carboxylic acid-[5-cyano-1-(2,4-dimethoxy-benzenesulfonyl)-3-(2-ethoxy-phenyl)-2-oxo-2,3-dihydro-1H-indole-3-yl] amide 4-(4-Propyl-piperazine-1-yl)-piperidine-1-carboxylic acid-[5-cyano-1-(2,4-dimethoxy-benzenesulfonyl)-3-(2-ethoxy-phenyl)-2-oxo-2,3-dihydro-1H-indole-3-yl] amide 4-(4-Propyl-piperazine-1-yl)-piperidine-1-carboxylic acid-[5-cyano-1-benzenesulfonyl-3-(2-ethoxy-phenyl)-2-oxo-2,3-dihydro-1H-indole-3-yl] amide 4-(4-Propyl-piperazine-1-yl)-piperidine-1-carboxylic acid-[5-cyano-1-(2-methoxy-benzenesulfonyl)-3-(2-ethoxy-phenyl)-2-oxo-2,3-dihydro-1H-indole-3-yl] amide 4-(4-isopropyl-piperazine-1-yl)-piperidine-1-carboxylic acid-[5-cyano-1-(2,4-dimethoxy-benzenesulfonyl)-3-(2-ethoxy-phenyl)-2-oxo-2,3-dihydro-1H-indole-3-yl] amide dihydrochloride 4-(4-Propyl-piperazine-1-yl)-piperidine-1-carboxylic acid-[5-cyano-1-(2,4-difluoro-benzenesulfonyl)-3-(2-ethoxy-phenyl)-2-oxo-2,3-dihydro-1H-indole-3-yl] ester 4-(4-Propyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] ester 4-(4-Propyl-piperazine-1-yl)-piperidine-1-carboxylic acid-[5-cyano-1-(2-fluoro-benzenesulfonyl)-3-(2-ethoxy-phenyl)-2-oxo-2,3-dihydro-1H-indole-3-yl] ester 4-(4-Propyl-piperazine-1-yl)-piperidine-1-carboxylic acid-[5-cyano-1-benzenesulfonyl-3-(2-ethoxy-phenyl)-2-oxo-2,3-dihydro-1H-indole-3-yl] ester 4-(4-Propyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] amide 4-(4-Propyl-piperazine-1-yl)-piperidine-1-carboxylic acid-[5-cyano-1-(2-fluoro-benzenesulfonyl)-3-(2-ethoxy-phenyl)-2-oxo-2,3-dihydro-1H-indole-3-yl] amide 4-(4-Propyl-piperazine-1-yl)-piperidine-1-carboxylic acid-[5-cyano-1-(2,4-difluoro-benzenesulfonyl)-3-(2-ethoxy-phenyl)-2-oxo-2,3-dihydro-1H-indole-3-yl] amide 4-(4-Propyl-piperazine-1-yl)-piperidine-1-carboxylic acid-[5-cyano-1-(2-methoxy-benzenesulfonyl)-3-(2-ethoxy-phenyl)-2-oxo-2,3-dihydro-1H-indole-3-yl] ester 4-(4-Methyl-piperazine-1-yl)-piperidine-1-carboxylic acid-[5-cyano-1-benzenesulfonyl-3-(2-ethoxy-phenyl)-2-oxo-2,3-dihydro-1H-indole-3-yl] ester dihydrochloride 4-(4-Methyl-piperazine-1-yl)-piperidine-1-carboxylic acid-[5-cyano-1-(2,4-difluoro-benzenesulfonyl)-3-(2-ethoxy-phenyl)-2-oxo-2,3-dihydro-1H-indole-3-yl] ester dihydrochloride 4-(4-Methyl-piperazine-1-yl)-piperidine-1-carboxylic acid-[5-cyano-1-(2-fluoro-benzenesulfonyl)-3-(2-ethoxy-phenyl)-2-oxo-2,3-dihydro-1H-indole-3-yl] ester 4-(4-Methyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] ester 4-(4-Methyl-piperazine-1-yl)-piperidine-1-carboxylic acid-[5-cyano-1-(2-methoxy-benzenesulfonyl)-3-(2-ethoxy-phenyl)-2-oxo-2,3-dihydro-1H-indole-3-yl] ester 4-(4-Methyl-piperazine-1-yl)-piperidine-1-carboxylic acid-[5-cyano-1-(2,4-dimethoxy-benzenesulfonyl)-3-(2-ethoxy-phenyl)-2-oxo-2,3-dihydro-1H-indole-3-yl] ester dihydrochloride 4-(4-Propargyl-3-yl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] ester 4-(4-Isopropyl-piperazine-1-yl)-piperidine-1-carboxylic acid-[5-cyano-1-benzenesulfonyl-3-(2-ethoxy-phenyl)-2-oxo-2,3-dihydro-1H-indole-3-yl] ester 4-(4-Isopropyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] ester 4-(4-Allyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] ester 4-(4-Isopropyl-piperazine-1-yl)-piperidine-1-carboxylic acid-[5-cyano-1-(2-methoxy-benzenesulfonyl)-3-(2-ethoxy-phenyl)-2-oxo-2,3-dihydro-1H-indole-3-yl] ester 4-(4-Ethyl-piperazine-1-yl)-piperidine-1-carboxylic acid-[5-cyano-1-benzenesulfonyl-3-(2-ethoxy-phenyl)-2-oxo-2,3-dihydro-1H-indole-3-yl] amide 4-(4-Ethyl-piperazine-1-yl)-piperidine-1-carboxylic acid-[5-cyano-1-(2-methoxy-benzenesulfonyl)-3-(2-ethoxy-phenyl)-2-oxo-2,3-dihydro-1H-indole-3-yl] amide 4-(4-Ethyl-piperazine-1-yl)-piperidine-1-carboxylic acid-[5-cyano-1-(2-fluoro-benzenesulfonyl)-3-(2-ethoxy-phenyl)-2-oxo-2,3-dihydro-1H-indole-3-yl] amide 4-(4-Propyl-piperazine-1-yl)-piperidine-1-carboxylic acid-[5-cyano-1-(2,4-dimethoxy-benzenesulfonyl)-3-(2-isopropoxy-phenyl)-2-oxo-2,3-dihydro-1H-indole-3-yl] amide 4-(4-Propyl-piperazine-1-yl)-piperidine-1-carboxylic acid-[5-cyano-1-(2-methoxy-benzenesulfonyl)-3-(2-isopropoxy-phenyl)-2-oxo-2,3-dihydro-1H-indole-3-yl] amide 4-(4-Propyl-piperazine-1-yl)-piperidine-1-carboxylic acid-[5-cyano-1-(4-methoxy-benzenesulfonyl)-3-(2-isopropoxy-phenyl)-2-oxo-2,3-dihydro-1H-indole-3-yl] amide 4-(4-Propyl-piperazine-1-yl)-piperidine-1-carboxylic acid-[5-cyano-1-(4-fluoro-benzenesulfonyl)-3-(2-isopropoxy-phenyl)-2-oxo-2,3-dihydro-1H-indole-3-yl] amide 4-(4-Isopropyl-piperazine-1-yl)-piperidine-1-carboxylic acid-[5-cyano-1-(2,4-dimethoxy-benzenesulfonyl)-3-(2-ethoxy-phenyl)-2-oxo-2,3-dihydro-1H-indole-3-yl] ester 4-(4-Isopropyl-piperazine-1-yl)-piperidine-1-carboxylic acid-[5-cyano-1-(2,4-difluoro-benzenesulfonyl)-3-(2-ethoxy-phenyl)-2-oxo-2,3-dihydro-1H-indole-3-yl] ester 4-(4-Isopropyl-piperazine-1-yl)-piperidine-1-carboxylic acid-[5-cyano-1-(2-fluoro-benzenesulfonyl)-3-(2-ethoxy-phenyl)-2-oxo-2,3-dihydro-1H-indole-3-yl] ester 4-(4-Isopropyl-piperazine-1-yl)-piperidine-1-carboxylic acid-[5-cyano-1-(4-fluoro-benzenesulfonyl)-3-(2-ethoxy-phenyl)-2-oxo-2,3-dihydro-1H-indole-3-yl] ester 4-(4-Propyl-piperazine-1-yl)-piperidine-1-carboxylic acid-[5-cyano-1-(4-fluoro-benzenesulfonyl)-3-(2-ethoxy-phenyl)-2-oxo-2,3-dihydro-1H-indole-3-yl] ester 3-(2-Ethoxy-phenyl)-1-benzenesulfonyl-2-oxo-3-{2-oxo-2-[4-(4-propyl-piperazine-1-yl)-piperidine-1-yl]-ethyl}-2,3-dihydro-1H-indole-5-carboxylic-acid nitrile 3-(2-Ethoxy-phenyl)-1-(2-methoxy-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile 3-(2-Ethoxy-phenyl)-1-(4-methoxy-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile 3-(2-Ethoxy-phenyl)-1-(2-fluoro-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile 3-(2-Ethoxy-phenyl)-1-(2,4-dimethoxy-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile 3-(2-Ethoxy-phenyl)-1-(2,4-difluoro-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile 3-(2-Ethoxy-phenyl)-1-(4-chloro-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile 4-(4-Isopropyl-piperazine-1-yl)-piperidine-1-carboxylic acid-[5-cyano-1-benzenesulfonyl-3-(2-ethoxy-phenyl)-2-oxo-2,3-dihydro-1H-indole-3-yl] amide 4-(4-Isopropyl-piperazine-1-yl)-piperidine-1-carboxylic acid-[5-cyano-1-(2-methoxy-benzenesulfonyl)-3-(2-ethoxy-phenyl)-2-oxo-2,3-dihydro-1H-indole-3-yl] amide 4-(4-Isopropyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] amide 4-(4-Isopropyl-piperazine-1-yl)-piperidine-1-carboxylic acid-[5-cyano-1-(2-fluoro-benzenesulfonyl)-3-(2-ethoxy-phenyl)-2-oxo-2,3-dihydro-1H-indole-3-yl] amide 4-(4-Isopropyl-piperazine-1-yl)-piperidine-1-carboxylic acid-[5-cyano-1-(2,4-difluoro-benzenesulfonyl)-3-(2-ethoxy-phenyl)-2-oxo-2,3-dihydro-1H-indole-3-yl] amide 4-(4-Ethyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] amide 4-(4-Ethyl-piperazine-1-yl)-piperidine-1-carboxylic acid-[5-cyano-1-(2,4-difluoro-benzenesulfonyl)-3-(2-ethoxy-phenyl)-2-oxo-2,3-dihydro-1H-indole-3-yl] amide 4-(4-Ethyl-piperazine-1-yl)-piperidine-1-carboxylic acid-[5-cyano-1-(4-fluoro-benzenesulfonyl)-3-(2-ethoxy-phenyl)-2-oxo-2,3-dihydro-1H-indole-3-yl] amide 4-(4-Propyl-piperazine-1-yl)-piperidine-1-carboxylic acid-[5-cyano-1-(4-fluoro-benzenesulfonyl)-3-(2-ethoxy-phenyl)-2-oxo-2,3-dihydro-1H-indole-3-yl] amide 4-(1-Methyl-piperidine-4-yl)-piperazine-1-carboxylic acid-[1-(4-methoxy-1-benzenesulfonyl)-5-cyano-2-oxo-3-(2-ethoxyphenyl)-2,3-dihydro-1H-indole-3-yl] ester 4-(4-Isopropyl-piperazine-1-yl)-piperidine-1-carboxylic acid-[5-cyano-1-(4-fluoro-benzenesulfonyl)-3-(2-ethoxy-phenyl)-2-oxo-2,3-dihydro-1H-indole-3-yl] amide 3-(2-Ethoxy-phenyl)-1-(4-fluoro-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile their tautomeric, enantiomeric and/or diastereomeric forms, and their prodrugs, as well as non-salt forms and other physiologically compatible salts of the compound or compounds according to the invention.

The compound or compounds according to the invention can be present as racemates or as enantiomerically-pure or diastereomerically-pure compounds. Preferably, the compounds are present as enantiomerically-pure or diastereomerically-pure compounds.

Physiologically compatible salts can be formed, for example, with the following anions:

Chloride, bromide, phosphate, carbonate, nitrate, perchlorate, sulfate, citrate, lactate, tartrate, maleate, fumarate, mandelate, benzoate, ascorbate, cinnamate, glycolate, methanesulfonate, formate, malonate, naphthalene-2-sulfonate, tosylate, salicylate and/or acetate. Further suitable acids are, for example, listed in "*Fortschritte der Arzneimittelforschung*", 1966, Birkhäuser Publishing House, Vol. 10, pp. 224-285.

In the context of the present description, the terms "alkyl" and "alkylene" always comprise unbranched and branched "alkyl" or "alkylene".

In the context of the description, $C_1$-$C_4$ alkyl is preferably methyl, ethyl, n-propyl, i-propyl, n-butyl, sec-butyl or t-butyl.

In the context of the description, $C_0$ alkylene or $(CH_2)_0$ indicates a single bond.

In the context of the description, $C_1$-$C_4$ alkylene is methylene, ethylene or branched or unbranched propylene or butylene.

In the context of the description, $C_1$-$C_6$ alkyl is methyl, ethyl or branched or unbranched propyl, butyl, pentyl or hexyl, preferably $C_1$-$C_4$ alkyl, i.e., methyl, ethyl, n-propyl, i-propyl, n-butyl, sec-butyl or t-butyl.

In the context of the description, $C_1$-$C_6$ alkylene is methylene, ethylene or branched or unbranched propylene, butylene, pentylene or hexylene, preferably $C_1$-$C_4$ alkylene, i.e., methylene, ethylene or branched or unbranched propylene or butylene.

The symbol

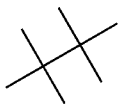

in the chemical formulas for Y and Z shows the positions of attachment of Y to X and Z and the positions of attachment of Z to Y. In the formulas for Y, each position of attachment can represent a bond to X or Z.

The compounds according to the invention are effective after administration in various ways, particularly orally.

The compounds according to the invention show good affinity to vasopressin receptors, for example, the subtype V1a and V1b vasopressin receptors.

Because the various vasopressin receptors impart very different effects of the vasopressin (M. Thibonnier, Exp. Opin. Invest. Drugs 1998, 7(5), 729-740; Serradeil-Le Gal, C., et al.; Prog Brain Res. 2002; 139:197-210), it is especially significant to obtain effects selectively, for example, on one vasopressin receptor, in order in this way to achieve the desired effect without simultaneously causing significant side-effects. For example, vasopressin produces effects on the kidney and its function via the receptor V2, which would be undesirable in the case of possible treatment of CNS diseases. Consequently, in addition to the actual affinity at the target receptor, the selectivity with respect to the other vasopressin receptors is also particularly significant. The compounds according to the invention display the advantage of having very good affinities to the desired receptors, such as vasopressin receptors V1b and V1a, while simultaneously having improved selectivity with respect to the other receptors, such as V2.

The present invention also provides the application of the compounds according to the invention for treatment and/or prophylaxis of diseases in which the progress of the disease depends at least partially on vasopressin, i.e., diseases that show an elevated vasopressin or oxytocin level, which can directly or indirectly contribute to the clinical picture.

Furthermore, the present invention provides the application of compounds according to the invention for the treatment and/or prophylaxis of diseases, such as diabetes insipidus, nocturnal enuresis, incontinence and diseases in which coagulation disorders occur, and/or for the delay of micturition.

The present invention also provides the application of the compounds according to the invention for treatment and/or prophylaxis of the following diseases: hypertension, pulmonary hypertension, cardiac insufficiency, myocardial infarction, coronary spasm, unstable angina, PTCA (percutaneous transluminal coronary angioplasty), ischemia of the heart, disorders of the renal system, oedemas, renal vasospasm, necrosis of the renal cortex, hyponatremia, hypokalemia, Schwartz-Bartter syndrome, disorders of the gastrointestinal tract, gastric vasospasm, hepatocirrhosis, gastric and peptic ulcer, emesis, recurrent emesis during chemotherapy and travel sickness.

The compounds according to the invention can also be used for the treatment of various vasopressin-dependent or oxytocin-dependent complaints that have central nervous system causes or changes in the HPA (hypothalamic pituitary adrenal) axis, for example in case of affective disorders such as depressive disorders and bipolar disorders. Examples in this group are dysthymic disorders, phobias, post-traumatic stress disorders, general anxiety disorders, panic disorders, seasonal depressions and sleep disorders.

Likewise, the compounds according to the invention can be used in the treatment of anxiety disorders and stress-related anxiety disorders, such as, for example, generalised anxiety disorders, phobias, post-traumatic anxiety disorders, panic anxiety disorders, obsessive-compulsive anxiety disorders, acute stress-related anxiety disorders and social phobia. Furthermore, the compounds according to the invention can also be used in the treatment of memory disturbances, Alzheimer disease, psychoses, psychotic disorders, sleep disorders and/or Cushing syndrome.

The present invention also relates to pharmaceutical compositions that contain an effective dose of a compound according to the invention or of a pharmaceutically compatible salt thereof and suitable excipients.

These excipients are selected according to the pharmaceutical form and the desired form of application.

The compounds of general formula I according to the invention or, where applicable, suitable salts of these compounds, can be used for the production of pharmaceutical compositions for oral, sublingual, subcutaneous, intramuscular, intravenous, topical, intratracheal, intranasal, transdermal or rectal administration, and can be administered to animals or humans in standardised forms of administration, mixed with conventional pharmaceutical excipients, for the prophylaxis or treatment of the abovementioned disorders and diseases.

The suitable standardised forms of administration include forms for oral administration, such as tablets, gelatine capsules, powder, granules and solutions or suspensions for oral intake, forms for sublingual, buccal, intratracheal or intranasal administration, aerosols, implants, forms for subcutaneous, intramuscular or intravenous administration and forms for rectal administration.

The compounds according to the invention can be used in creams, ointments or lotions for topical administration.

In order to achieve the desired prophylactic or therapeutic effect, the dose of the basic active constituent can vary between 0.01 and 50 mg per kg body weight per day.

Each single dose can contain 0.05 to 5,000 mg, preferably 1 to 1,000 mg, of the active constituent in combination with a pharmaceutical excipient. This single dose can be administered 1 to 5 times a day, so that a daily dose of 0.5 to 25,000 mg, preferably 1 to 5,000 mg, is administered.

If a solid composition in the form of tablets is prepared, the principal constituent is mixed with a pharmaceutical excipient, such as gelatine, starch, lactose, magnesium stearate, talc, silicon dioxide or the like.

The tablets can be coated with sucrose, a cellulose derivative or another suitable substance or otherwise treated in order to obtain sustained or delayed activity and in order to obtain continuous release of a predetermined quantity of the basic active constituent.

A preparation in the form of gelatine capsules is obtained by means of mixing the active constituent with an extender and incorporating the resulting mixture into soft or hard gelatine capsules.

A preparation in the form of a syrup or elixir or for administration in the form of drops can contain active constituents together with a sweetener that is preferably calorie-free, methylparaben or propylparaben as an antiseptic, a flavouring agent and a suitable colouring substance.

The water-dispersible powders or granules can contain the active constituents, mixed with dispersion agents, wetting agents or suspending agents, such as polyvinylpyrrolidones, as well as sweeteners or taste correctors.

Rectal administration is achieved by means of the use of suppositories that are prepared with bonding agents that liquefy at rectal temperature, for example, cocoa butter or polyethylene glycols. Parenteral administration is effected by the use of aqueous suspensions, isotonic saline solutions or sterile and injectable solutions that contain pharmacologically well-tolerated dispersion agents and/or wetting agents, such as propylene glycol or polyethylene glycol.

The basic active constituent can also be formulated as microcapsules or centrosomes, where suitable, with one or more excipients or additives.

In addition to the compounds of the general formula (I) or their pharmaceutically well-tolerated salts, the compositions according to the invention can contain other basic active constituents that can be useful for treatment of the abovementioned disorders or diseases.

The present invention consequently furthermore relates to pharmaceutical compositions in which a number of basic active constituents are present together, wherein at least one of these is a compound according to the invention.

The compounds according to the invention represent antagonists of the so-called receptors of the vasopressin-oxytocin family. Compounds of this type can be examined in suitable tests that determine the affinity to a receptor, wherein the affinity constant Ki represents a measure of the potency for bonding to the receptor of the compounds, with a smaller value representing greater potency. The compounds according to the invention are, for example, tested for their receptor affinity in the following vasopressin receptor subtype V1b receptor.

Vasopressin V1a Receptor Binding Test

The substances were dissolved in DMSO in a concentration of $10^{-2}$ M and further diluted in DMSO to $10^{-3}$ M to $10^{-9}$ M. These DMSO solutions were diluted 1:10 with a test buffer. In the test batch, the substance concentration was again diluted 1:10.

The binding test was conducted according to the method of Tahara et al. (Tahara A. et al., Brit. J. Pharmacol. 125, 1463-1470 (1998)). In the test batch (0.250 ml), membranes (50 μg protein in an incubation buffer (50 mmol tris, 10 mmol $MgCl_2$, 0.1% BSA adjusted to pH 7.4 with HCl)) of CHO cells were incubated with stably expressed human V1a receptors (preparation V1a clone 5.0, with protease inhibitors, Roche complete Mini # 1836170) with 0.04 nmol 125 iodine AVP (NEX128) in the incubation buffer (total binding) or additionally with increasing concentrations of the test substance (displacement experiment). The non-specific binding was determined with $10^{-6}$ M AVP. Determinations were carried out three times.

After incubation, 60 minutes at room temperature, the free radioligand was filtered off using vacuum filtration (Skatron cell harvester 7000) through Wathman GF/B fibreglass filters, and the filters were transferred to scintillation containers.

The liquid scintillation measurement was made in a Tricarb device, model 2000 or 2200CA (Packard). The conversion of the measured cpm into dpm was carried out with the help of a standard quench series.

The binding parameters were calculated using non-linear regression in SAS. The algorithms of the program work in a manner analogous to the LIGAND evaluation program (Munson P J und Rodbard D, Analytical Biochem. 107, 220-239 (1980)).

For the examples according to the invention, the affinities to the human vasopressin receptor V1b were measured and affinity constants were determined in the above test. The examples 1, 3, 4, 5, 8 and 13 here showed Ki values under 100 nmol.

Vasopressin V1b Receptor Binding Test

The substances were dissolved in DMSO in a concentration of $10^{-2}$ M and further diluted in DMSO to $10^{-3}$ M to $10^{-9}$ M. These DMSO solutions were diluted 1:10 with a test buffer. In the test batch, the substance concentration was again diluted 1:10.

The binding test was conducted according to the method of Tahara et al. (Tahara A. et al., Brit. J. Pharmacol. 125, 1463-1470 (1998)). In the test batch (0.250 ml), membranes (58 μg protein in an incubation buffer) of CHO-K1 cells were incubated with stably expressed human V1b receptors (preparation V1b-3H2, with protease inhibitors, Roche complete Mini # 1836170) with 1.5 nmol $^3$H-AVP (8-Arg-Vasopressin, NET 800) in incubation buffer (50 mmol Tris, 10 mmol $MgCl_2$, 0.1% BSA adjusted to pH 7.4 with HCl) (total binding) or additionally with increasing concentrations of the test substance (displacement experiment). The non-specific binding was determined with $10^{-6}$ M AVP. Determinations were carried out three times.

Incubation buffer: 50 mmol tris, 10 mmol $MgCl_2$, 0.1% BSA adjusted to pH 7.4 with HCl.

After incubation, 60 minutes at room temperature, the free radioligand was filtered off using vacuum filtration (Skatron cell harvester 7000) through Wathman GF/B fibreglass filters, and the filters were transferred to scintillation containers.

The liquid scintillation measurement was made in a Tricarb device, model 2000 or 2200CA (Packard). The conversion of the measured cpm into dpm was carried out with the help of a standard quench series.

The binding parameters were calculated using non-linear regression in SAS. The algorithms of the program work in a manner analogous to the LIGAND evaluation program (Munson P J und Rodbard D, Analytical Biochem. 107, 220-239 (1980)).

For the examples according to the invention, the affinities to the human vasopressin receptor V1b were measured and affinity constants determined in the above test. The examples 2, 6, 10, 16, 17, 23, 24, 26 and 30 here showed Ki values under 100 nmol.

Effect on Vasopressin-Induced Calcium Rise in Cells that Carry a Cloned Human Vasopressin Receptor The functional activity of the test substances was examined on CHO-K1 cells that were transfected in a stable manner with the human V1b receptor. 50,000 cells were sown in each well of a microtitre plate with 96 wells and incubated in a culture medium overnight at 37° C. in a saturated steam atmosphere with 5% $CO_2$. The culture medium consisted of DMEM/Nut Mix F12 with Glutamax I (Invitrogen), 10% foetal calf serum, 100 units/ml penicillin, 100 μg/ml streptomycin and 800 μg/ml Geneticin. The next day, the cells were washed with culture medium and loaded with a fluorescent dye for calcium according to the manufacturer's information ($Ca^{++}$-Plus Assay Kit, Molecular Devices). The cells were loaded in the presence of probenecid (1% by vol). The test substances were diluted with culture medium (end concentration $10^{-10}$ to $10^{-5}$ M) and incubated at room temperature for 15 minutes with the cells, which were loaded with dye. Subsequently, Arg-vasopressin ($10^{-8}$ M) was added and the maximum fluorescence signal was determined with a FLIPR-96 measuring tool (Molecular Devices). Concentration effect curves were prepared with non-linear regression algorithms (GraphPad Prism 3.0). Kb values were calculated from IC50 values according to Cheng and Prusoff (Kb=IC50/1+L/EC50).

In the following, synthetic pathways for the production of the compounds according to the invention are described by way of example.

The production of the oxindoles according to the invention can follow various pathways; this is sketched in the Synthesis Diagrams 1-4. In these synthesis diagrams, the variables have the same meaning as in the general formula (I).

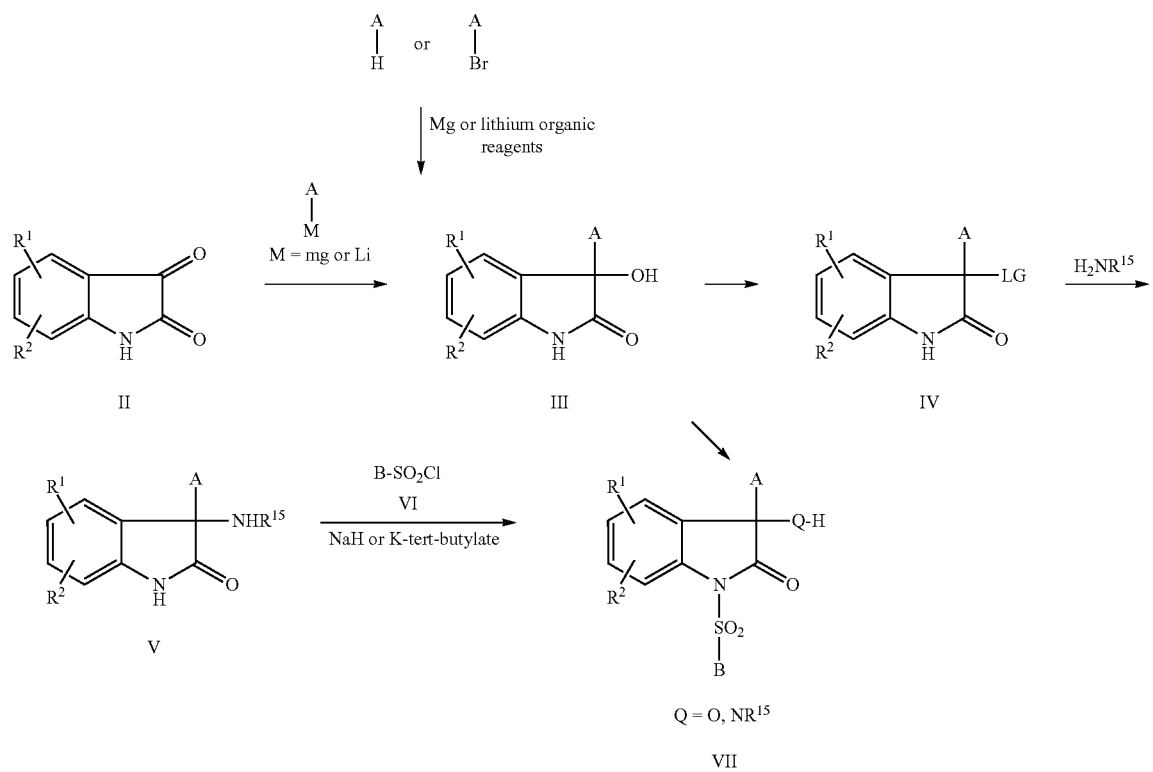

Starting with compounds A-H or A-Br or A-Cl, which are metalated in the customary way, such as, for example, the Grignard compound (Mg) or organyllithium compound, the 3-hydroxy-oxindoles III can be obtained by adding isatin II. The metalated compounds can be obtained in the customary way from halogen or hydrocarbon compounds. Example instructions are contained in Houben-Weil, *Methoden zur Organischen Chemie*, Vol. 13, 1-2, Chap. "*Mg-bzw. Li-Verbindungen*". The isatins II are either available commercially or were produced using methods analogous to those described in the literature (Advances in Heterocyclic Chemistry, A. R. Katritzky and A. J. Boulton, Academic Press, New York, 1975, 18, 2-58; J. Brazil. Chem. Soc. 12, 273-324, 2001).

The 3-hydroxy-oxindoles III can be converted into the compounds IV, which carry a volatile group LG in the 3-position, wherein the volatile group LG can be customary leaving groups, such as halogenides, mesylate or tosylate. Consequently, for example (LG=chlorine), the intermediate product IV can be produced by treating the alcohol III with thionyl chloride in the presence of a base, such as pyridine, for example. Alternatively, alcohols III can be obtained by conversion into the mesylate by means of methane sulfonyl chloride in the presence of a base, such as triethylamine, for example. The compounds IV are subsequently reacted with amines $NH_2R^{15}$, wherein the analogous amines V are obtained. For example, substitution reactions of that kind with amines in the presence of a base such as N,N-diisopropylethylamine can result in the analogous 3-amino-oxindoles V. V can subsequently result in DMF from treatment with sulfonic acid chlorides VI after deprotonation with a strong base, such as potassium-tert-butylate or sodium hydride, and be converted into the product VII. In an analogous way, starting with the alcohols III, the corresponding derivatives VII with Q=O can be obtained.

SYNTHESIS DIAGRAM 2

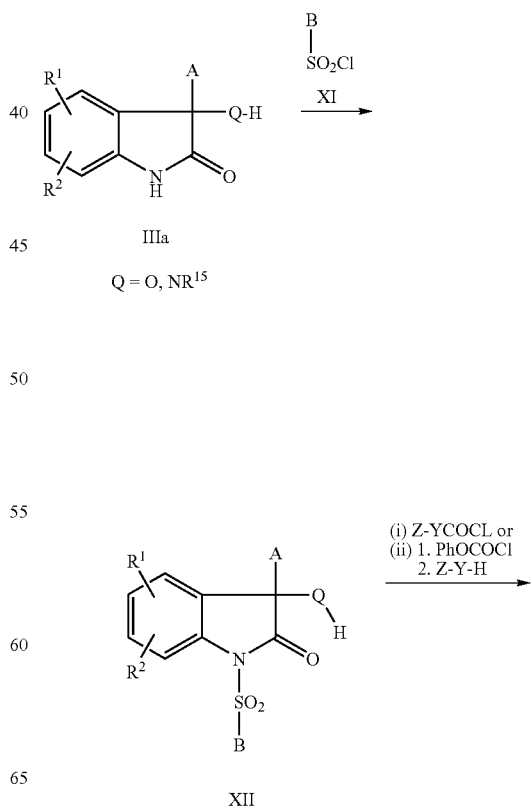

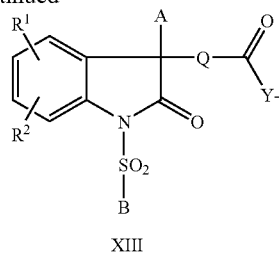

XIII

To produce the compounds XIII according to the invention, the oxindoles IIIa are first converted with sulfonic acid chlorides XI under the conditions already described above. The sulfonic acid chlorides used can be purchased or they can be produced in a way analogous to the known methods (see e.g. J. Med. Chem. 40, 1149 (1997)). The compounds XIII according to the invention are produced in various ways, starting with the sulfonated compounds XII: (i) reaction with carbamoyl chlorides Z—Y—CO—Cl in the presence of a base, such as triethylamine; (ii) activation with chlorocarbonic acid phenylester in the presence of a base, such as pyridine and subsequent reaction with amines Z—Y—H, where necessary at a raised temperature. The amines Z—Y—H can be purchased or they can be produced according to methods known in the literature.

The production of the compounds XXII according to the invention, which carry a functionalised nitrogen atom in the 3-position (e.g., amides, sulfonamides, carbamates and ureas) takes place in a manner analogous to that shown in Synthesis Diagram 2: the 3-amino-oxindoles XII (Q=NR$^{15}$) are converted into the compounds XIII according to the invention by means of reaction with reagents for the derivatization of amino groups, such as carboxylic acids, carboxylic acid chlorides, carboxylic acid anhydrides, sulfonic acid chlorides, chloroformates, isocyanates or carbamoyl chlorides, wherein generally customary methods are used (see J. March, Advanced Organic Chemistry, 1992, 4th edition, Wiley, New York, p. 417-421; 499; 903). Furthermore, the 3-amino group in the compounds XII (Q=NH) can be substituted by treatment with alkylation means, such as alkyl bromides; iodides or mesylates, as well as by reaction with aldehydes or ketones in the presence of reducing agents, such as sodium cyanoborohydride, in the sense of a reductive amination (J. March, Advanced Organic Chemistry, 1992, 4th edition, Wiley, New York, p. 411; 898).

Alternatively, the structural elements XII can be produced according to the two-stage method shown in Synthesis Diagram 3.

SYNTHESIS DIAGRAM 3

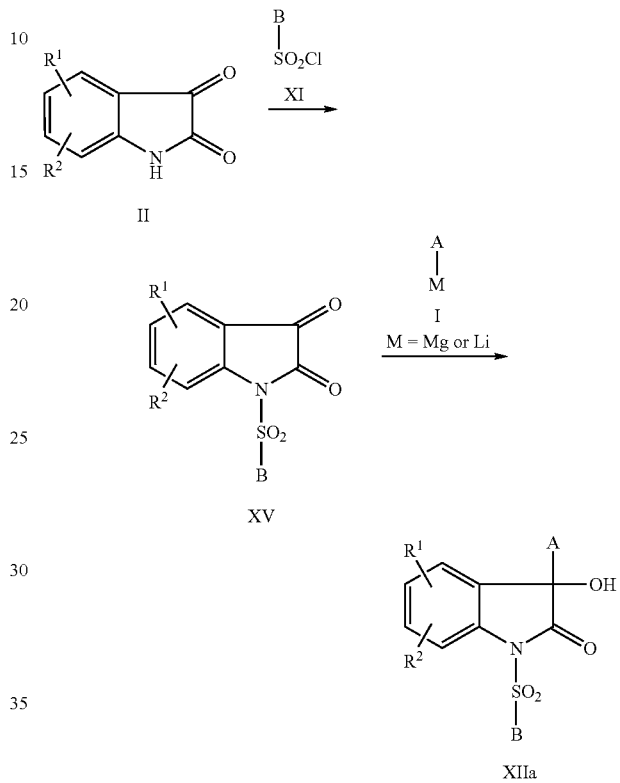

Sulfonated isatins XV are obtained by means of deprotonation of isatins II with a strong base, such as sodium hydride or potassium-tert.-butanolate, followed by treatment with sulfonic acid chlorides XI. The compounds XIIa are obtained in the second step by the addition of metalated compounds I to the 3-keto group of the sulfonyl-isatins XV. The instructions are analogous to the above-described methods.

SYNTHESIS DIAGRAM 4

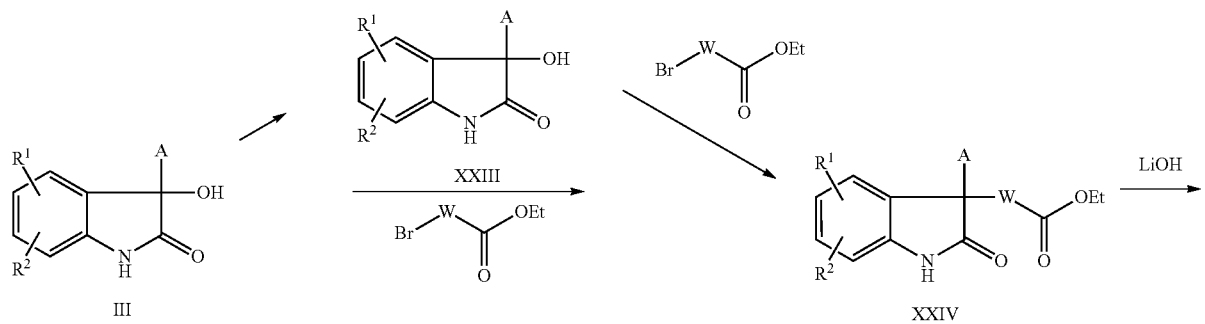

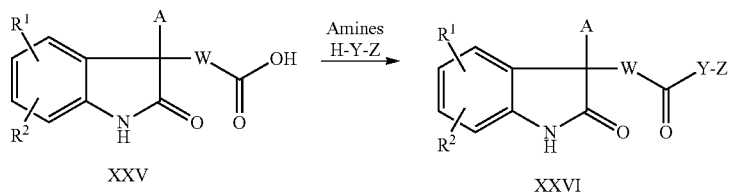
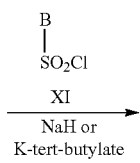

-continued

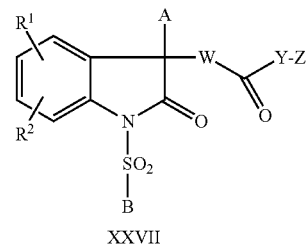

(W = e.g. OCH$_2$, CH$_2$)
(W z.B. = CH$_2$, CH$_2$,)

In Synthesis Diagram 4, pathways to compounds in which W can be varied are sketched. Alcohols III are reacted to the derivatives XXIV with haloacid esters, wherein preferably bromides and chlorides are used, but analogous mesylates or tosylates and similar compounds in which a nucleofuge is present can also be used. The reactions can be carried out in polar solvents, for example, such as DMF or THF, with the addition of basic substances, such as, for example, NaH, potassium-tert.-butanolate, sodium ethanolate, trialkylamines or potassium carbonate, at room temperature or at a raised temperature, such as the boiling temperature of the solvent. The reaction of the indole-2-one XXIII to XXIV is carried out in an analogous manner. The indolones XXIII can be synthetically produced, either from the analogous alcohols III by reduction of the alcohol group, for example, with triethylsilane or in a manner analogous to Mullock, E. B. et al., J. Chem. Soc. C, 1970, 6, 829-833, Ghosal, S. et al., Ind. J. Chem., 1969m 7, 1095-1097 and U.S. Pat. No. 2,759,935. The esters XXIV can be converted into the analogous carboxylic acids XXV with acids, such as HCl and H$_2$SO$_4$, or bases, such as NaOH, KOH or LiOH, wherein solvents are normally used, such as alcohols or THF, with the addition of aqueous acids or bases, at room temperature or at temperatures from 25-70° C. These acids XXV can be converted into the derivatives XXVI by means of reacting the acids with, for example, amines, using customary coupling conditions, as they are cited in, for example, R. C. Larock, *Comprehensive Organic Transformations*, Wiley 1999, Chap. 9. The introduction of the sulfonic acid residue B—SO$_2^-$ takes place in a manner analogous to that described above. Alternatively to Diagram 4, the last two steps can also be carried out in the reverse order.

EXPERIMENTAL SECTION

Example 1

4-(4-Methyl-piperidine-1-yl)-piperazine-1-carboxylic acid-[1-benzenesulfonyl-5-chloro-2-oxo-3-(2-methoxy-phenyl)-2,3-dihydro-1H-indole-3-yl] ester 1a) 5-chloro-3-hydroxy-3-(2-methoxyphenyl)-indole-2-one 40 g (1.65 mol) magnesium shavings were overlaid with 100 ml ether, and after the addition of a small amount of iodine, they were carefully heated until the reaction kicked off. 203 ml (1.65 mol) bromanisole, dissolved in 450 ml ether, were dropped in to the boiling solution so slowly that the reaction continually proceeded at a low boil. Subsequently, with slight cooling to 20° C., 75 g (0.41 mol) 5-chlorisatin in 750 ml water-free tetrahydrofurane were added in by drops. After this, everything was stirred for 30 minutes more at room temperature. The reaction solution was poured into an aqueous NH$_4$Cl solution while being stirred. This aqueous phase was extracted a number of times with ethyl acetate and the combined aqueous phases were washed with water four times, dried and concentrated in a vacuum. The residue obtained was crystallised from isopropanol, wherein 106 g of the intermediate product resulted.

1b) 5-chloro-1-(2,4-dimethoxy-benzenesulfonyl)-3-hydroxy-3-(2-2-methoxy-phenyl)-indole-2-one 2 g (18.1 mmol) potassium-tert.-butanolate were added in portions to 5 g (17.3 mmol) of the intermediate product 1a in 50 ml water-free dimethylformamide and everything was stirred for approximately 60 minutes. Then 3.2 g (18.1 mmol)

benzene sulfonic acid chloride were rapidly added by drops at 0° C. This was then stirred for 2 h at 0° C. and then for 16 h at room temperature. The reaction solution was subsequently poured on to 250 ml icy water/K$_2$CO$_3$ solution, wherein a precipitate arose that was dissolved in methylene chloride. This organic phase was washed with NaCl solution, dried and concentrated in a vacuum. The residue obtained was crystallised from ethanol, wherein 2.8 g of the intermediate product were obtained.

1c) Carbonic acid-[5-chloro-1-(2,4-dimethoxy-benzenesulfonyl)-3-(2-methoxy-phenyl)-2-oxo-2,3-dihydro-1-H-indole-3-yl] ester-phenyl ester 3.3 g (7.7 mmol) of the intermediate product 1b and 4.65 g (46 mmol) triethylamine were dissolved in 30 ml methylene chloride. 4.2 g (26.9 mmol) chloroformic acid phenyl ester were rapidly added by drops at 0° C. This was stirred for 15 minutes more and then the reaction solution was poured into a 5% mixture of potassium carbonate solution and icy water. The aqueous solution was extracted with methyl chloride three times. The combined organic phases were washed with aqueous potassium carbonate solution and an NaCl solution, dried over MgSO$_4$ and concentrated in a vacuum. The residue obtained was treated with a small quantity of methanol, wherein a solid precipitated that was isolated and dried. 3.2 g of the intermediate product were obtained.

1d) 4-(4-Methyl-piperidine-1-yl)-piperazine-1-carboxylic acid-[1-benzenesulfonyl-5-chloro-2-oxo-3-(2-methoxy-phenyl)-2,3-dihydro-1H-indole-3-yl] ester 0.15 g (0.27 mmol) of the intermediate product 1c and 204 mg (1.1 mmol) 1-methylpiperidine-4-yl)-piperazine were mixed for 16 h at room temperature in 5 ml tetrahydrofurane. Then the solvent was removed in a vacuum. The residue was crystallised from 5 ml methanol, wherein 95 mg of the product were obtained.
$^1$H-NMR (D$_6$-DMSO): δ=1.35 (2H), 1.6 (2H), 1.8 (2H), 2.1 (3H), 2.15 (1H), 2.3 (2H), 2.75 (2H), 3.05 (2H), 3.3 (3H), 3.4-3.7 (1H), 6.9 (1H), 7.1 (1H), 7.15 (1H), 7.35 (1H), 7.45 (1H), 7.65 (2H), 7.7-7.9 (3H) and 8.1 (2H) ppm.

Example 2

4-(1-Methyl-piperidine-4-yl)-piperazine-1-carboxylic acid-[1-(2,4-dimethoxy-benzenesulfonyl)-5-methoxy-2-oxo-3-(2-propoxyphenyl)-2,3-dihydro-1H-indole-3-yl] ester 2a) 5-Chloro-3-hydroxy-3-(2-propoxyphenyl)-indole-2-one 3.1 g (0.13 mol) magnesium shavings were overlaid with 20 ml ether, and after the addition of a small quantity of iodine, they were carefully heated until the reaction kicked off. 27.3 g (0.13 mol) 2-propoxy-1-bromobenzene dissolved in 100 ml ether were dropped in to the boiling solution so slowly that the reaction continually proceeded at a low boil. Subsequently, with slight cooling to 20° C., 7.5 g (42 mmol) 5-methoxisatin in 150 ml water-free tetrahydrofurane were added in by drops. After this, everything was stirred for 30 minutes more at room temperature. The reaction solution was poured into an aqueous NH$_4$Cl solution while being stirred. This aqueous phase was extracted a number of times with ethyl acetate and the combined aqueous phases were washed with water four times, dried and concentrated in a vacuum. The residue obtained was crystallised from a small quantity of ethyl acetate, wherein 8.3 g of the intermediate product resulted.

2b) Carbonic acid-[5-methoxy-2-oxo-3-(2-propoxyphenyl)-2,3-dihydro-1-H-indole-3-yl] ester-phenyl ester 1.26 ml (10.1 mmol) chloroformic acid phenyl ester were rapidly added to 3 g (9.6 mmol) of the intermediate product 2a in 50 ml pyridine at 0° C. This was then stirred for 16 h at room temperature. Subsequently, everything was poured into icy water and extracted with ethyl acetate a number of times. The combined organic phases were washed a number of times with water, dried over MgSO$_4$ and concentrated in a vacuum. The residue obtained was treated with a little ether, wherein a solid precipitated that was isolated and dried. 3.4 g of the intermediate product were obtained.

2c) 4-(4-Methyl-piperidine-1-yl)-piperazine-1-carboxylic acid-[5-methoxy-2-oxo-3-(2-propoxy-phenyl)-2,3-dihydro-1H-indole-3-yl] ester 3.3 g (7.6 mmol) of the intermediate product 2b and 5.6 g (30.5 mmol) 1-methylpiperidine-4-yl)-piperazine were stirred for 16 h at room temperature in 100 ml tetrahydrofurane. Then the solvent was removed in a vacuum. The residue was distributed between water and ethyl acetate. The water phase was then washed with ethyl acetate twice. The combined ethyl acetate phases were washed again with water, dried and concentrated in a vacuum. The residue was mixed with ether by stirring, wherein a solid resulted that was isolated. 2.9 g of the intermediate product were obtained.

2d) 4-(1-Methyl-piperidine-4-yl)-piperazine-1-carboxylic acid-[1-(2,4-dimethoxy-benzenesulfonyl)-5-methoxy-2-oxo-3-(2-propoxyphenyl)-2,3-dihydro-1H-indole-3-yl] ester 54 mg (0.48 mmol) of potassium-tert.-butanolate were added in portions to 200 mg (0.38 mmol) of the intermediate product 2c in 5 ml water-free dimethylformamide and everything was stirred for approximately 60 minutes. Then 113 mg (0.48 mmol) 2,4 dimethoxybenzene sulfonic acid chloride were rapidly added by drops at 0° C. This was then stirred for 16 h at room temperature. The reaction solution was subsequently poured on to 1 M NaOH, wherein a precipitate formed that was isolated. This precipitate was dissolved in 1 ml methanol and charged with 1 ml ethereal HCl. This solution was kept overnight at 0° C., wherein a precipitate resulted that was isolated. 213 mg of the product were obtained as dihydrochloride.
$^1$H-NMR (D$_6$-DMSO): δ=0.7 (3H), 1.5 (2H), 2.0 (2H), 2.3 (2H), 2.7 (3H), 2.8-3.7 (18H), 3.8 (2H), 3.85 (3H), 4.3 (1H), 6.6 (3H), 6.0-7.1 (3H), 7.35 (1H), 7.7 (2H), 7.85 (1H) and 10.4-10.8 (N$^+$H, broad) ppm.

Example 3

4-(1-Methyl-piperidine-4-yl)-piperazine-1-carboxylic acid-[1-(2,4-dimethoxy-benzenesulfonyl)-5-chloro-2-oxo-3-(2-methoxyphenyl)-2,3-dihydro-1H-indole-3-yl] amide dihydrochloride 3a) 3,5Dichloro-3-(2-methoxyphenyl)-indole-2-one 38 ml (0.518 mol) thionyl chloride were slowly added by drops to 100 g (0.345 mol) of the intermediate product 1a, 56 ml (0.695 mol) pyridine in 1 l methylene chloride at 0° C., and then stirred for approximately 30 minutes more. Then the reaction mixture was poured on to icy water and the organic phase was separated. This organic phase was then washed with water, dried and concentrated in a vacuum. The residue was treated with toluene a number of times and the organic solvent was removed in a vacuum each time. 79 g of the raw product were obtained and further reacted without further cleaning.

3b) 3-Amino-5-chloro-3-(2-methoxyphenyl)-indole-2-one 10 g (32.45 mmol) of the intermediate product 2a were suspended in 100 ml methylene chloride. After the addition of 100 ml 2-molar ethanol ammonia solution, the reaction mixture was stirred for 16 h. After this, everything was poured on to icy water and the organic phase was separated. The aqueous phase was cooled, wherein a white crystallizate formed, which was isolated. 5.7 g of the product were obtained.

3c) Carbonic acid-[5-chloro-2-oxo-3-(2-methoxyphenyl)-2,3-dihydro-1-H-indole-3-yl] ester-phenyl-amide 0.38 ml (3.1 mmol) chloroformic acid ethyl ester were added to 0.8 g (2.8 mmol) of the intermediate product 3b in 20 ml pyridine at 0° C., and then everything was stirred for 16 h at room temperature. Then the batch was poured on to icy water and extracted with ethyl acetate. The organic phase was washed with water, dried and concentrated in a vacuum. The residue obtained in this way was dissolved in a little ether and the product was precipitated by the careful addition of n-pentane. 1.1 g were obtained.

3d) 4-(4-Methyl-piperidine-1-yl)-piperazine-1-carboxylic acid-(5-chloro-2-oxo-3-phenyl-2,3-dihydro-1H-indole-3-yl)-amide 1 g (2.4 mmol) of the intermediate product 3c and 1.8 g (9.8 mmol) 1(1-Methylpiperidine-4-yl)piperazine were boiled in 35 ml water-free tetrahydrofurane for 3 h with return flow. Then the solvent was removed in a vacuum. The residue obtained was distributed between water and ethyl acetate, the organic phase was separated, washed with water, dried and concentrated in a vacuum. The residue was treated with ether/pentane, after which the product accumulated as a solid. 0.76 g were obtained.

3e) 4-(1-Methyl-piperidine-4-yl)-piperazine-1-carboxylic acid-[1-(2,4-dimethoxy-benzenesulfonyl)-5-chloro-2-oxo-3-(2-methoxyphenyl)-2,3-dihydro-1H-indole-3-yl] amide dihydrochloride 0.052 mg (0.47 mmol) potassium-tert.-butanolate were added to 0.21 g (0.42 mmol) of the intermediate product 3d in 2 ml dimethylformamide at 0° C. Everything was stirred for 1 h at 0° C. After this, 0.11 g (0.47 mmol) 2.4-dimethoxybenzene sulfonic acid chloride was added. After this, the reaction mixture was stirred for 16 h more at room temperature. Then the mixture was poured into a 5% potassium carbonate solution, after which a precipitate slowly formed. This precipitate was isolated and chromatographically cleaned on silica gel (mobile phase: methylene chloride/methanol=1/1). 0.1 g of the product was obtained.

$^1$H-NMR (D$_6$-DMSO): δ=2.0 (2H), 2.3 (2H), 2.7 (3H), 2.8-3.1 (4H), 3.1-3.3 (1H), 3.25-3.7 (2H), 3.3-3.6 (9H), 3.7 (3H), 3.85 (3H), 3.9-4.1 (1H), 6.7 (2H), 6.95 (1H), 7.05 (1H), 7.3 (1H), 7.35 (3H), 7.7 (1H), 7.9 (2H) and 10.5 (N$^+$H, broad) ppm.

The following compounds were produced in a manner analogous to the methodical procedures described in examples 1, 2, 3 and 192:

Example 4

4-(1-Methyl-piperidine-4-yl)-piperazine-1-carboxylic acid-[1-benzenesulfonyl-5-chloro-2-oxo-3-phenyl-2,3-dihydro-1H-indole-3-yl] ester dihydrochloride $^1$H-NMR (D$_6$-DMSO): δ=2.0 (2H), 2.3 (2H), 2.7 (3H), 2.85-3.1 (4H), 3.2-3.7 (8H), 4.25 (1H), 7.15 (2H), 7.35 (3H), 7.55 (1H), 7.6 (3H), 7.8 (1H), 7.9 (1H), 8.0 (1H) and 10.5 (N$^+$H, broad) ppm.

Example 5

4-(4-Methyl-piperazine-1-yl)-piperidine-1-carboxylic acid-[1-benzenesulfonyl-5-chloro-2-oxo-3-phenyl-2,3-dihydro-1H-indole-3-yl] ester $^1$H-NMR (D$_6$-DMSO): δ=1.05 (1H), 1.4 (1H), 1.65 (1H), 1.8 (1H), 2.1 (3H), 2.2-2.5 (8H), 2.65 (1H), 3.0 (1H), 3.5 (2H), 4.1 (1H), 7.1 (2H), 7.35 (3H), 7.45 (1H), 7.55-7.7 (3H), 7.8 (1H), 7.9 (1H) and 7.95 (2H) ppm.

Example 6

4-(1-Methyl-piperidine-4-yl)-piperazine-1-carboxylic acid-[1-(2,4-dimethoxy-benzenesulfonyl)-5-methoxy-2-oxo-3-(2-methoxyphenyl)-2,3-dihydro-1H-indole-3-yl] ester dihydrochloride $^1$H-NMR (D$_6$-DMSO): δ=2.05 (2H), 2.7 (3H), 2.9-3.1 (4H), 3.1-3.3 (2H), 3.3-3.8 (15H), 3.85 (3H), 4.1-4.4 (1H), 6.75 (3H), 6.95 (2H), 7.05 (1H), 7.35 (1H), 7.65 (1H), 7.75 (1H), 7.85 (1H) and 10.5-11 (N$^+$H, broad) ppm.

Example 7

4-(4-Methyl-piperazine-1-yl)-piperidine-1-carboxylic acid-[1-benzenesulfonyl-5-methyl-2-oxo-3-phenyl-2,3-dihydro-1H-indole-3-yl] ester dihydrochloride $^1$H-NMR (D$_6$-DMSO): δ=1.2-1.7 (4H), 1.9-2.2 (2H), 2.3 (3H), 2.6-2.8 (5H), 3.0 (2H), 3.2-3.8 (6H), 4.2 (1H), 7.1 (3H), 7.3 (4H), 7.6 (2H), 7.7 (2H) and 7.9 (2H) ppm.

Example 8

4-(1-Methyl-piperidine-4-yl)-piperazine-1-carboxylic acid-[1-(2,4-dimethoxy-benzenesulfonyl)-5-methoxy-2-oxo-3-(2-methylphenyl)-2,3-dihydro-1H-indole-3-yl] ester dihydrochloride $^1$H-NMR (D$_6$-DMSO): δ=2.05 (2H), 2.3 (2H), 2.45 (3H), 2.7 (3H), 2.9-3.1 (4H), 3.1-3.25 (1H), 3.25-3.7 (10H), 3.75 (3H), 3.85 (3H), 4.1-4.4 (1H), 6.6 (1H), 6.7 (2H), 6.85 (1H), 7.1 (2H), 7.25 (2H), 7.65 (1H), 7.8 (1H) and 10.5 (N$^+$H, broad) ppm.

Example 9

4-(Piperidine-4-yl)-piperazine-1-carboxylic acid-[1-(2,4-dimethoxy-benzene-sulfonyl)-5-methoxy-2-oxo-3-(2-methoxyphenyl)-2,3-dihydro-1H-indole-3-yl] ester $^1$H-NMR (D$_6$-DMSO): δ=1.4 (2H), 1.7 (2H), 2.25-2.4 (3H), 2.55-2.7 (2H), 3.05-3.2 (4H), 3.25-3.4 (2H), 3.45-3.6 (8H), 3.65 (3H), 3.85 (3H), 6.55 (1H), 6.65 (1H), 6.7 (1H), 6.9 (1H), 6.95 (1H), 7.05 (1H), 7.35 (1H), 7.65 (1H), 7.7 (1H) and 7.85 (1H) ppm.

Example 10

4-(1-Methyl-piperidine-4-yl)-piperazine-1-carboxylic acid-[1-(2,4-dimethoxy-benzenesulfonyl)-5-fluoro-2-oxo-3-(2-methoxyphenyl)-2,3-dihydro-1H-indole-3-yl] ester $^1$H-NMR (D$_6$-DMSO): δ=1.2-1.5 (4H), 1.65 (2H), 1.85 (2H), 2.1 (3H), 2.15 (1H), 2.3 (2H), 2.75 (2H), 3.2 (2H), 3.5 (2H), 3.55 (3H), 3.6 (3H), 3.85 (3H), 6.65 (1H), 6.7 (1H), 6.95 (1H), 7.0 (1H), 7.1 (1H), 7.2 (1H), 7.4 (1H), 7.7 (1H), 7.75 (1H) and 7.85 (1H) ppm.

Example 11

4-(1-Methyl-piperidine-4-yl)-piperazine-1-carboxylic acid-[1-(2-cyano-benzenesulfonyl)-5-methoxy-2-oxo-3-(2-methylphenyl)-2,3-dihydro-1H-indole-3-yl] ester dihydrochloride $^1$H-NMR (D$_6$-DMSO): δ=2.0 (2H), 2.3 (2H), 2.4 (3H), 2.7 (3H), 2.8-3.1 (4H), 3.2-3.7 (8H), 3.8 (3H), 4.1-4.4 (1H), 6.8 (1H), 6.9 (1H), 7.1 (2H), 7.2-7.4 (3H), 7.8-8.0 (3H), 8.1 (1H), 8.2 (1H) and 10.5 (N$^+$H, broad) ppm.

Example 12

4-(1-Methyl-piperidine-4-yl)-piperazine-1-carboxylic acid-[1-(4-bromo-2-methyl-benzenesulfonyl)-5-methoxy-2-oxo-3-(2-methylphenyl)-2,3-dihydro-1H-indole-3-yl] ester dihydrochloride $^1$H-NMR (D$_6$-DMSO): δ=2.0 (2H), 2.3 (2H), 2.5 (6H), 2.7 (3H), 2.9-3.1 (4H), 3.1-3.25 (1H), 3.25-3.7 (6H), 3.75 (3H), 3.8 (1H), 4.1-4.4 (1H), 6.7 (1H), 6.9 (1H), 7.15 (2H), 7.25 (1H), 7.1-7.3 (3H), 7.95 (1H) and 10.5 (N$^+$H, broad) ppm.

Example 13

4-(1-Benzyl-piperidine-4-yl)-piperazine-1-carboxylic acid-[1-(2,4-dimethoxy-benzenesulfonyl)-5-methoxy-2-oxo-3-(2-methoxyphenyl)-2,3-dihydro-1H-indole-3-yl] ester $^1$H-NMR (D$_6$-DMSO): δ=1.4 (2H), 1.65 (2H), 1.9 (2H), 2.1-2.4 (3H), 2.8 (2H), 3.2 (2H), 3.25-3.4 (2H), 3.4 (2H), 3.45-3.6 (8H), 3.65 (3H), 3.85 (3H), 6.6 (1H), 6.65 (2H), 6.9 (1H), 6.95 (1H), 7.05 (1H), 7.2-7.4 (6H), 7.6 (1H), 7.65 (1H) and 7.85 (1H) ppm.

Example 14

4-(1-Methyl-piperidine-4-yl)-piperazine-1-carboxylic acid-[1-(2,4-dimethoxy-benzenesulfonyl)-5-methyl-2-oxo-3-(2-methylphenyl)-2,3-dihydro-1H-indole-3-yl] ester dihydrochloride $^1$H-NMR (D$_2$O): δ=2.0 (2H), 2.25 (3H), 2.3 (3H), 2.4 (2H), 2.85 (3H), 3.1 (2H), 3.25 (3H), 3.25-3.5 (5H), 3.55 (2H), 3.65 (2H), 3.8 (3H), 3.8-4.1 (2H), 6.45 (1H), 6.65 (1H), 6.75 (1H), 7.05 (1H), 7.1 (1H), 7.2-7.4 (4H), 7.6 (1H) and 7.95 (1H) ppm.

Example 15

4-(1-Methyl-piperidine-4-yl)-piperazine-1-carboxylic acid-[1-(2,4-dimethoxy-benzenesulfonyl)-5-cyano-2-oxo-3-(2-methylphenyl)-2,3-dihydro-1H-indole-3-yl] ester dihydrochloride $^1$H-NMR (D$_2$O): δ=1.9 (2H), 2.3 (3H), 2.4 (2H), 2.8 (3H), 3.1 (2H), 3.3 (3H), 3.3-3.5 (4H), 3.5-3.8 (6H), 3.8 (3H), 3.8-4.1 (1H), 6.45 (1H), 6.65 (1H), 6.7 (1H), 7.1 (1H), 7.2-7.4 (2H), 7.7 (1H) and 7.9-8.0 (3H) ppm.

Example 16

4-(1-Methyl-piperidine-4-yl)-piperazine-1-carboxylic acid-[1-(2,4-dimethoxy-benzenesulfonyl)-5-methoxy-2-oxo-3-(2-methoxyphenyl)-2,3-dihydro-1H-indole-3-yl] amide dihydrochloride $^1$H-NMR (D$_2$O): δ=1.95 (2H), 2.4 (2H), 2.85 (3H), 3.1 (2H), 3.2-3.4 (4H), 3.4 (3H), 3.55 (2H), 3.6 (3H), 3.6-3.8 (8H), 3.85 (3H), 6.6 (1H), 6.7 (1H), 6.8-6.95 (4H), 7.0 (1H), 7.35 (1H), 7.6 (1H) and 8.0 (1H) ppm.

Example 17

4-(1-Methyl-piperidine-4-yl)-piperazine-1-carboxylic acid-[1-(2,4-dimethoxy-benzenesulfonyl)-5-methyl-2-oxo-3-(2-methoxyphenyl)-2,3-dihydro-1H-indole-3-yl] ester dihydrochloride $^1$H-NMR (D$_2$O): δ=1.9 (2H), 2.1 (3H), 2.4 (2H), 2.8 (3H), 3.1 (2H), 3.25 (2H), 3.35 (2H), 3.4 (3H), 3.5 (2H), 3.7 (3H), 3.75 (1H), 3.8 (3H), 3.9-4.1 (2H), 6.65 (1H), 6.7 (1H), 6.95 (1H), 7.0 (1H), 7.1 (1H), 7.2 (1H), 7.4 (1H), 7.6 (1H), 7.8 (1H) and 8.0 (1H) ppm.

Example 18

4-(1-Methyl-piperidine-4-yl)-piperazine-1-carboxylic acid-[1-(2,4-dimethoxy-benzenesulfonyl)-5-methoxy-2-oxo-3-(2-isopropylphenyl)-2,3-dihydro-1H-indole-3-yl] ester dihydrochloride $^1$H-NMR (D$_6$-DMSO): δ=1.1 (3H), 1.2 (3H), 2.05 (2H), 2.3 (2H), 2.7 (3H), 2.8-3.1 (4H), 3.2-4.0 (15H), 4.1-4.4 (1H), 6.4 (1H), 6.5 (1H), 6.65 (1H), 6.85-7.0 (1H), 7.1 (1H), 7.35 (1H), 7.5 (1H), 7.6 (2H), 7.85 (1H) and 10.5 (N$^+$H, broad) ppm.

Example 19

4-(1-Methyl-piperidine-4-yl)-piperazine-1-carboxylic acid-[1-(4-methoxy-benzenesulfonyl)-5-methoxy-2-oxo-3-(2-isopropylphenyl)-2,3-dihydro-1H-indole-3-yl] ester dihydrochloride $^1$H-NMR (D$_6$-DMSO): δ=1.1 (3H), 1.2 (3H), 2.0 (2H), 2.3 (2H), 2.7 (3H), 2.8-3.1 (4H), 3.1-3.7 (8H), 3.7 (1H), 3.75 (1H), 3.8 (3H), 4.1-4.4 (1H), 6.45 (1H), 6.9 (1H), 6.95-7.15 (4H), 7.35 (1H), 7.5 (1H), 7.75 (1H), 7.8 (2H) and 10.5 (N$^+$H, broad) ppm.

Example 20

4-(1-Methyl-piperidine-4-yl)-piperazine-1-carboxylic acid-[1-(3,4-dimethoxy-benzenesulfonyl)-5-methoxy-2-oxo-3-(2-isopropylphenyl)-2,3-dihydro-1H-indole-3-yl] ester dihydrochloride $^1$H-NMR (D$_6$-DMSO): δ=1.2 (3H), 1.25 (3H), 2.0 (2H), 2.3 (2H), 2.7 (3H), 2.8-3.1 (4H), 3.2-3.7 (8H), 3.65 (3H), 3.7 (3H), 3.8 (3H), 3.9 (1H), 4.1-4.4 (1H), 6.35 (1H), 6.9 (1H), 7.0 (1H), 7.1 (2H), 7.25 (1H), 7.35 (1H), 7.5 (2H), 7.7 (1H) and 10.4 (N$^+$H, broad) ppm.

Example 21

4-(1-Methyl-piperidine-4-yl)-piperazine-1-carboxylic acid-[1-(4-isopropyl-benzenesulfonyl)-5-methoxy-2-oxo-3-(2-isopropylphenyl)-2,3-dihydro-1H-indole-3-yl] ester dihydrochloride $^1$H-NMR (D$_6$-DMSO): δ=1.1 (6H), 1.2 (6H), 2.0 (2H), 2.3 (2H), 2.7 (3H), 2.8-3.1 (4H), 3.2-3.70 (13H), 3.8 (3H), 4.1-4.3 (1H), 6.45 (1H), 6.9 (1H), 7.0 (1H), 7.1 (1H), 7.3-7.5 (3H), 7.5 (1H), 7.7-7.9 (3H) and 10.6 (N$^+$H, broad) ppm.

Example 22

4-(1-Methyl-piperidine-4-yl)-piperazine-1-carboxylic acid-[1-(2-cyano-benzenesulfonyl)-5-methoxy-2-oxo-3-(2-isopropylphenyl)-2,3-dihydro-1H-indole-3-yl] ester dihydrochloride $^1$H-NMR (D$_6$-DMSO): δ=1.05 (3H), 1.2 (3H), 2.0 (2H), 2.3 (2H), 2.7 (3H), 2.8-3.1 (4H), 3.2-3.75 (9H), 3.7 (3H), 3.8 (3H), 4.1-4.4 (1H), 6.6 (1H), 6.9 (1H), 7.05 (1H), 7.15 (1H), 7.35 (1H), 7.45 (1H), 7.9 (3H), 8.0 (1H), 8.15 (1H) and 10.5 (N$^+$H, broad) ppm.

Example 23

4-(1-Methyl-piperidine-4-yl)-piperazine-1-carboxylic acid-[1-(2,4-dimethoxy-benzenesulfonyl)-2-oxo-3-(2-methoxyphenyl)-2,3-dihydro-1H-indole-3-yl] ester dihydrochloride $^1$H-NMR (D$_2$O): δ=1.9 (2H), 2.4 (2H), 2.8 (3H), 3.1 (2H), 3.25 (2H), 3.4 (3H), 3.4-3.6 (4H), 3.6 (3H), 3.7 (1H), 3.85 (3H), 3.9-4.1 (2H), 6.65 (1H), 6.7 (1H), 6.9 (1H), 7.1 (3H), 7.4 (2H), 7.7 (1H), 7.8 (1H) and 8.0 (1H) ppm.

Example 24

4-(1-Methyl-piperidine-4-yl)-piperazine-1-carboxylic acid-[1-(2,4-dimethoxy-benzenesulfonyl)-5-methoxy-2-oxo-3-(2-isopropoxyphenyl)-2,3-dihydro-1H-indole-3-yl] ester dihydrochloride $^1$H-NMR (D$_6$-DMSO): δ=0.75 (3H), 1.2 (3H), 2.0 (2H), 2.3 (2H), 2.7 (3H), 2.8-3.1 (6H), 3.1-3.3 (6H), 3.4-3.65 (9H), 3.7 (3H), 3.8 (3H), 4.3 (1H), 4.6 (1H), 6.6 (1H), 6.65 (2H), 7.35 (1H), 7.0 (2H), 7.3 (1H), 7.7 (2H), 7.8 (1H), 10.5-11 (N$^+$H, broad) ppm.

Example 25

4-(1-Methyl-piperidine-4-yl)-piperazine-1-carboxylic acid-[1-(2-cyano-benzenesulfonyl)-5-methoxy-2-oxo-3-(2-isopropoxyphenyl)-2,3-dihydro-1H-indole-3-yl] ester dihydrochloride $^1$H-NMR (D$_6$-DMSO): δ=0.7 (3H), 1.2 (3H), 2.0 (2H), 2.25 (2H), 2.7 (3H), 2.9-3.2 (6H), 3.2-3.6 (6H), 3.65 (3H), 4.3 (1H), 4.6 (1H), 6.6 (1H), 7.0 (2H), 7.35 (1H), 7.75 (1H), 7.8-8.0 (3H), 8.1 (1H), 8.2 (1H), 10.5-11 (N$^+$H, broad) ppm.

Example 26

4-(1-Methyl-piperidine-4-yl)-piperazine-1-carboxylic acid-[1-(2-methoxy-4-methyl-benzene)-sulfonyl-5-methoxy-2-oxo-3-(2-isopropoxyphenyl)-2,3-dihydro-1H-indole-3-yl] ester dihydrochloride $^1$H-NMR (D$_6$-DMSO): δ=0.7 (3H), 1.2 (3H), 2.0 (2H), 2.3 (2H), 2.4 (3H), 2.7 (3H), 2.8-3.0 (4H), 3.0-3.3 (4H), 3.3-3.6 (9H), 3.7 (3H), 4.3 (1H), 4.5 (1H), 6.55 (1H), 6.9 (1H), 7.0 (4H), 7.35 (1H), 7.7-7.8 (3H), 10.5-11 (N$^+$H, broad) ppm.

Example 27

4-(1-Methyl-piperidine-4-yl)-piperazine-1-carboxylic acid-[1-(2-methyl-benzenesulfonyl)-5-methoxy-2-oxo-3-(2-isopropylphenyl)-2,3-dihydro-1H-indole-3-yl] ester dihydrochloride $^1$H-NMR (D$_6$-DMSO): δ=1.1 (3H), 1.2 (3H), 2.0 (2H), 2.3 (2H), 2.4 (3H), 2.7 (3H), 2.9-4.1 (4H), 3.1-3.3 (2H), 3.3-3.9 (12H), 4.1-4.3 (1H), 6.5 (1H), 6.95 (1H), 7.0 (1H), 7.05 (1H), 7.3-7.45 (3H), 7.5 (1H), 7.6 (1H), 7.7 (1H), 8.05 (1H), 10.5-11 (N$^+$H, broad) ppm.

Example 28

4-(1-Methyl-piperidine-4-yl)-piperazine-1-carboxylic acid-[1-(2-methyl-benzenesulfonyl)-5-methoxy-2-oxo-3-(2-isopropoxyphenyl)-2,3-dihydro-1H-indole-3-yl] ester dihydrochloride $^1$H-NMR (D$_6$-DMSO): δ=0.7 (3H), 1.2 (3H), 2.0 (2H), 2.3 (2H), 2.6 (3H), 2.7 (3H), 2.9-3.1 (4H), 3.1-3.3 (2H), 3.3-3.7 (6H), 3.7 (3H), 4.3 (1H), 4.6 (1H), 6.6 (1H), 7.0 (3H), 7.3 (1H), 7.4 (2H), 7.6 (1H), 7.75 (2H), 8.1 (1H), 10.5-11 (N$^+$H, broad) ppm.

Example 29

4-(1-Methyl-piperidine-4-yl)-piperazine-1-carboxylic acid-[1-(2-methyl-benzenesulfonyl)-5-methoxy-2-oxo-3-(2-ethoxyphenyl)-2,3-dihydro-1H-indole-3-yl] ester dihydrochloride $^1$H-NMR (D$_6$-DMSO): δ=1.0 (3H), 2.0 (2H), 2.3 (2H), 2.6 (3H), 2.7 (3H), 2.95 (2H), 3.0-3.3 (2H), 3.3-3.7 (8H), 3.7 (3H), 3.75 (1H), 3.9 (1H), 4.3 (1H), 6.7 (1H), 7.0 (2H), 7.05 (1H), 7.35 (1H), 7.45 (2H), 7.60 (1H), 7.65 (1H), 7.7 (1H), 8.1 (1H), 10.3-10.8 (N$^+$H, broad) ppm.

Example 30

4-(1-Methyl-piperidine-4-yl)-piperazine-1-carboxylic acid-[1-(2,4-dimethoxy-benzenesulfonyl)-5-methoxy-2-oxo-3-(2-ethoxyphenyl)-2,3-dihydro-1H-indole-3-yl] ester dihydrochloride $^1$H-NMR (D$_6$-DMSO): δ=1.05 (3H), 2.0 (2H), 2.3 (2H), 2.7 (3H), 2.8-3.25 (6H), 3.3-3.7 (9H), 3.7 (3H), 3.75 (1H), 3.85 (3H), 3.9 (1H), 4.3 (1H), 6.6-6.7 (3H), 6.95 (2H), 7.05 (1H), 7.35 (1H), 7.7 (2H), 7.75 (1H) and 10.3-10.8 (N$^+$H, broad) ppm.

Example 31

4-(1-Methyl-piperidine-4-yl)-piperazine-1-carboxylic acid-[1-(2-methyl-benzenesulfonyl)-5-methoxy-2-oxo-3-(2-methoxyphenyl)-2,3-dihydro-1H-indole-3-yl] ester dihydrochloride $^1$H-NMR (D$_2$O): δ=1.9 (2H), 2.4 (2H), 2.6 (3H), 2.85 (3H), 3.1 (2H), 3.2-3.7 (15H), 3.9 (1H), 4.1 (1H), 6.7 (1H), 6.95 (2H), 7.1 (1H), 7.4 (1H), 7.45 (2H), 7.65 (1H), 7.7 (1H), 7.8 (1H) and 8.2 (1H) ppm.

Example 32

4-(1-Methyl-piperidine-4-yl)-piperazine-1-carboxylic acid-[1-(3-cyano-benzenesulfonyl)-5-methoxy-2-oxo-3-(2-ethoxyphenyl)-2,3-dihydro-1H-indole-3-yl] ester dihydrochloride $^1$H-NMR (D$_6$-DMSO): δ=1.1 (3H), 2.1 (2H), 2.3 (2H), 2.7 (3H), 2.8-3.1 (4H), 3.1-3.3 (2H), 3.3-3.65 (6H), 3.65 (3H), 3.8 (1H), 3.9 (1H), 4.3 (1H), 6.65 (1H), 6.95 (2H), 7.05 (1H), 7.35 (1H), 7.75 (1H), 7.8 (1H), 7.85 (1H), 8.25 (1H), 8.3 (1H), 8.35 (1H) and 10.5-11 (N$^+$H, broad) ppm.

Example 33

4-(1-Methyl-piperidine-4-yl)-piperazine-1-carboxylic acid-[1-(4-ethyl-benzenesulfonyl)-5-methoxy-2-oxo-3-(2-ethoxyphenyl)-2,3-dihydro-1H-indole-3-yl] ester dihydrochloride $^1$H-NMR (D$_6$-DMSO): δ=1.0 (3H), 1.2 (3H), 2.0 (2H), 2.3 (2H), 2.7 (3H), 2.9-3.1 (4H), 3.1-3.3 (2H), 3.3-3.9 (13H), 4.3 (1H), 6.6 (1H), 6.95 (2H), 7.05 (1H), 7.4 (1H), 7.5 (2H), 7.7 (1H), 7.8 (1H), 7.9 (2H) and 10.5-11 (N$^+$H, broad) ppm.

Example 34

4-(1-Methyl-piperidine-4-yl)-piperazine-1-carboxylic acid-[1-(2-methyl-benzenesulfonyl)-5-methoxy-2-oxo-3-(2-propoxyphenyl)-2,3-dihydro-1H-indole-3-yl] ester dihydrochloride $^1$H-NMR (D$_6$-DMSO): δ=0.7 (3H), 1.9 (2H), 2.05 (2H), 2.3 (2H), 2.6 (3H), 2.7 (3H), 2.7-3.7 (15H), 3.7-3.9 (2H), 4.3 (1H), 6.7 (1H), 6.95 (2H), 7.05 (1H), 7.35 (1H), 7.4 (2H), 7.6 (1H), 7.65 (1H), 7.75 (1H), 8.1 (1H), and 10.5-11 (N$^+$H, broad) ppm.

Example 35

4-(1-Methyl-piperidine-4-yl)-piperazine-1-carboxylic acid-[1-(2-methoxy-4-methyl-benzenesulfonyl)-5-methoxy-2-oxo-3-(2-propoxyphenyl)-2,3-dihydro-1H-indole-3-yl] ester dihydrochloride $^1$H-NMR (D$_6$-DMSO): δ=0.7 (3H), 1.5 (2H), 2.0 (2H), 2.3 (2H), 2.4 (3H), 2.7 (3H), 2.9-3.7 (19H), 3.8 (1H), 4.3 (1H), 6.6 (1H), 6.7-7.1 (5H), 7.35 (1H), 7.7 (2H), 7.8 (1H) and 10.5-11 (N$^+$H, broad) ppm.

Example 36

4-(1-Methyl-piperidine-4-yl)-piperazine-1-carboxylic acid-[1-benzenesulfonyl-5-methyl-2-oxo-3-phenyl-2,3-dihydro-1H-indole-3-yl] ester dihydrochloride $^1$H-NMR (D$_6$-DMSO): δ=2.0 (2H), 2.2-2.4 (2H), 2.3 (3H), 2.7 (1H), 2.75 (3H), 2.9-3.8 (11H), 4.2 (1H), 7.1 (2H), 7.15 (1H), 7.3-7.5 (4H), 7.6 (2H), 7.75 (2H) and 8.0 (2H) ppm.

Example 37

4-(1-Methyl-piperidine-4-yl)-piperazine-1-carboxylic acid-[1-(2,4-dimethoxy-benzenesulfonyl)-5-methoxy-2-oxo-3-(2-ethylphenyl)-2,3-dihydro-1H-indole-3-yl] ester dihydrochloride $^1$H-NMR (D$_2$O): δ=1.1 (3H), 1.95 (2H), 2.4 (2H), 2.75 (1H), 2.8-3.0 (4H), 3.1 (2H), 3.15 (3H), 3.2-3.5 (4H), 3.5-3.65 (4H), 3.65-3.75 (8H), 3.8-4.1 (3H), 6.35 (1H), 6.5 (1H), 6.6 (1H), 6.7 (1H), 6.9 (1H), 7.1 (1H), 7.3 (1H), 7.4 (1H), 7.6 (1H) and 7.9 (1H) ppm.

Example 38

4-(1-Methyl-piperidine-4-yl)-piperazine-1-carboxylic acid-[1-(2,4-dimethoxy-benzenesulfonyl)-5-methoxy-2-oxo-3-(2,5-dimethoxyphenyl)-2,3-dihydro-1H-indole-3-yl] ester dihydrochloride $^1$H-NMR (D$_2$O): δ=1.9-2.1 (2H), 2.4 (2H), 2.9 (3H), 3.1 (2H), 3.2-3.6 (11H), 3.65 (3H), 3.7 (3H), 3.8 (3H), 3.9 (3H), 3.9-4.2 (3H), 6.65 (1H), 6.7 (1H), 6.75 (1H), 6.95 (1H), 7.0 (2H), 7.3 (1H), 7.6 (1H) and 8.0 (1H) ppm.

Example 39

4-(1-Methyl-piperidine-4-yl)-piperazine-1-carboxylic acid-[1-(2-methyl-benzenesulfonyl)-5-methoxy-2-oxo-3-(2,5-dimethoxyphenyl)-2,3-dihydro-1H-indole-3-yl] ester dihydrochloride $^1$H-NMR (D$_2$O): δ=1.9-2.1 (2H), 2.4-2.6 (2H), 2.7 (3H), 2.9 (3H), 3.1-3.3 (2H), 3.3 (1H), 3.3-3.6 (7H), 3.6-3.75 (4H), 3.8 (3H), 3.9 (3H), 3.9-4.2 (2H), 6.9 (1H), 7.0 (1H), 7.1 (2H), 7.45 (1H), 7.5 (2H), 7.7 (1H), 7.8 (1H) and 8.3 ppm.

Example 40

4-(1-Methyl-piperidine-4-yl)-piperazine-1-carboxylic acid-[1-(benzenesulfonyl)-5-methoxy-2-oxo-3-(2,5-dimethoxyphenyl)-2,3-dihydro-1H-indole-3-yl] ester dihydrochloride $^1$H-NMR (D$_2$O): δ=1.95 (2H), 2.4 (2H), 2.85 (3H), 3.1 (2H), 3.2 (3H), 3.2-3.6 (7H), 3.65 (3H), 3.7 (2H), 3.75 (3H), 3.8-4.2 (2H), 6.75 (1H), 6.8 (1H), 6.95 (2H), 7.3 (1H), 7.6 (2H), 7.75 (2H) and 8.1 (2H) ppm.

Example 41

4-(1-Methyl-piperidine-4-yl)-piperazine-1-carboxylic acid-[1-(4-cyano-1-benzenesulfonyl)-5-chloro-2-oxo-3-(2-ethoxyphenyl)-2,3-dihydro-1H-indole-3-yl] ester $^1$H-NMR (CDCl$_3$): δ=1.3 (3H), 1.5-1.7 (2H), 1.7 (2H), 1.9 (2H), 2.2-2.35 (4H), 2.4 (2H), 2.5 (2H), 2.8-3.05 (4H), 3.55 (2H), 3.8 (1H), 4.0 (1H), 6.8 (1H), 6.95 (1H), 7.0 (1H), 7.25-7.35 (2H), 7.7 (1H), 7.75 (2H), 7.9 (1H) and 8.2 (1H) ppm.

Example 42

4-(1-Methyl-piperidine-4-yl)-piperazine-1-carboxylic acid-[1-(2-methoxy-1-benzenesulfonyl)-5-chloro-2-oxo-3-(2-ethoxyphenyl)-2,3-dihydro-1H-indole-3-yl] ester $^1$H-NMR (CDCl$_3$): δ=1.25 (3H), 1.55 (2H), 1.7 (2H), 1.9 (2H), 2.2-2.9 (6H), 2.5 (2H), 2.9 (2H), 3.05 (2H), 3.55 (5H), 3.8 (1H), 4.05 (1H), 6.8 (1H), 6.9-7.1 (4H), 7.25-7.35 (2H), 7.5 (1H), 7.65 (1H), 7.95 (1H) and 8.15 (1H) ppm.

Example 43

4-(1-Methyl-piperidine-4-yl)-piperazine-1-carboxylic acid-[1-(2-methoxy-4-methyl-1-benzenesulfonyl)-5-chloro-2-oxo-3-(2-ethoxyphenyl)-2,3-dihydro-1H-indole-3-yl] ester $^1$H-NMR (CDCl$_3$): δ=1.25 (3H), 1.55 (2H), 1.7 (2H), 1.9 (2H), 2.2-2.6 (11H), 2.9 (2H), 3.1 (2H), 3.6 (5H), 3.8 (1H), 4.05 (1H), 6.7 (1H), 6.8 (1H), 6.85 (1H), 6.95 (2H), 7.3 (2H), 7.65 (1H), 7.95 (1H) and 8.0 (1H) ppm.

Example 44

4-(1-Methyl-piperidine-4-yl)-piperazine-1-carboxylic acid-[1-benzenesulfonyl-5-chloro-2-oxo-3-(2-ethoxyphenyl)-2,3-dihydro-1H-indole-3-yl] ester $^1$H-NMR (CDCl$_3$): δ=1.25 (3H), 1.55 (2H), 1.75 (2H), 1.9 (2H), 2.25 (4H), 2.3 (2H), 2.5 (2H), 2.9 (2H), 3.0 (2H), 3.55 (2H), 3.8 (1H), 4.0 (1H), 6.8 (1H), 6.9 (1H), 7.0 (1H), 7.3 (2H), 7.5 (2H), 7.6 (1H), 7.7 (1H), 7.9 (1H) and 8.1 (1H) ppm.

Example 45

4-(1-Methyl-piperidine-4-yl)-piperazine-1-carboxylic acid-[1-(2,4-dimethoxy-1-benzenesulfonyl)-5-chloro-2-oxo-3-(2-ethoxyphenyl)-2,3-dihydro-1H-indole-3-yl] ester $^1$H-NMR (CDCl$_3$): δ=1.25 (3H), 1.6 (2H), 1.7 (2H), 1.95 (2H), 2.3 (4H), 2.3 (2H), 2.35 (2H), 2.55 (2H), 2.9 (2H), 3.1 (2H), 3.5-3.65 (5H), 3.8 (1H), 3.85 (3H), 4.05 (1H), 6.4 (1H), 6.5 (2H), 6.8 (1H), 6.9-7.0 (2H), 7.3 (2H), 7.65 (1H), 7.9 (1H) and 8.05 (1H) ppm.

Example 46

4-(1-Methyl-piperidine-4-yl)-piperazine-1-carboxylic acid-[1-(2,4-dimethoxy-1-benzenesulfonyl)-5-chloro-2-oxo-3-(2-methoxyphenyl)-2,3-dihydro-1H-indole-3-yl] ester dihydrochloride $^1$H-NMR (D$_6$-DMSO): δ=2.05 (2H), 2.3 (2H), 2.65-2.8 (3H), 2.9-3.7 (18H), 3.9 (3H), 4.3 (1H), 6.7 (2H), 7.0 (1H), 7.1 (1H), 7.1 (1H), 7.4 (1H), 7.45 (1H), 7.8 (1H), 7.9 (1H), 10.6 (N$^+$–H) and 11.7 (N$^+$–H) ppm.

Example 47

4-(1-Methyl-piperidine-4-yl)-piperazine-1-carboxylic acid-[1-(2-methoxy-4-methyl-1-benzenesulfonyl)-5-chloro-2-oxo-3-(2-ethoxyphenyl)-2,3-dihydro-1H-indole-3-yl] amide $^1$H-NMR (CDCl$_3$): δ=1.5 (3H), 1.6 (2H), 1.75 (2H), 1.95 (2H), 2.25 (4H), 2.35 (3H), 2.45 (4H), 2.9 (2H), 3.2 (4H), 3.55 (3H), 4.1-4.3 (2H), 6.7 (1H), 6.8-7.0 (5H), 7.25 (2H), 7.3 (1H), 7.85 (1H) and 8.0 (1H) ppm.

Example 48

4-(1-Methyl-piperidine-4-yl)-piperazine-1-carboxylic acid-[1-(2,4,6-trimethyl-1-benzenesulfonyl)-5-chloro-2-oxo-3-(2-ethoxyphenyl)-2,3-dihydro-1H-indole-3-yl] ester $^1$H-NMR (CDCl$_3$): δ=1.15 (3H), 1.6 (2H), 1.7 (2H), 1.9 (2H), 2.2-2.3 (7H), 2.4 (2H), 2.5 (2H), 2.7 (6H), 2.9 (2H), 3.1 (1H), 3.35 (1H), 3.55 (1H), 3.6 (1H), 3.85 (1H), 4.05 (1H), 6.8 (1H), 6.9 (2H), 7.0 (2H), 7.2-7.3 (2H), 7.65 (1H) and 7.95 (1H) ppm.

Example 49

4-(1-Methyl-piperidine-4-yl)-piperazine-1-carboxylic acid-[1-(2,4-dichloro-1-benzenesulfonyl)-5-methoxy-2-oxo-3-(2-ethoxyphenyl)-2,3-dihydro-1H-indole-3-yl] ester $^1$H-NMR (CDCl$_3$): δ=1.2 (3H), 1.6 (2H), 1.75 (2H), 1.9 (2H), 2.2-2.4 (4H), 2.4-2.6 (3H), 2.9 (2H), 3.1 (2H), 3.6 (2H), 3.75 (3H), 3.8 (1H), 4.05 (1H), 6.55 (1H), 6.75 (1H), 6.85 (1H), 7.0 (1H), 7.3 (1H), 7.35 (1H), 7.45 (1H), 7.65 (1H), 7.9 (1H) and 8.3 (1H) ppm.

Example 50

4-(1-Methyl-piperidine-4-yl)-piperazine-1-carboxylic acid-[1-(2-trifluoromethoxy-1-benzenesulfonyl)-5-methoxy-2-oxo-3-(2-ethoxyphenyl)-2,3-dihydro-1H-indole-3-yl] ester $^1$H-NMR (CDCl$_3$): δ=1.15 (3H), 1.4-1.8 (4H), 1.9 (2H), 2.2-2.7 (8H), 2.8-3.0 (3H), 3.05 (1H), 3.55 (1H), 3.7 (3H), 3.8 (1H), 4.05 (1H), 6.55 (1H), 6.75 (1H), 6.85 (1H), 6.95 (1H), 7.2-7.45 (3H), 7.55 (1H), 7.65 (1H), 7.9 (1H) and 8.3 (1H) ppm.

Example 51

4-(1-Methyl-piperidine-4-yl)-piperazine-1-carboxylic acid-[1-(2-methoxy-1-benzenesulfonyl)-5-methoxy-2-oxo-3-(2-ethoxyphenyl)-2,3-dihydro-1H-indole-3-yl] ester $^1$H-NMR (CDCl$_3$): δ=1.25 (3H), 1.4-1.8 (4H), 1.9 (2H), 2.2-2.6 (8H), 2.9 (2H), 3.05 (2H), 3.5-3.7 (4H), 3.75 (3H), 3.8 (1H), 4.05 (1H), 6.55 (1H), 6.75 (1H), 6.8-7.1 (4H), 7.25 (1H), 7.5 (1H), 7.7 (1H), 7.9 (1H) and 8.15 (1H) ppm.

Example 52

4-(1-Methyl-piperidine-4-yl)-piperazine-1-carboxylic acid-[1-benzenesulfonyl-5-methoxy-2-oxo-3-(2-ethoxyphenyl)-2,3-dihydro-1H-indole-3-yl] ester $^1$H-NMR (CDCl$_3$): δ=1.25 (3H), 1.5-1.8 (4H), 1.9 (2H), 2.2-2.4 (6H), 2.5 (2H), 2.9 (2H), 3.0 (2H), 3.55 (2H), 3.7 (3H), 3.75 (1H), 4.0 (1H), 6.5 (1H), 6.75 (1H), 6.8 (1H), 7.0 (1H), 7.25 (1H), 7.45 (1H), 7.6 (1H), 7.7 (1H), 7.85 (1H) and 8.15 (1H) ppm.

Example 53

1-(2,4-Dimethoxy-1-benzenesulfonyl)-5-methoxy-3-(2-methoxyphenyl)-3{2[4-methyl-piperidine-1-yl)-piperazine-1-yl]-2-oxo-ethoxy}-1,3-dihydroindolone dihydrochloride $^1$H-NMR (D$_6$-DMSO): δ=2.1 (2H), 2.3 (2H), 2.7 (3H), 2.8-3.3 (6H), 3.3-3.7 (8H), 3.7-4.0 (12H), 4.25 (1H), 6.5 (1H), 6.8 (2H), 6.95 (1H), 7.1-7.15 (2H), 7.35 (1H), 7.7 (1H), 7.75 (1H), 7.95 (1H), 10.6 (N$^+$–H) and 11.8 (N$^+$–H) ppm.

Example 54

1-(2,4-Dimethoxy-1-benzenesulfonyl)-5-methoxy-3-(2-methoxyphenyl)-3{2[4-methyl-piperazine-1-yl)-piperidine-1-yl]-2-oxo-ethoxy}-1,3-dihydroindolone $^1$H-NMR (D$_6$-DMSO): δ=1.5 (2H), 2.1 (2H), 2.8 (3H), 2.9 (1H), 3.25-3.8 (22H), 3.9 (3H), 4.3 (1H), 6.5 (1H), 6.75 (2H), 6.95 (1H), 7.05 (1H), 7.15 (1H), 7.35 (1H), 7.75 (1H), 7.8 (1H) and 7.95 (1H) ppm.

Example 55

4-(4-Methyl-piperazine-1-yl)-piperidine-1-carboxylic acid-[1-(2,4-dimethoxy-1-benzenesulfonyl)-5-methoxy-2-oxo-3-(2-methoxyphenyl)-2,3-dihydro-1H-indole-3-yl] ester dihydrochloride $^1$H-NMR (D$_6$-DMSO): δ=1.4 (1H), 1.6 (1H), 2.1 (2H), 2.7 (1H), 2.8 (3H), 3.0 (1H), 3.25-3.8 (19H), 3.9 (3H), 4.3 (1H), 6.6 (1H), 6.65 (1H), 6.9-7.0 (2H), 7.05 (1H), 7.35 (1H), 7.65 (1H), 7.7 (1H) and 7.9 (1H) ppm.

Example 56

4-(1-Methyl-piperidine-4-yl)-piperazine-1-carboxylic acid-[1-(2-methyl-1-benzenesulfonyl)-5-methoxy-2-oxo-3-[2-(2-methoxyethyl)phenyl]-2,3-dihydro-1H-indole-3-yl] ester dihydrochloride $^1$H-NMR (D$_6$-DMSO): δ=2.15 (2H), 2.3 (2H), 2.4 (3H), 2.7 (3H), 2.9-3.2 (5H), 3.25-3.7 (10H), 3.8 (3H), 3.85 (1H), 4.25 (1H), 6.55 (1H), 7.0 (1H), 7.1 (2H), 7.30-7.5 (4H), 7.6 (1H), 7.7 (1H) and 8.05 (1H) ppm.

Example 57

4-(1-Methyl-piperidine-4-yl)-piperazine-1-carboxylic acid-[1-(2-methoxy-4-methyl-1-benzenesulfonyl)-5-methoxy-2-oxo-3-[2-(2-methoxyethyl)phenyl]-2,3-dihydro-1H-indole-3-yl] ester dihydrochloride $^1$H-NMR (D$_6$-DMSO): δ=2.1 (2H), 2.3 (2H), 2.35 (3H), 2.7 (3H), 2.9-3.2 (5H), 3.25-3.7 (16H), 3.8 (3H), 3.85 (1H), 4.25 (1H), 6.5 (1H), 6.8-7.0 (3H), 7.1 (2H), 7.35 (1H), 7.4 (1H), 7.65 (1H), 7.75 (1H), 10.6 (N$^+$–H) and 11.8 (N$^+$–H) ppm.

Example 58

4-(1-Methyl-piperidine-4-yl)-piperazine-1-carboxylic acid-[1-(2,4-dimethoxy-1-benzenesulfonyl)-5-methoxy-2-oxo-3-[2-(2-methoxyethyl)phenyl]-2,3-dihydro-1H-indole-3-yl] ester dihydrochloride $^1$H-NMR (D$_6$-DMSO): δ=2.1 (2H), 2.3 (2H), 2.7 (3H), 2.8-3.2 (5H), 3.25-3.7 (16H), 3.75 (3H), 3.8-3.9 (4H), 4.25 (1H), 6.45 (1H), 6.55 (1H), 6.65 (1H), 6.9 (1H), 7.1 (2H), 7.35 (1H), 7.4 (1H), 7.65 (1H), 7.75 (1H), 10.6 (N$^+$–H) and 11.8 (N$^+$–H) ppm.

Example 59

4-(1-Methyl-piperidine-4-yl)-piperazine-1-carboxylic acid-[5-chloro-1-(2,4-dimethoxy-benzenesulfonyl)-3-(2-methoxymethyl-phenyl)-2-oxo-2,3-dihydro-1H-indole-3-yl] ester $^1$H-NMR (CDCl$_3$): δ=1.6 (2H), 1.75 (2H), 1.95 (2H), 2.2-2.3 (4H), 2.35-2.6 (4H), 2.9 (2H), 3.25 (2H), 3.4 (6H), 3.55 (2H), 3.85 (3H), 4.7 (1H), 5.0 (1H), 6.35 (1H), 6.55 (2H), 7.05-7.15 (1H), 7.35 (1H), 7.4 (1H), 7.65 (1H), 7.9 (1H) and 8.0 (1H) ppm.

Example 60

4-(1-Methyl-piperidine-4-yl)-piperazine-1-carboxylic acid-[1-(2,4-dimethoxy-benzenesulfonyl)-5-methoxy-2-oxo-3-(2-ethoxyphenyl)-2,3-dihydro-1H-indole-3-yl] amide $^1$H-NMR (CDCl$_3$): δ=1.5-1.7 (5H), 1.75 (2H), 1.9 (2H), 2.15-2.35 (4H), 2.45 (4H), 2.9 (2H), 3.25 (4H), 3.55 (3H), 3.75 (3H), 3.85 (3H), 4.2 (2H), 6.4 (1H), 6.55 (1H), 6.75-6.95 (5H), 7.05 (1H), 7.2 (1H), 7.8 (1H) and 8.1 (1H) ppm.

Example 61

4-(1-Methyl-piperidine-4-yl)-piperazine-1-carboxylic acid-[1-benzenesulfonyl-5-methoxy-2-oxo-3-(2-ethoxyphenyl)-2,3-dihydro-1H-indole-3-yl] amide dihydrochloride ¹H-NMR (D₆-DMSO) δ=1.25 (3H), 2.0 (2H), 2.3 (2H), 2.75 (3H), 2.75-3.0 (4H), 3.15 (2H), 3.3-3.6 (4H), 3.65 (3H), 3.75-4.1 (4H), 6.85 (2H), 6.85-7.0 (2H), 7.25-7.45 (2H), 7.6 (3H), 7.75 (1H), 7.9 (1H), 8.05 (1H), 10.4 (N⁺–H) and 11.1 (N⁺–H) ppm.

Example 62

4-(1-Methyl-piperidine-4-yl)-piperazine-1-carboxylic acid-[1-benzenesulfonyl-5-cyano-2-oxo-3-(2-ethoxyphenyl)-2,3-dihydro-1H-indole-3-yl] ester ¹H-NMR (CDCl₃): δ=1.2 (3H), 1.4-2.1 (6H), 2.3-2.7 (8H), 2.9 (2H), 3.15 (2H), 3.6 (2H), 3.75 (1H), 4.0 (1H), 6.8 (1H), 7.0 (1H), 7.25 (1H), 7.3 (1H), 7.5 (2H), 7.6-7.75 (3H) and 8.1 (3H) ppm.

Example 63

4-(1-Methyl-piperidine-4-yl)-piperazine-1-carboxylic acid-[1-(2,4-dimethoxy-1-benzenesulfonyl)-5-cyano-2-oxo-3-(2-ethoxyphenyl)-2,3-dihydro-1H-indole-3-yl] ester ¹H-NMR (CDCl₃): δ=1.25 (3H), 1.5-1.9 (6H), 2.1 (1H), 2.25-2.5 (4H), 2.55 (2H), 2.95-3.2 (4H), 3.55 (3H), 3.6 (2H), 3.8 (1H), 3.85 (3H), 4.05 (1H), 6.4 (1H), 6.55 (1H), 6.8 (1H), 7.0 (1H), 7.25 (2H), 7.65 (2H), 8.05 (1H) and 8.15 (1H) ppm.

Example 64

4-(1-Methyl-piperidine-4-yl)-piperazine-1-carboxylic acid-[1-(2,4-dichloro-1-benzenesulfonyl)-5-cyano-2-oxo-3-(2-ethoxyphenyl)-2,3-dihydro-1H-indole-3-yl] ester

Example 65

4-(1-Methyl-piperidine-4-yl)-piperazine-1-carboxylic acid-[1-(2-methoxy-1-benzenesulfonyl)-5-cyano-2-oxo-3-(2-ethoxyphenyl)-2,3-dihydro-1H-indole-3-yl] ester ¹H-NMR (CDCl₃): δ=1.25 (3H), 1.5-1.9 (6H), 2.1 (1H), 2.25-2.5 (4H), 2.55 (2H), 2.95-3.2 (4H), 3.55 (3H), 3.6 (2H), 3.8 (1H), 3.85 (3H), 4.05 (1H), 6.4 (1H), 6.55 (1H), 6.8 (1H), 7.0 (1H), 7.25 (2H), 7.65 (2H), 8.05 (1H) and 8.15 (1H) ppm.

Example 66

4-(1-Methyl-piperidine-4-yl)-piperazine-1-carboxylic acid-[1-(2,4-dimethoxy-benzenesulfonyl)-5-chloro-2-oxo-3-(2-ethoxyphenyl)-2,3-dihydro-1H-indole-3-yl] amide dihydrochloride ¹H-NMR (D₆-DMSO): δ=1.2 (3H), 2.1 (2H), 2.3 (2H), 2.7 (3H), 2.9 (4H), 3.2 (2H), 3.3-3.7 (8H), 3.8-4.0 (5H), 4.05 (2H), 6.65 (2H), 6.9 (1H), 7.0 (1H), 7.2 (1H), 7.25-7.4 (3H), 7.7 (1H), 7.9 (2H), 10.5 (N⁺–H) and 11.3 (N⁺–H) ppm.

Example 67

4-(1-Methyl-piperidine-4-yl)-piperazine-1-carboxylic acid-[1-benzenesulfonyl-5-chloro-2-oxo-3-(2-ethoxyphenyl)-2,3-dihydro-1H-indole-3-yl] amide dihydrochloride ¹H-NMR (D₆-DMSO): δ=1.1 (3H), 2.1 (2H), 2.3 (2H), 2.7 (3H), 2.8-3.0 (4H), 3.2 (2H), 3.3-3.7 (4H), 3.8-4.0 (4H), 6.95 (2H), 7.2 (1H), 7.35 (2H), 7.55 (1H), 7.65 (2H), 7.7-7.85 (2H), 7.95 (1H), 8.05 (1H), 10.5 (N⁺–H) and 11.3 (N⁺–H) ppm.

Example 68

4-(1-Methyl-piperidine-4-yl)-piperazine-1-carboxylic acid-[1-(2,4,6-trimethyl-1-benzenesulfonyl)-5-chloro-2-oxo-3-(2-ethoxyphenyl)-2,3-dihydro-1H-indole-3-yl] amide dihydrochloride ¹H-NMR (D₆-DMSO): δ=1.2 (3H), 2.05 (2H), 2.3 (6H), 2.6 (3H), 2.85-3.05 (4H), 3.2 (2H), 3.4-3.7 (4H), 3.95 (2H), 4.05 (2H), 6.85 (2H), 7.0 (1H), 7.1 (3H), 7.3 (1H), 7.35 (1H), 7.45 (1H), 7.75 (1H), 7.95 (1H), 10.5 (N⁺–H) and 11.2 (N⁺–H) ppm.

Example 69

4-(1-Methyl-piperidine-4-yl)-piperazine-1-carboxylic acid-[1-(4-isopropyl-1-benzenesulfonyl)-5-chloro-2-oxo-3-(2-ethoxyphenyl)-2,3-dihydro-1H-indole-3-yl] amide

Example 70

4-(1-Methyl-piperidine-4-yl)-piperazine-1-carboxylic acid-[1-(4-cyano-1-benzenesulfonyl)-5-chloro-2-oxo-3-(2-ethoxyphenyl)-2,3-dihydro-1H-indole-3-yl] amide ¹H-NMR (CDCl₃): δ=1.5 (3H), 1.6 (2H), 1.75 (2H), 1.95 (2H), 2.2-2.3 (4H), 2.45 (4H), 2.9 (2H), 3.05-3.25 (4H), 4.1 (1H), 4.2 (1H), 6.5 (1H), 6.9 (2H), 7.1 (1H), 7.15 (1H), 7.25-7.35 (2H), 7.75 (2H), 7.85 (1H) and 8.2 (1H) ppm.

Example 71

4-(1-Methyl-piperidine-4-yl)-piperazine-1-carboxylic acid-[5-chloro-3-(2-ethoxy-phenyl)-1-(2-methoxy-benzenesulfonyl)-2-oxo-2,3-dihydro-1H-indole-3-yl] amide ¹H-NMR (CDCl₃): δ=1.5 (3H), 1.6 (2H), 1.75 (2H), 1.95 (2H), 2.2-2.35 (4H), 2.45 (4H), 2.9 (2H), 3.25 (4H), 3.6 (3H), 4.1-4.25 (2H), 6.75-6.85 (2H), 6.9 (3H), 7.1 (1H), 7.25 (2H), 7.35 (1H), 7.55 (2H), 7.9 (1H) and 8.15 (1H) ppm.

Example 72

4-(1-Methyl-piperidine-4-yl)-piperazine-1-carboxylic acid-[1-(2,4-dimethoxy-benzenesulfonyl)-3-(2-ethoxy-phenyl)-5-fluoro-2-oxo-2,3-dihydro-1H-indole-3-yl] ester ¹H-NMR (CDCl₃): δ=1.25 (3H), 1.65 (2H), 1.75 (2H), 2.05 (2H), 2.2-2.7 (8H), 2.95 (2H), 3.1 (2H), 3.6 (5H), 3.75-

3.9 (4H), 4.05 (1H), 6.4 (1H), 6.55 (1H), 6.7 (1H), 6.8 (1H), 6.9-7.1 (2H), 7.3 (1H), 7.65 (1H), 7.95 (1H) and 8.1 (1H) ppm.

Example 73

4-(1-Methyl-piperidine-4-yl)-piperazine-1-carboxylic acid-[1-benzenesulfonyl-3-(2-ethoxy-phenyl)-5-fluoro-2-oxo-2,3-dihydro-1H-indole-3-yl] ester $^1$H-NMR (CDCl$_3$): δ=1.25 (3H), 1.65 (2H), 1.75 (2H), 2.0 (2H), 2.2-2.7 (8H), 2.85-3.15 (4H), 3.6 (2H), 3.8 (1H), 4.0 (1H), 6.7 (1H), 6.8 (1H), 7.0 (2H), 7.3 (1H), 7.5 (2H), 7.6 (1H), 7.7 (1H), 7.9 (1H) and 8.15 (2H) ppm.

Example 74

4-(1-Methyl-piperidine-4-yl)-piperazine-1-carboxylic acid-[3-(2-ethoxy-phenyl)-5-methoxy-1-(4-methoxy-benzenesulfonyl)-2-oxo-2,3-dihydro-1H-indole-3-yl] ester $^1$H-NMR (CDCl$_3$): δ=1.25 (3H), 1.4-1.9 (6H), 2.2 (2H), 2.25-2.7 (6H), 2.9-3.2 (4H), 3.6 (2H), 3.8 (1H), 3.85 (3H), 4.0 (1H), 6.8 (1H), 6.95 (2H), 7.05 (1H), 7.3 (1H), 7.35 (1H), 7.65 (1H), 7.7 (1H) and 8.05 (3H) ppm.

Example 75

4-(1-Methyl-piperidine-4-yl)-piperazine-1-carboxylic acid-[3-(2-isopropoxy-phenyl)-5-methoxy-1-(4-methoxy-benzenesulfonyl)-2-oxo-2,3-dihydro-1H-indole-3-yl] ester $^1$H-NMR (CDCl$_3$): δ=0.9 (3H), 1.35 (3H), 1.5-1.7 (4H), 1.95 (2H), 2.2-2.4 (6H), 2.5 (2H), 2.9 (2H), 3.0 (2H), 3.6 (2H), 3.7 (3H), 3.8 (3H), 4.5 (1H), 6.5 (1H), 6.8 (1H), 6.85 (1H), 6.9-7.0 (3H), 7.25 (1H), 7.7 (1H), 7.85 (2H) and 8.05 (2H) ppm.

Example 76

4-(1-Methyl-piperidine-4-yl)-piperazine-1-carboxylic acid-[5-methoxy-1-(4-methoxy-benzenesulfonyl)-2-oxo-3-(2-propoxy-phenyl)-2,3-dihydro-1H-indole-3-yl] ester $^1$H-NMR (CDCl$_3$): δ=0.8 (3H), 1.5-1.85 (6H), 1.9 (2H), 2.2-2.3 (4H), 2.35 (2H), 2.5 (2H), 2.9 (2H), 3.05 (2H), 3.6 (2H), 3.65-3.75 (4H), 3.85 (3H), 3.9 (1H), 6.55 (1H), 6.8 (2H), 6.9 (2H), 7.0 (1H), 7.25 (1H), 7.7 (1H), 7.85 (1H) and 8.15 (2H) ppm.

Example 77

4-(1-Methyl-piperidine-4-yl)-piperazine-1-carboxylic acid-[5-chloro-3-(2-ethoxy-phenyl)-1-(4-methoxy-benzenesulfonyl)-2-oxo-2,3-dihydro-1H-indole-3-yl] amide $^1$H-NMR (CDCl$_3$): δ=1.5-1.75 (5H), 1.75 (2H), 1.9 (2H), 2.2-2.35 (4H), 2.4 (4H), 2.9 (2H), 3.15-3.3 (4H), 3.85 (3H), 4.15 (1H), 4.2 (1H), 6.65 (1H), 6.85-7.05 (5H), 7.2-7.3 (3H), 7.8 (1H) and 8.15 (2H) ppm.

Example 78

4-(1-Methyl-piperidine-4-yl)-piperazine-1-carboxylic acid-{5-methoxy-1-(2-methoxy-benzenesulfonyl)-3-[2-(2-methoxy-ethyl)-phenyl]-2-oxo-2,3-dihydro-1H-indole-3-yl} amide dihydrochloride $^1$H-NMR (D$_6$-DMSO): δ=2.05 (2H), 2.3 (2H), 2.7 (3H), 2.85-3.2 (5H), 3.25-3.7 (16H), 3.75 (3H), 3.85 (1H), 4.25 (1H), 6.5 (1H), 6.9 (1H), 7.25 (1H), 7.4 (1H), 7.75 (2H), 7.9 (1H), 10.5 (N$^+$–H) and 11.7 (N$^+$–H) ppm.

Example 79

4-(1-Methyl-piperidine-4-yl)-piperazine-1-carboxylic acid-[5-methoxy-1-(2-methoxy-benzenesulfonyl)-2-oxo-3-(2-propoxy-phenyl)-2,3-dihydro-1H-indole-3-yl] ester $^1$H-NMR (CDCl$_3$): δ=0.8 (3H), 1.4-1.85 (6H), 1.9 (2H), 2.2-2.4 (6H), 2.5 (2H), 2.9 (2H), 3.1 (2H), 3.55 (2H), 3.6 (3H), 3.7 (4H), 3.95 (1H), 6.55 (1H), 6.65-7.05 (5H), 7.25 (1H), 7.5 (1H), 7.65 (1H), 7.9 (1H) and 8.1 (1H) ppm.

Example 80

4-(1-Methyl-piperidine-4-yl)-piperazine-1-carboxylic acid-[3-(2-isopropoxy-phenyl)-5-methoxy-1-(2-methoxy-benzenesulfonyl)-2-oxo-2,3-dihydro-1H-indole-3-yl] ester $^1$H-NMR (CDCl$_3$): δ=0.9 (3H), 1.4 (3H), 1.5-1.8 (4H), 1.95 (2H), 2.2-2.45 (6H), 2.5 (2H), 2.9 (2H), 3.05 (2H), 3.45-3.65 (5H), 3.7 (3H), 4.5 (1H), 6.5 (1H), 6.8 (1H), 6.85-6.95 (3H), 7.0 (1H), 7.25 (1H), 7.5 (1H), 7.7 (1H), 7.9 (1H) and 8.15 (1H) ppm.

Example 81

4-(1-Methyl-piperidine-4-yl)-piperazine-1-carboxylic acid-[5-methoxy-1-(4-methoxy-benzenesulfonyl)-3-(2-methoxymethyl-phenyl)-2-oxo-2,3-dihydro-1H-indole-3-yl] ester $^1$H-NMR (CDCl$_3$): δ=1.5-1.9 (4H), 2.0 (2H), 2.2-2.6 (8H), 2.95 (2H), 3.2 (2H), 3.3-3.7 (9H), 3.75 (3H), 3.85 (3H), 6.6 (1H), 6.7 (1H), 6.85-7.05 (4H), 7.25 (1H), 7.35 (1H), 7.85 (1H) and 8.20 (1H) ppm.

Example 82

4-(1-Methyl-piperidine-4-yl)-piperazine-1-carboxylic acid-[1-benzenesulfonyl-5-chloro-3-(2-methoxymethyl-phenyl)-2-oxo-2,3-dihydro-1H-indole-3-yl] ester $^1$H-NMR (CDCl$_3$): δ=1.4-1.8 (6H), 1.9 (2H), 2.2-2.3 (4H), 2.35 (1H), 2.4 (2H), 2.55 (1H), 2.9 (2H), 3.15 (2H), 3.4 (3H), 3.55 (2H), 4.75 (1H), 5.0 (1H), 6.55 (1H), 7.05-7.15 (2H), 7.3-7.55 (4H), 7.6-7.7 (2H), 7.95 (1H) and 8.05 (1H) ppm.

Example 83

4-(4-Methyl-piperazine-1-yl)-piperidine-1-carboxylic acid-[3-(2-ethoxy-phenyl)-5-methoxy-1-(2-methoxy-benzenesulfonyl)-2-oxo-2,3-dihydro-1H-indole-3-yl] ester $^1$H-NMR (CDCl$_3$): δ=1.1 (1H), 1.25 (3H), 1.35-1.9 (5H), 2.25-2.7 (11H), 2.9 (1H), 3.6 (3H), 3.65 (1H), 3.7 (3H), 3.75

Example 84

4-(4-Methyl-piperazine-1-yl)-piperidine-1-carboxylic acid-[1-(2,4-dimethoxy-benzenesulfonyl)-3-(2-ethoxy-phenyl)-5-methoxy-2-oxo-2,3-dihydro-1H-indole-3-yl] ester $^1$H-NMR (CDCl$_3$): δ=1.2 (1H), 1.25 (3H), 1.35-1.9 (5H), 2.25-2.7 (11H), 2.9 (1H), 3.55 (3H), 3.65-3.7 (4H), 3.8 (1H), 3.85 (3H), 4.05 (1H), 4.25 (1H), 6.4 (1H), 6.55 (2H), 6.75 (1H), 6.85 (1H), 6.95 (1H), 7.25 (1H), 7.7 (1H), 7.85 (1H) and 8.05 (1H) ppm.

Example 85

4-(4-Methyl-piperazine-1-yl)-piperidine-1-carboxylic acid-[3-(2-ethoxy-phenyl)-5-methoxy-1-(4-methoxy-benzenesulfonyl)-2-oxo-2,3-dihydro-1H-indole-3-yl] ester $^1$H-NMR (CDCl$_3$): δ=1.25 (3H), 1.35-1.9 (6H), 2.25-2.7 (11H), 2.9 (1H), 3.6 (1H), 3.7 (3H), 3.8 (1H), 3.85 (3H), 4.0 (1H), 4.25 (1H), 6.5 (1H), 6.75 (1H), 6.8 (1H), 6.95 (2H), 7.0 (1H), 7.25 (1H), 7.7 (1H), 7.85 (1H) and 8.1 (2H) ppm.

Example 86

4-(4-Methyl-piperazine-1-yl)-piperidine-1-carboxylic acid-[3-(2-isopropoxy-phenyl)-5-methoxy-1-(2-methoxy-benzenesulfonyl)-2-oxo-2,3-dihydro-1H-indole-3-yl] ester $^1$H-NMR (CDCl$_3$): δ=0.85 (3H), 1.1 (1H), 1.25-1.9 (11H), 2.2-2.7 (11H), 2.85 (1H), 3.5-3.65 (4H), 3.7 (3H), 4.2 (1H), 4.5 (1H), 6.5 (1H), 6.75 (1H), 6.8-7.1 (5H), 7.25 (1H), 7.7 (1H), 7.9 (1H) and 8.15 (2H) ppm.

Example 87

4-(4-Methyl-piperazine-1-yl)-piperidine-1-carboxylic acid-[1-(2,4-dimethoxy-L=benzenesulfonyl)-3-(2-isopropoxy-phenyl)-5-methoxy-2-oxo-2,3-dihydro-1H-indole-3-yl] ester $^1$H-NMR (CDCl$_3$): δ=0.85 (3H), 1.1-1.9 (9H), 2.2-2.75 (11H), 2.9 (1H), 3.6 (4H), 3.65-3.75 (4H), 3.8 (3H), 4.25 (1H), 4.5 (1H), 6.4 (1H), 6.5 (2H), 6.75 (1H), 6.85 (1H), 6.9 (1H), 7.25 (1H), 7.7 (1H), 7.9 (1H) and 8.1 (1H) ppm.

Example 88

4-(4-Methyl-piperazine-1-yl)-piperidine-1-carboxylic acid-[5-chloro-3-(2-ethoxy-phenyl)-1-(4-methoxy-benzenesulfonyl)-2-oxo-2,3-dihydro-1H-indole-3-yl] ester $^1$H-NMR (CDCl$_3$): δ=1.25 (3H), 1.35-2.0 (6H), 2.2-2.75 (10H), 2.9 (1H), 3.6 (1H), 3.75-3.9 (4H), 4.0 (1H), 4.25 (1H), 6.8 (1H), 6.95 (3H), 7.0 (1H), 7.3 (2H), 7.7 (1H), 7.85 (1H) and 8.05 (1H) ppm.

Example 89

4-(4-Methyl-piperazine-1-yl)-piperidine-1-carboxylic acid-[3-(2-isopropoxy-phenyl)-5-methoxy-1-(4-methoxy-benzenesulfonyl)-2-oxo-2,3-dihydro-1H-indole-3-yl] ester $^1$H-NMR (CDCl$_3$): δ=0.85 (1H), 1.1-1.9 (9H), 2.2-2.7 (11H), 2.9 (1H), 3.6 (1H), 3.7 (3H), 3.85 (3H), 4.25 (1H), 4.5 (1H), 6.5 (1H), 6.8 (1H), 6.85 (1H), 6.85-7.0 (3H), 7.3 (1H), 7.7 (1H), 7.85 (1H) and 8.05 (2H) ppm.

Example 90

4-(4-Methyl-piperazine-1-yl)-piperidine-1-carboxylic acid-[5-chloro-3-(2-ethoxy-phenyl)-1-(2-methoxy-benzenesulfonyl)-2-oxo-2,3-dihydro-1H-indole-3-yl] ester $^1$H-NMR (CDCl$_3$): δ=1.1 (1H), 1.25 (3H), 1.35-1.9 (5H), 2.2-2.7 (11H), 2.9 (1H), 3.5-3.7 (4H), 3.8 (1H), 4.05 (1H), 4.25 (1H), 6.8 (1H), 6.9-7.1 (4H), 7.3 (2H), 7.5 (1H), 7.65 (1H), 7.95 (1H) and 8.15 (1H) ppm.

Example 91

4-(4-Methyl-piperazine-1-yl)-piperidine-1-carboxylic acid-[5-chloro-1-(2,4-dimethoxy-benzenesulfonyl)-3-(2-ethoxy-phenyl)-2-oxo-2,3-dihydro-1H-indole-3-yl] ester $^1$H-NMR (CDCl$_3$): δ=0.85 (3H), 1.0-1.9 (6H), 2.25 (3H), 2.25-2.7 (8H), 2.9 (1H), 3.55 (3H), 3.65 (1H), 3.75-3.85 (4H), 4.05 (1H), 4.2 (1H), 6.4 (1H), 6.5 (1H), 6.75 (1H), 6.9-7.1 (2H), 7.3 (2H), 7.7 (1H), 7.9 (1H) and 8.05 (1H) ppm.

Example 92

4-(1-Methyl-piperidine-4-yl)-piperazine-1-carboxylic acid-[1-(2-methoxy-benzenesulfonyl)-3-(2-methoxy-phenyl)-2-oxo-6-trifluoromethyl-2,3-dihydro-1H-indole-3-yl] ester

Example 93

4-(1-Methyl-piperidine-4-yl)-piperazine-1-carboxylic acid-[3-(2-ethoxy-phenyl)-5-fluoro-1-(2-methoxy-benzenesulfonyl)-2-oxo-2,3-dihydro-1H-indole-3-yl] ester $^1$H-NMR (CDCl$_3$): δ=1.25 (3H), 1.5-1.8 (4H), 1.9 (2H), 2.2-2.6 (8H), 2.9 (2H), 3.1 (2H), 3.5-3.7 (5H), 3.8 (3H), 4.05 (3H), 6.7 (1H), 6.8 (1H), 6.9-7.1 (4H), 7.25 (1H), 7.5 (1H), 7.65 (1H), 7.95 (1H) and 8.150 (1H) ppm.

Example 94

4-(1-Methyl-piperidine-4-yl)-piperazine-1-carboxylic acid-[3-(2-ethoxy-phenyl)-5-fluoro-1-(4-methoxy-benzenesulfonyl)-2-oxo-2,3-dihydro-1H-indole-3-yl] ester dihydrochloride $^1$H-NMR (D$_6$-DMSO): δ=1.0 (3H), 2.05 (2H), 2.3 (2H), 2.7 (3H), 2.8-3.9 (17H), 4.3 (1H), 6.95-7.05 (2H), 7.1 (2H), 7.25 (1H), 7.35 (1H), 7.75 (2H), 7.95 (2H), 10.5 (NH$^+$) and 11.6 (NH$^+$) ppm.

Example 95

4-(1-Methyl-piperidine-4-yl)-piperazine-1-carboxylic acid-[1-(4-cyano-benzenesulfonyl)-3-(2-ethoxy-phenyl)-5-fluoro-2-oxo-2,3-dihydro-1H-indole-3-yl] ester $^1$H-NMR (CDCl$_3$): δ=1.3 (3H), 1.5-1.8 (4H), 1.9 (2H), 2.2-2.6 (8H), 2.8-3.05 (4H), 3.55 (2H), 3.8 (1H), 4.05 (3H), 6.7 (1H), 6.8 (1H), 7.05 (2H), 7.3 (1H), 7.7 (1H), 7.8 (2H), 7.9 (1H) and 8.2 (1H) ppm.

Example 96

4-(1-Methyl-piperidine-4-yl)-piperazine-1-carboxylic acid-[5-chloro-3-(2-ethoxy-phenyl)-1-(4-methoxy-benzenesulfonyl)-2-oxo-2,3-dihydro-1H-indole-3-yl] ester dihydrochloride $^1$H-NMR (D$_6$-DMSO): δ=2.1 (2H), 2.3 (2H), 2.7 (3H), 2.9 (2H), 3.0-3.8 (13H), 3.85 (3H), 4.25 (1H), 4.7 (1H), 4.8 (1H), 6.5 (1H), 7.1 (2H), 7.2 (1H), 7.4 (1H), 7.5 (1H), 7.6 (2H), 7.8-7.9 (3H), 10.5 (NH$^+$) and 11.7 (NH$^+$) ppm.

Example 97

4-(1-Methyl-piperidine-4-yl)-piperazine-1-carboxylic acid-[5-chloro-1-(2-methoxy-benzenesulfonyl)-3-(2-methoxymethyl-phenyl)-2-oxo-2,3-dihydro-1H-indole-3-yl] ester $^1$H-NMR (CDCl$_3$): δ=1.6 (2H), 1.7 (2H), 1.9 (2H), 2.5 (4H), 2.4-2.6 (4H), 2.9 (2H), 3.25 (2H), 3.4 (3H), 3.5 (3H), 3.6 (2H), 4.3 (1H), 5.0 (1H), 6.55 (1H), 6.85 (1H), 7.0-7.2 (3H), 7.35 (1H), 7.45 (1H), 7.55 (1H), 7.65 (1H), 7.95 (1H) and 8.1 (1H) ppm.

Example 98

4-(1-Methyl-piperidine-4-yl)-piperazine-1-carboxylic acid-[3-(2-ethoxy-phenyl)-5-methoxy-1-(2-methoxy-benzenesulfonyl)-2-oxo-2,3-dihydro-1H-indole-3-yl] amide $^1$H-NMR (CDCl$_3$): δ=1.4-1.65 (5H), 1.75 (2H), 1.9 (2H), 2.15-2.35 (4H), 2.45 (4H), 2.9 (2H), 3.25 (4H), 3.55 (3H), 3.75 (3H), 4.15 (2H), 6.75-6.85 (3H), 6.9 (3H), 7.0 (1H), 7.05 (1H), 7.2 (1H), 7.5 (1H), 7.8 (1H) and 8.15 (1H) ppm.

Example 99

4-(1-Methyl-piperidine-4-yl)-piperazine-1-carboxylic acid-[3-(2-ethoxy-phenyl)-5-methoxy-1-(4-methoxy-benzenesulfonyl)-2-oxo-2,3-dihydro-1H-indole-3-yl] amide $^1$H-NMR (CDCl$_3$): δ=1.4-1.6 (5H), 1.75 (2H), 1.9 (2H), 2.15-2.35 (4H), 2.35-2.5 (4H), 2.9 (2H), 3.15-3.35 (4H), 3.7 (3H), 3.85 (3H), 4.1-4.3 (2H), 6.7-6.9 (8H), 7.25 (1H), 7.75 (1H) and 8.05 (1H) ppm.

Example 100

4-(1-Methyl-piperidine-4-yl)-piperazine-1-carboxylic acid-[1-(2,4-dimethoxy-benzenesulfonyl)-3-(2-methoxy-phenyl)-2-oxo-6-trifluoromethyl-2,3-dihydro-1H-indole-3-yl] ester

Example 101

4-(4-Methyl-piperazine-1-yl)-piperidine-1-carboxylic acid-[5-chloro-3-(2-ethoxy-phenyl)-1-(4-methoxy-benzenesulfonyl)-2-oxo-2,3-dihydro-1H-indole-3-yl] amide dihydrochloride $^1$H-NMR (D$_6$-DMSO): δ=1.15 (3H), 1.3-1.5 (2H), 1.9-2.1 (2H), 2.5-2.7 (2H), 2.8 (3H), 3.2-3.8 (9H), 3.8-4.1 (7H), 6.95 (2H), 7.15 (2H), 7.25 (1H), 7.3 (2H), 7.4 (1H), 7.7 (1H), 7.75 (1H) and 7.9 (2H) ppm.

Example 102

4-(4-Methyl-piperazine-1-yl)-piperidine-1-carboxylic acid-[5-chloro-1-(2,4-dimethoxy-benzenesulfonyl)-3-(2-ethoxy-phenyl)-2-oxo-2,3-dihydro-1H-indole-3-yl] amide dihydrochloride $^1$H-NMR (D$_6$-DMSO): δ=1.2 (3H), 1.3-1.5 (2H), 1.9-2.1 (2H), 2.65 (2H), 2.8 (3H), 3.2-3.8 (12H), 3.85 (3H), 3.95 (2H), 4.05 (2H), 6.6-6.7 (2H), 6.85 (1H), 7.0 (1H), 7.1 (1H), 7.25-7.4 (3H), 7.7 (2H) and 7.9 (1H) ppm.

Example 103

4-(4-Methyl-piperazine-1-yl)-piperidine-1-carboxylic acid-[5-chloro-3-(2-ethoxy-phenyl)-1-(2-methoxy-benzenesulfonyl)-2-oxo-2,3-dihydro-1H-indole-3-yl] amide $^1$H-NMR (CDCl$_3$): δ=1.2-1.4 (2H), 1.55 (3H), 1.75 (2H), 2.2-2.8 (14H), 3.55 (3H), 3.75 (2H), 4.2 (2H), 6.8 (1H), 6.85 (1H), 6.9-7.0 (3H), 7.05 (1H), 7.25 (2H), 7.3 (1H), 7.55 (1H), 7.9 (1H) and 8.15 (1H) ppm.

Example 104

4-(4-Methyl-piperazine-1-yl)-piperazine-1-carboxylic acid-[5-cyano-3-(2-ethoxy-phenyl)-2-oxo-1-(toluene-2-sulfonyl)-2,3-dihydro-1H-indole-3-yl] ester $^1$H-NMR (CDCl$_3$): δ=1.2 (3H), 1.6 (2H), 1.75 (2H), 1.95 (2H), 2.2-2.45 (6H), 2.55 (2H), 2.65 (3H), 2.9 (2H), 3.05 (1H), 3.15 (1H), 3.55 (2H), 3.85 (1H), 4.05 (1H), 6.8 (1H), 7.0 (1H), 7.3 (1H), 7.35 (1H), 7.45 (1H), 7.65 (1H), 8.05 (1H) and 8.25 (1H) ppm.

Example 105

4-(1-Methyl-piperidine-4-yl)-piperazine-1-carboxylic acid-[5-cyano-3-(2-ethoxy-phenyl)-2-oxo-1-(toluene-4-sulfonyl)-2,3-dihydro-1H-indole-3-yl] ester $^1$H-NMR (CDCl$_3$): δ=1.2 (3H), 1.6 (2H), 1.75 (2H), 2.05 (2H), 2.2-2.45 (9H), 2.5 (1H), 2.6 (1H), 2.9-3.2 (4H), 3.6 (2H), 3.8 (1H), 4.0 (1H), 6.8 (1H), 7.05 (1H), 7.2-7.4 (4H), 7.65 (1H), 7.7 (1H), 8.0 (2H) and 8.05 (1H) ppm.

Example 106

4-(1-Methyl-piperidine-4-yl)-piperazine-1-carboxylic acid-[1-(2-chloro-benzenesulfonyl)-5-cyano-3-(2-ethoxy-phenyl)-2-oxo-2,3-dihydro-1H-indole-3-yl] ester $^1$H-NMR (CDCl$_3$): δ=1.2 (3H), 1.6 (2H), 1.75 (2H), 1.9 (2H), 2.2-2.3 (4H), 2.35 (2H), 2.5 (1H), 2.6 (1H), 2.8 (2H), 3.0 (1H), 3.15 (1H), 3.6 (2H), 3.8 (1H), 4.05 (1H), 6.8 (1H), 7.0 (1H), 7.25-7.35 (2H), 7.4 (1H), 7.5 (2H), 7.65 (2H), 8.15 (1H) and 8.4 (1H) ppm.

Example 107

4-(1-Methyl-piperidine-4-yl)-piperazine-1-carboxylic acid-[5-cyano-1-(2,5-dimethoxy-benzenesulfonyl)-3-(2-ethoxy-phenyl)-2-oxo-2,3-dihydro-1H-indole-3-yl] ester $^1$H-NMR (CDCl$_3$): δ=1.25 (3H), 1.6 (2H), 1.75 (2H), 1.9 (2H), 2.2-2.3 (4H), 2.35 (2H), 2.55 (2H), 2.9 (2H), 3.1 (2H), 3.5-3.7 (5H), 3.8 (4H), 4.05 (1H), 6.8 (1H), 6.85 (1H), 7.0 (1H), 7.1 (1H), 7.25-7.35 (2H), 7.6-7.75 (3H) and 8.15 (1H) ppm.

Example 108

4-(1-Methyl-piperidine-4-yl)-piperazine-1-carboxylic acid-[5-cyano-1-(2-cyano-benzenesulfonyl)-3-(2-ethoxy-phenyl)-2-oxo-2,3-dihydro-1H-indole-3-yl] ester $^1$H-NMR (CDCl$_3$): δ=1.25 (3H), 1.6 (2H), 1.7 (2H), 1.95 (2H), 2.2-2.4 (6H), 2.45 (1H), 2.6 (1H), 2.7-3.1 (4H), 3.5 (1H), 3.6 (1H), 3.8 (1H), 4.05 (1H), 6.8 (1H), 7.05 (1H), 7.2 (1H), 7.35 (1H), 7.6-7.8 (4H), 7.85 (1H), 8.3 (1H) and 8.4 (1H) ppm.

Example 109

4-(1-Methyl-piperidine-4-yl)-piperazine-1-carboxylic acid-[5-cyano-1-(2,4-difluoro-benzenesulfonyl)-3-(2-ethoxy-phenyl)-2-oxo-2,3-dihydro-1H-indole-3-yl] ester $^1$H-NMR (CDCl$_3$): δ=1.25 (3H), 1.6 (2H), 1.7 (2H), 1.95 (2H), 2.2-2.45 (6H), 2.55 (2H), 2.8-3.2 (4H), 3.6 (2H), 3.8 (1H), 4.05 (1H), 6.8 (1H), 6.95-7.1 (2H), 7.25 (1H), 7.3 (1H), 7.7 (2H), 8.1 (1H) and 8.15 (1H) ppm.

Example 110

4-(1-Methyl-piperidine-4-yl)-piperazine-1-carboxylic acid-[5-cyano-1-(4-fluoro-benzenesulfonyl)-3-(2-ethoxy-phenyl)-2-oxo-2,3-dihydro-1H-indole-3-yl] ester $^1$H-NMR (CDCl$_3$): δ=1.25 (3H), 1.55 (2H), 1.75 (2H), 1.95 (2H), 2.2-2.3 (4H), 2.35 (2H), 2.55 (2H), 2.9 (2H), 3.0 (2H), 3.6 (2H), 3.8 (1H), 4.0 (1H), 6.8 (1H), 7.05 (1H), 7.15 (2H), 7.25 (1H), 7.3 (1H), 7.65 (1H), 7.7 (1H), 8.05 (1H) and 8.15 (1H) ppm.

Example 111

4-(1-Methyl-piperidine-4-yl)-piperazine-1-carboxylic acid-[5-cyano-3-(2-ethoxy-phenyl)-1-(4-isopropyl-benzenesulfonyl)-2-oxo-2,3-dihydro-1H-indole-3-yl] ester $^1$H-NMR (CDCl$_3$): δ=1.2-1.3 (9H), 1.55 (2H), 1.75 (2H), 1.95 (2H), 2.2-2.4 (6H), 2.45 (1H), 2.6 (1H), 2.8-3.1 (5H), 3.6 (2H), 3.75 (1H), 4.0 (1H), 6.8 (1H), 7.05 (1H), 7.25 (1H), 7.3-7.4 (1H), 7.65 (1H), 7.7 (1H), 8.0 (1H) and 8.1 (1H) ppm.

Example 112

4-(1-Methyl-piperidine-4-yl)-piperazine-1-carboxylic acid-[5-cyano-3-(2-ethoxy-phenyl)-1-(2-fluoro-benzenesulfonyl)-2-oxo-2,3-dihydro-1H-indole-3-yl] ester $^1$H-NMR (CDCl$_3$): δ=1.25 (3H), 1.6 (2H), 1.75 (2H), 1.95 (2H), 2.2-2.4 (6H), 2.5 (1H), 2.6 (1H), 2.85-3.0 (3H), 3.1 (1H), 3.6 (2H), 3.8 (1H), 4.05 (1H), 6.8 (1H), 7.05 (1H), 7.15 (1H), 7.2-7.4 (3H), 7.6 (1H), 7.7 (2H) and 8.15 (1H) ppm.

Example 113

4-(1-Methyl-piperidine-4-yl)-piperazine-1-carboxylic acid-[1-(5-chloro-2-methoxy-benzenesulfonyl)-5-cyano-3-(2-ethoxy-phenyl)-2-oxo-2,3-dihydro-1H-indole-3-yl] ester $^1$H-NMR (CDCl$_3$): δ=1.25 (3H), 1.6 (2H), 1.75 (2H), 1.95 (2H), 2.2-2.45 (5H), 2.55 (2H), 2.9 (2H), 3.05 (2H), 3.5-3.7 (5H), 3.8 (1H), 4.05 (1H), 6.8 (1H), 6.85 (1H), 7.0 (1H), 7.2-7.4 (2H), 7.45 (1H), 7.7 (2H) and 8.1 (2H) ppm.

Example 114

4-(1-Methyl-piperidine-4-yl)-piperazine-1-carboxylic acid-[5-cyano-3-(2-ethoxy-phenyl)-1-(2-methoxy-5-methyl-benzenesulfonyl)-2-oxo-2,3-dihydro-1H-indole-3-yl] ester $^1$H-NMR (CDCl$_3$): δ=1.25 (3H), 1.55 (2H), 1.7 (2H), 1.9 (2H), 2.2-2.3 (4H), 2.3-2.45 (5H), 2.55 (2H), 2.9 (2H), 3.1 (2H), 3.5-3.7 (5H), 3.8 (1H), 4.05 (1H), 6.8 (2H), 7.0 (1H), 7.2-7.4 (3H), 7.65 (2H), 7.9 (1H) and 8.1 (1H) ppm.

Example 115

4-(1-Methyl-piperidine-4-yl)-piperazine-1-carboxylic acid-[5-cyano-3-(2-ethoxy-phenyl)-1-(2-methoxy-4-methyl-benzenesulfonyl)-2-oxo-2,3-dihydro-1H-indole-3-yl] ester $^1$H-NMR (CDCl$_3$): δ=1.25 (3H), 1.55 (2H), 1.7 (2H), 1.9 (2H), 2.2-2.3 (4H), 2.3-2.45 (5H), 2.55 (2H), 2.9 (2H), 3.1 (2H), 3.5-3.7 (5H), 3.8 (1H), 4.05 (1H), 6.7 (1H), 6.8 (1H), 6.85 (1H), 7.0 (1H), 7.3 (2H), 7.65 (2H), 8.0 (1H) and 8.15 (1H) ppm.

Example 116

4-(1-Methyl-piperidine-4-yl)-piperazine-1-carboxylic acid-[1-benzenesulfonyl-5-cyano-3-(2-ethoxy-phenyl)-2-oxo-2,3-dihydro-1H-indole-3-yl] amide dihydrochloride $^1$H-NMR (D$_2$O): δ=0.95 (3H), 1.85 (2H), 2.3 (2H), 2.8 (3H), 3.05 (2H), 3.1-3.55 (9H), 3.6 (2H), 3.7 (1H), 3.8 (1H), 6.85 (1H), 6.95 (1H), 7.25 (1H), 7.45 (1H), 7.5 (3H), 7.6-7.7 (2H) and 7.8-8.0 (3H) ppm.

Example 117

4-(1-Methyl-piperidine-4-yl)-piperazine-1-carboxylic acid-[5-cyano-3-(2-ethoxy-phenyl)-1-(4-methoxy-benzenesulfonyl)-2-oxo-2,3-dihydro-1H-indole-3-yl] amide $^1$H-NMR (CDCl$_3$): δ=1.4-1.8 (7H), 1.95 (2H), 2.25 (4H), 2.45 (4H), 2.9 (2H), 3.1-3.3 (4H), 3.85 (3H), 4.1 (1H), 4.2 (1H), 6.5 (1H), 6.85-7.0 (4H), 7.1 (1H), 7.3 (1H), 7.5 (1H), 7.6 (1H) and 7.95-8.1 (3H) ppm.

Example 118

4-(1-Methyl-piperidine-4-yl)-piperazine-1-carboxylic acid-[5-cyano-3-(2-ethoxy-phenyl)-1-(2-methoxy-benzenesulfonyl)-2-oxo-2,3-dihydro-1H-indole-3-yl] amide dihydrochloride $^1$H-NMR (D$_2$O): δ=0.75 (3H), 1.95 (2H), 2.4 (2H), 2.85 (3H), 3.05 (2H), 3.2-3.4 (4H), 3.4 (3H), 3.5-3.9 (9H), 6.95 (2H), 7.1-7.2 (2H), 7.3-7.4 (2H), 7.6 (1H), 7.7-7.8 (2H), 7.8 (1H) and 8.1 (3H) ppm.

Example 119

4-(1-Methyl-piperidine-4-yl)-piperazine-1-carboxylic acid-[5-cyano-3-(2-ethoxy-phenyl)-1-(2,4-dimethoxy-benzenesulfonyl)-2-oxo-2,3-dihydro-1H-indole-3-yl] amide $^1$H-NMR (CDCl$_3$): δ=1.5-1.9 (7H), 2.05 (2H), 2.25-2.35 (4H), 2.45 (4H), 3.0 (2H), 3.15-3.3 (4H), 3.5 (3H), 3.85 (3H), 4.15 (1H), 4.25 (1H), 6.4 (1H), 6.55 (1H), 6.7 (1H), 6.85 (1H), 6.9 (2H), 7.25 (1H), 7.6 (2H) and 8.2 (2H) ppm.

Example 120

4-(1-Methyl-piperidine-4-yl)-piperazine-1-carboxylic acid-[1-(4-acetylamino-benzenesulfonyl)-5-cyano-3-(2-ethoxy-phenyl)-2-oxo-2,3-dihydro-1H-indole-3-yl] ester $^1$H-NMR (CDCl$_3$): δ=1.25 (3H), 1.6 (2H), 2.0 (2H), 2.15-2.25 (4H), 2.25-2.4 (5H), 2.5 (2H), 2.9-3.1 (4H), 3.5 (1H), 3.6 (1H), 3.8 (1H), 4.0 (1H), 6.8 (1H), 7.0 (1H), 7.25 (1H), 7.3 (1H), 7.6-7.75 (4H), 7.8 (1H) and 8.052 (3H) ppm.

Example 121

4-(1-Methyl-piperidine-4-yl)-piperazine-1-carboxylic acid-[1-(2,4-dimethoxy-benzenesulfonyl)-3-(2-ethoxy-phenyl)-5-fluoro-2-oxo-2,3-dihydro-1H-indole-3-yl] amide $^1$H-NMR (CDCl$_3$): δ=1.35 (2H), 1.5-1.9 (5H), 2.25-2.35 (4H), 2.3 (4H), 2.4-2.8 (10H), 3.5 (3H), 3.75-3.9 (5H), 4.1-4.3 (2H), 6.4 (1H), 6.55 (1H), 6.7-7.0 (3H), 7.05 (1H), 7.25 (1H), 7.9 (2H) and 8.1 (1H) ppm.

Example 122

4-(1-Methyl-piperidine-4-yl)-piperazine-1-carboxylic acid-[1-(2-methoxy-benzenesulfonyl)-3-(2-ethoxy-phenyl)-5-fluoro-2-oxo-2,3-dihydro-1H-indole-3-yl] amide $^1$H-NMR (CDCl$_3$): δ=1.2-1.4 (2H), 1.55 (3H), 1.6-1.9 (2H), 2.25-2.4 (4H), 2.4-2.8 (10H), 3.55 (3H), 3.8 (2H), 4.1-4.3 (2H), 6.8-7.1 (8H), 7.25 (1H), 7.5 (1H), 7.9 (1H) and 8.15 (1H) ppm.

Example 123

4-(1-Methyl-piperidine-4-yl)-piperazine-1-carboxylic acid-[1-(4-methoxy-benzenesulfonyl)-3-(2-ethoxy-phenyl)-5-fluoro-2-oxo-2,3-dihydro-1H-indole-3-yl] amide dihydrochloride $^1$H-NMR (D$_6$-DMSO): δ=1.15 (3H), 1.5 (2H), 2.05 (2H), 2.6 (2H), 2.8 (3H), 3.2-3.8 (11H), 3.85 (4H), 3.95 (1H), 6.95 (2H), 7.1 (2H), 7.15 (2H), 7.3 (1H), 7.4 (1H), 7.7 (1H), 7.75 (1H) and 7.95 (2H) ppm.

Example 124

4-(1-Methyl-piperidine-4-yl)-piperazine-1-carboxylic acid-[3-(2-ethoxy-phenyl)-5-isopropyl-1-(2-methoxy-benzenesulfonyl)-2-oxo-2,3-dihydro-1H-indole-3-yl] ester $^1$H-NMR (CDCl$_3$): δ=1.1-1.3 (9H), 1.55 (2H), 1.7 (2H), 1.9 (2H), 2.15-2.4 (6H), 2.5 (2H), 2.8 (1H), 2.9 (1H), 3.1 (1H), 3.6 (2H), 3.8 (1H), 4.05 (1H), 6.75 (1H), 6.8 (1H), 6.9 (1H), 6.95-7.05 (2H), 7.15 (1H), 7.25 (1H), 7.5 (1H), 7.7 (1H), 7.85 (1H) and 8.15 (1H) ppm.

Example 125

4-(1-Methyl-piperazine-4-yl)-piperidine-1-carboxylic acid-[5-cyano-3-(2-ethoxy-phenyl)-1-(2-methoxy-benzenesulfonyl)-2-oxo-2,3-dihydro-1H-indole-3-yl] amide $^1$H-NMR (CDCl$_3$): δ=1.25-1.45 (2H), 1.45-1.7 (5H), 1.75 (2H), 2.25-2.75 (12H), 3.55 (3H), 3.75 (2H), 4.15 (1H), 4.25 (1H), 6.65 (1H), 6.85 (1H), 6.9 (1H), 6.95 (1H), 7.05 (1H), 7.25 (1H), 7.55 (1H), 7.6 (2H), 8.1 (1H) and 8.15 (1H) ppm.

Example 126

4-(1-Methyl-piperazine-4-yl)-piperidine-1-carboxylic acid-[3-(2-ethoxy-phenyl)-5-fluoro-1-(2-methoxy-benzenesulfonyl)-2-oxo-2,3-dihydro-1H-indole-3-yl] amide $^1$H-NMR (CDCl$_3$): δ=1.4-1.6 (5H), 1.7 (2H), 1.9 (2H), 2.2-2.3 (4H), 2.45 (4H), 3.55 (3H), 4.1-4.3 (2H), 6.75-7.15 (7H), 7.25 (1H), 7.5 (1H), 7.9 (1H) and 8.15 (1H) ppm.

Example 127

4-(1-Methyl-piperidine-4-yl)-piperazine-1-carboxylic acid-[3-(2-ethoxy-phenyl)-5-isopropyl-1-(4-methoxy-benzenesulfonyl)-2-oxo-2,3-dihydro-1H-indole-3-yl] ester $^1$H-NMR (CDCl$_3$): δ=1.15 (6H), 1.2 (3H), 1.55 (2H), 1.75 (2H), 2.0 (2H), 2.2-2.45 (6H), 2.45 (1H), 2.55 (1H), 2.75 (1H), 2.95 (2H), 3.05 (2H), 3.6 (2H), 3.75 (1H), 3.85 (3H), 4.0 (1H), 6.75 (2H), 6.95 (2H), 7.0 (1H), 7.15 (1H), 7.25 (1H), 7.7 (1H), 7.8 (1H) and 8.1 (2H) ppm.

Example 128

4-(1-Methyl-piperazine-4-yl)-piperidine-1-carboxylic acid-[5-cyano-3-(2-ethoxy-phenyl)-1-(2,4-dimethoxy-benzenesulfonyl)-2-oxo-2,3-dihydro-1H-indole-3-yl] amide $^1$H-NMR (CDCl$_3$): δ=1.2 (3H), 1.35 (2H), 1.55 (2H), 1.75 (2H), 2.2-2.8 (12H), 3.5 (3H), 3.75 (2H), 3.85 (3H), 4.15 (1H), 4.2 (1H), 6.4 (1H), 6.55 (1H), 6.7 (1H), 6.85 (1H), 6.9 (1H), 6.95 (1H), 7.25 (1H), 7.6 (2H) and 8.1 (2H) ppm.

Example 129

(−)-4-(1-Methyl-piperidine-4-yl)-piperazine-1-carboxylic acid-[5-cyano-3-(2-ethoxy-phenyl)-1-(2-methoxy-benzenesulfonyl)-2-oxo-2,3-dihydro-1H-indole-3-yl] ester $^1$H-NMR (CDCl$_3$): δ=1.25 (3H), 1.55 (2H), 1.75 (2H), 1.9 (2H), 2.2-2.45 (6H), 2.55 (2H), 2.9 (2H), 3.1 (2H), 3.55-3.7 (5H), 3.8 (1H), 4.1 (1H), 6.8 (1H), 6.95 (1H), 7.0-7.1 (3H), 7.3 (1H), 7.6 (1H), 7.7 (2H) and 8.15 (2H) ppm.

Example 130

(+)-4-(1-Methyl-piperidine-4-yl)-piperazine-1-carboxylic acid-[5-cyano-3-(2-ethoxy-phenyl)-1-(2-methoxy-benzenesulfonyl)-2-oxo-2,3-dihydro-1H-indole-3-yl] ester $^1$H-NMR (CDCl$_3$): δ=1.25 (3H), 1.55 (2H), 1.75 (2H), 1.9 (2H), 2.2-2.45 (6H), 2.55 (2H), 2.9 (2H), 3.1 (2H), 3.55-3.7 (5H), 3.8 (1H), 4.1 (1H), 6.8 (1H), 6.95 (1H), 7.0-7.1 (3H), 7.3 (1H), 7.6 (1H), 7.7 (2H) and 8.15 (2H) ppm.

Example 131

(−)-4-(1-Methyl-piperidine-4-yl)-piperazine-1-carboxylic acid-[5-cyano-3-(2-ethoxy-phenyl)-1-(2,4-dimethoxy-benzenesulfonyl)-2-oxo-2,3-dihydro-1H-indole-3-yl] ester $^1$H-NMR (CDCl$_3$): δ=1.25 (3H), 1.55 (2H), 1.75 (2H), 1.9 (2H), 2.2-2.45 (6H), 2.55 (2H), 2.95 (2H), 3.1 (2H), 3.5-3.7 (5H), 3.8 (1H), 3.85 (3H), 4.05 (1H), 6.4 (1H), 6.55 (1H), 6.8 (1H), 7.0 (1H), 7.3 (2H), 7.65 (2H), 8.05 (1H) and 8.1 (1H) ppm.

Example 132

(+)-4-(1-Methyl-piperidine-4-yl)-piperazine-1-carboxylic acid-[5-cyano-3-(2-ethoxy-phenyl)-1-(2,4-dimethoxy-benzenesulfonyl)-2-oxo-2,3-dihydro-1H-indole-3-yl] ester $^1$H-NMR (CDCl$_3$): δ=1.25 (3H), 1.55 (2H), 1.75 (2H), 1.9 (2H), 2.2-2.45 (6H), 2.55 (2H), 2.95 (2H), 3.1 (2H), 3.5-3.7 (5H), 3.8 (1H), 3.85 (3H), 4.05 (1H), 6.4 (1H), 6.55 (1H), 6.8 (1H), 7.0 (1H), 7.3 (2H), 7.65 (2H), 8.05 (1H) and 8.1 (1H) ppm.

Example 133

4-(4-Methyl-piperazine-1-yl)-piperidine-1-carboxylic acid-[1-benzenesulfonyl-5-cyano-3-(2-ethoxy-phenyl)-2-oxo-2,3-dihydro-1H-indole-3-yl] amide $^1$H-NMR (CDCl$_3$): δ=1.35 (2H), 1.5 (3H), 1.85 (2H), 2.25-2.8 (14H), 3.7 (2H), 4.1 (1H), 4.2 (1H), 6.5 (1H), 6.9 (2H), 7.05 (1H), 7.3 (1H), 7.45-7.7 (5H), 8.05 (1H) and 8.15 (1H) ppm.

Example 134

4-(1-Methyl-piperidine-4-yl)-piperazine-1-carboxylic acid-[1-benzenesulfonyl-3-(2-ethoxy-phenyl)-5-isopropyl-2-oxo-2,3-dihydro-1H-indole-3-yl] ester $^1$H-NMR (CDCl$_3$): δ=1.15 (6H), 1.2 (3H), 1.55 (2H), 1.7 (2H), 1.95 (2H), 2.2-2.4 (5H), 2.45 (1H), 2.55 (1H), 2.75 (1H), 2.9 (2H), 3.05 (2H), 3.6 (2H), 3.75 (1H), 3.95 (1H), 6.8 (2H), 7.0 (1H), 7.2 (1H), 7.3 (2H), 7.5 (2H), 7.6 (1H), 7.75 (1H), 7.8 (1H) and 8.15 (2H) ppm.

Example 135

4-(1-Methyl-piperidine-4-yl)-piperazine-1-carboxylic acid-[4-chloro-3-(2-methoxy-phenyl)-1-(2,4-dimethoxy-benzenesulfonyl)-2-oxo-2,3-dihydro-1H-indole-3-yl] ester $^1$H NMR (CDCl$_3$): δ=1.43-1.94 (7H), 2.24-2.66 (7H), 2.86-3.30 (3H), 3.60 (3H), 3.68 (3H), 3.84 (1H), 6.40 (1H), 6.52 (1H), 6.78 (1H), 6.93 (1H), 7.00 (1H), 7.33-7.20 (m), 7.80 (1H), 7.91 (1H), 8.06 (1H).

Example 136

4-(1-Methyl-piperidine-4-yl)-piperazine-1-carboxylic acid-[4-chloro-3-(2-methoxy-phenyl)-1-(4-methoxy-benzenesulfonyl)-2-oxo-2,3-dihydro-1H-indole-3-yl] ester $^1$H NMR (CDCl$_3$): δ=1.43-2.01 (5H), 2.26-2.56 (6H), 2.63 (1H), 3.10 (2H), 3.25 (1H), 3.50-3.65 (4H), 3.73 (1H), 3.84 (3H), 6.76 (1H), 6.91-7.07 (4H), 7.22-7.37 (m), 7.81 (2H), 8.08 (2H).

Example 137

4-(1-Methyl-piperazine-4-yl)-piperidine-1-carboxylic acid-[3-(2-ethoxy-phenyl)-5-methoxy-1-(2-methoxy-benzenesulfonyl)-2-oxo-2,3-dihydro-1H-indole-3-yl] amide dihydrochloride $^1$H-NMR (D$_6$-DMSO): δ=1.3 (3H), 1.45 (2H), 2.05 (2H), 2.6 (2H), 2.85 (3H), 3.2-3.9 (15H), 3.9-4.2 (4H), 6.8 (2H), 7.0 (3H), 7.15 (1H), 7.2 (1H), 7.3 (1H), 7.6 (1H), 7.7 (2H) and 8.0 (1H) ppm.

Example 138

4-(1-Methyl-piperazine-4-yl)-piperidine-1-carboxylic acid-[3-(2-ethoxy-phenyl)-5-methoxy-1-(2,4-dimethoxy-benzenesulfonyl)-2-oxo-2,3-dihydro-1H-indole-3-yl] amide dihydrochloride $^1$H-NMR (D$_6$-DMSO): δ=1.3 (3H), 1.3-1.6 (2H), 2.05 (2H), 2.65 (2H), 2.8 (3H), 3.2-3.8 (15H), 3.85 (3H), 3.9-4.2 (4H), 6.7 (2H), 6.8 (2H), 6.95 (1H), 7.0 (2H), 7.3 (1H), 7.6 (1H), 7.7 (2H) and 7.9 (1H) ppm.

Example 139

4-(1-Methyl-piperazine-4-yl)-piperidine-1-carboxylic acid-[3-(2-ethoxy-phenyl)-5-methoxy-1-(4-methoxy-benzenesulfonyl)-2-oxo-2,3-dihydro-1H-indole-3-yl] amide dihydrochloride $^1$H-NMR (D$_6$-DMSO): δ=1.2 (3H), 1.35-1.6 (2H), 1.9-2.1 (2H), 2.6 (2H), 2.8 (3H), 3.2-3.8 (12H), 3.8-4.1 (7H), 6.8-6.95 (3H), 6.95 (1H), 7.15 (2H), 7.2-7.3 (2H), 7.6 (1H), 7.7 (1H) and 7.9 (2H) ppm.

Example 140

4-(4-Methyl-piperazine-1-yl)-piperidine-1-carboxylic acid-[1-benzenesulfonyl-3-(2-ethoxy-phenyl)-5-methoxy-2-oxo-2,3-dihydro-1H-indole-3-yl] amide dihydrochloride $^1$H-NMR (D$_6$-DMSO): δ=1.2 (3H), 1.3-1.6 (2H), 1.9-2.1 (2H), 2.6 (2H), 2.8 (3H), 3.2-3.8 (14H), 3.85 (1H), 3.95 (1H), 6.8 (2H), 6.9 (1H), 6.95 (1H), 7.3 (2H), 7.6-7.8 (5H) and 8.0 (2H) ppm.

Example 141

4-(1-Methyl-piperidine-4-yl)-piperazine-1-carboxylic acid-[6-chloro-3-(2-methoxy-phenyl)-1-(4-methoxy-benzenesulfonyl)-2-oxo-2,3-dihydro-1H-indole-3-yl] ester

Example 142

4-(1-Methyl-piperazine-4-yl)-piperidine-1-carboxylic acid-[1-(2,4-dimethoxy-benzenesulfonyl)-3-(2-ethoxy-phenyl)-5-isopropyl-2-oxo-2,3-dihydro-1H-indole-3-yl] ester $^1$H-NMR (D$_6$-DMSO): δ=0.95 (3H), 1.1 (6H), 1.4 (2H), 1.65 (2H), 2.0 (2H), 2.15-2.35 (4H), 2.4 (2H), 2.55 (2H), 2.85 (2H), 2.95 (1H), 3.15 (1H), 3.4 (1H), 3.45 (3H), 3.65 (1H), 3.7 (1H), 3.85 (3H), 3.9 (1H), 6.6 (1H), 6.65 (1H), 6.85 (1H), 6.95 (1H), 7.05 (1H), 7.25 (1H), 7.3 (1H), 7.65 (1H), 7.7 (1H) and 7.85 (1H) ppm.

Example 143

4-Piperidine-4-yl-piperazine-1-carboxylic acid-[5-cyano-1-(2,4-dimethoxy-benzenesulfonyl)-3-(2-ethoxy-phenyl)-2-oxo-2,3-dihydro-1H-indole-3-yl] ester dihydrochloride $^1$H-NMR (D$_6$-DMSO): δ=1.0 (3H), 1.9 (2H), 2.25 (2H), 2.8-3.7 (15H), 3.75 (1H), 3.85 (3H), 3.95 (1H), 4.3 (1H), 6.6-6.7 (2H), 7.0 (1H), 7.1 (2H), 7.35 (1H), 7.65 (1H), 7.8 (1H), 7.85 (1H), 7.95 (2H), 9.0 (NH$^+$) and 11.8 (NH$^+$) ppm.

Example 144

4-(4-Methyl-piperazine-1-yl)-piperidine-1-carboxylic acid-[5-cyano-3-(2-ethoxy-phenyl)-1-(4-methoxy-benzenesulfonyl)-2-oxo-2,3-dihydro-1H-indole-3-yl] amide $^1$H-NMR (CDCl$_3$): δ=1.35 (2H), 1.5 (3H), 1.55 (2H), 1.75 (2H), 2.3-2.5 (4H), 2.5-2.8 (8H), 3.7 (2H), 3.85 (3H), 4.1 (1H), 4.2 (1H), 6.5 (1H), 6.8-7.0 (4H), 7.05 (1H), 7.25 (1H), 7.45 (1H), 7.6 (1H) and 8.0-8.1 (3H) ppm.

Example 145

4-(4-Ethyl-piperidine-1-yl)-piperazine-1-carboxylic acid-[5-cyano-3-(2-ethoxy-phenyl)-1-(2,4-dimethoxy-benzenesulfonyl)-2-oxo-2,3-dihydro-1H-indole-3-yl] ester $^1$H-NMR (CDCl$_3$): δ=1.1 (3H), 1.25 (3H), 1.55 (2H), 1.55 (2H), 1.9 (2H), 2.3 (1H), 2.4 (4H), 2.55 (2H), 2.9-3.2 (4H), 3.55 (3H), 3.6 (2H), 3.8 (1H), 3.85 (3H), 4.05 (1H), 6.4 (1H), 6.55 (1H), 6.8 (1H), 7.00 (1H), 7.2-7.4 (2H), 7.65 (2H), 8.05 (1H) and 8.1 (1H) ppm.

Example 146

4-(4-Propyl-piperidine-1-yl)-piperazine-1-carboxylic acid-[5-cyano-3-(2-ethoxy-phenyl)-1-(2,4-dimethoxy-benzenesulfonyl)-2-oxo-2,3-dihydro-1H-indole-3-yl] ester $^1$H-NMR (CDCl$_3$): δ=0.9 (3H), 1.25 (3H), 1.4-1.6 (4H), 1.7 (2H), 1.9 (2H), 2.25 (3H), 2.35 (2H), 2.55 (2H), 2.95 (2H), 3.15 (2H), 3.55 (3H), 3.6 (2H), 3.8 (1H), 3.85 (3H), 4.05 (1H), 6.4 (1H), 6.55 (1H), 6.8 (1H), 7.00 (1H), 7.2-7.4 (2H), 7.6-7.75 (2H), 8.05 (1H) and 8.15 (1H) ppm.

Example 147

4-(4-Isopropyl-piperidine-1-yl)-piperazine-1-carboxylic acid-[5-cyano-3-(2-ethoxy-phenyl)-1-(2,4-dimethoxy-benzenesulfonyl)-2-oxo-2,3-dihydro-1H-indole-3-yl] ester $^1$H-NMR (CDCl$_3$): δ=1.25 (3H), 1.45 (6H), 1.6 (2H), 1.9 (2H), 2.3-2.8 (8H), 3.1-3.3 (2H), 3.4-3.8 (7H), 3.8 (1H), 3.85 (3H), 4.05 (1H), 6.4 (1H), 6.55 (1H), 6.8 (1H), 7.0 (1H), 7.2-7.4 (2H), 7.6-7.75 (2H), 8.05 (1H) and 8.15 (1H) ppm.

Example 148

4-(4-Methyl-piperidine-1-yl)-piperazine-1-carboxylic acid-[4-methyl-3-(2-ethoxy-phenyl)-1-(2,4-dimethoxy-benzenesulfonyl)-2-oxo-2,3-dihydro-1H-indole-3-yl] ester

Example 149

4-(4-Methyl-piperidine-1-yl)-piperazine-1-carboxylic acid-[5-cyano-3-(2-ethoxy-phenyl)-1-(3,4-dibromo-benzenesulfonyl)-2-oxo-2,3-dihydro-1H-indole-3-yl] ester $^1$H-NMR (CDCl$_3$): δ=1.25 (3H), 1.55 (2H), 1.75 (2H), 1.95 (2H), 2.2-2.6 (8H), 2.9 (2H), 3.0 (2H), 3.5 (1H), 3.65 (1H), 3.8 (1H), 4.0 (1H), 6.8 (1H), 7.05 (1H), 7.25 (1H), 7.35 (1H), 7.6-7.8 (3H), 7.85 (1H), 8.0 (1H) and 8.3 (1H) ppm.

Example 150

4-(4-Methyl-piperidine-1-yl)-piperazine-1-carboxylic acid-[4-methoxy-3-(2-methoxy-phenyl)-1-(2-methoxy-benzenesulfonyl)-2-oxo-2,3-dihydro-1H-indole-3-yl] ester

Example 151

4-(4-Methyl-piperidine-1-yl)-piperazine-1-carboxylic acid-[4-methoxy-3-(2-methoxy-phenyl)-1-(2,4-dimethoxy-benzenesulfonyl)-2-oxo-2,3-dihydro-1H-indole-3-yl] ester

Example 152

4-(4-Methyl-piperidine-1-yl)-piperazine-1-carboxylic acid-[5-methoxy-3-(2-ethoxy-phenyl)-1-(2,4-dimethoxy-benzenesulfonyl)-2-oxo-2,3-dihydro-1H-indole-3-yl] ester $^1$H-NMR (CDCl$_3$): δ=1.25 (3H), 1.55 (2H), 1.7 (2H), 1.9 (2H), 2.2-2.3 (4H), 2.4 (2H), 2.5 (2H), 2.9 (2H), 3.1 (2H), 3.6 (4H), 3.7 (3H), 3.75 (1H), 3.8 (3H), 4.05 (1H), 6.4 (1H), 6.5-6.6 (2H), 6.75 (1H), 6.8 (1H), 6.95 (1H), 7.25 (1H), 7.65 (1H), 7.85 (1H) and 8.05 (1H) ppm.

Example 153

4-piperazine-1-yl-piperidine-1-carboxylic acid-[5-cyano-1-(2,4-dimethoxy-benzenesulfonyl)-3-(2-ethoxy-phenyl)-2-oxo-2,3-dihydro-1H-indole-3-yl] amide dihydrochloride $^1$H-NMR (D$_6$-DMSO): δ=1.25 (3H), 1.45 (2H), 2.0 (2H), 2.65 (2H), 3.2-3.8 (13H), 3.8-4.1 (6H), 6.6-6.75 (2H), 6.9 (1H), 7.0 (1H), 7.25-7.4 (2H), 7.7 (1H), 7.8 (2H), 7.9 (2H), 9.4 (NH$^+$), 9.6 (NH$^+$) and 11.9 (NH$^+$) ppm.

Example 154

4-(4-Ethyl-piperazine-1-yl)-piperidine-1-carboxylic acid-[5-cyano-1-(2,4-dimethoxy-benzenesulfonyl)-3-(2-ethoxy-phenyl)-2-oxo-2,3-dihydro-1H-indole-3-yl] amide $^1$H-NMR (CDCl$_3$). δ=1.2-1.4 (5H), 1.5 (3H), 1.75 (2H), 2.4 (1H), 2.5-2.8 (12H), 3.5 (3H), 3.75 (2H), 3.85 (3H), 4.15 (1H), 4.2 (1H), 6.4 (1H), 6.55 (1H), 6.7 (1H), 6.85 (1H), 6.9 (1H), 6.95 (2H), 7.25 (1H), 7.6 (2H) and 8.1 (2H) ppm.

Example 155

4-(4-Propyl-piperazine-1-yl)-piperidine-1-carboxylic acid-[5-cyano-1-(2,4-dimethoxy-benzenesulfonyl)-3-(2-ethoxy-phenyl)-2-oxo-2,3-dihydro-1H-indole-3-yl] amide $^1$H-NMR (D$_6$-DMSO): δ=0.9 (3H), 1.15 (3H), 1.45 (2H), 1.7 (2H), 2.0 (2H), 2.65 (2H), 3.05 (2H), 3.25-3.8 (12H), 3.8-4.1 (7H), 6.7 (2H), 6.9 (1H), 6.95 (1H), 7.3 (2H), 7.7 (1H), 7.8 (2H) and 7.9 (2H) ppm.

Example 156

4-(4-Propyl-piperazine-1-yl-piperidine-1-carboxylic acid-[5-cyano-1-benzenesulfonyl-3-(2-ethoxy-phenyl)-2-oxo-2,3-dihydro-1H-indole-3-yl] amide $^1$H-NMR (CDCl$_3$): δ=0.9 (3H), 1.35 (2H), 1.45-1.55 (5H), 1.75 (2H), 2.3 (3H), 2.4-2.8 (10H), 3.7 (2H), 4.1 (1H), 4.2 (1H), 6.45 (1H), 6.9 (2H), 7.1 (1H), 7.3 (1H), 7.5 (3H), 7.55-7.7 (2H), 8.0 (1H) and 8.1 (2H) ppm.

Example 157

4-(4-Propyl-piperazine-1-yl)-piperidine-1-carboxylic acid-[5-cyano-1-(2-methoxy-benzenesulfonyl)-3-(2-ethoxy-phenyl)-2-oxo-2,3-dihydro-1H-indole-3-yl] amide $^1$H-NMR (CDCl$_3$): δ=0.9 (3H), 1.35 (2H), 1.45-1.6 (5H), 1.75 (2H), 2.25-2.4 (3H), 2.4-2.65 (8H), 2.65 (2H), 3.5 (3H), 3.75 (2H), 4.15 (1H), 4.2 (1H), 6.65 (1H), 6.85 (1H), 6.9 (1H), 6.95 (1H), 7.05 (1H), 7.25 (1H), 7.55 (1H), 7.6 (2H), 8.1 (1H) and 8.15 (1H) ppm.

Example 158

4-(4-Isopropyl-piperazine-1-yl)-piperidine-1-carboxylic acid-[5-cyano-1-(2,4-dimethoxy-benzenesulfonyl)-3-(2-ethoxy-phenyl)-2-oxo-2,3-dihydro-1H-indole-3-yl] amide dihydrochloride $^1$H-NMR (D$_6$-DMSO): δ=1.1 (3H), 1.25 (6H), 1.45 (2H), 2.0 (2H), 2.65 (2H), 3.3-3.8 (13H), 3.8-4.1 (7H), 6.7 (2H), 6.95 (1H), 7.0 (1H), 7.3 (2H), 7.7 (1H), 7.8 (2H) and 7.9 (2H) ppm.

Example 159

4-(4-Propyl-piperazine-1-yl)-piperidine-1-carboxylic acid-[5-cyano-1-(2,4-difluoro-benzenesulfonyl)-3-(2-ethoxy-phenyl)-2-oxo-2,3-dihydro-1H-indole-3-yl] ester $^1$H-NMR (CDCl$_3$): δ=0.9 (3H), 1.1 (1H), 1.25 (3H), 1.35 (1H), 1.4-1.65 (4H), 1.7 (1H), 1.85 (1H), 2.25-2.75 (10H), 2.95 (1H), 3.55 (1H), 3.8 (1H), 4.05 (1H), 4.2 (1H), 6.8 (1H), 6.9 (1H), 7.0 (2H), 7.25 (1H), 7.3 (1H), 7.7 (2H) and 8.1-8.25 (2H) ppm.

Example 160

4-(4-Propyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] ester $^1$H-NMR (CDCl$_3$): δ=0.9 (3H), 1.1-1.35 (4H), 1.4-1.75 (6H), 1.85 (1H), 2.25-2.75 (10H), 2.95 (1H), 3.55 (1H), 3.8 (1H), 3.85 (3H), 4.0 (1H), 4.2 (1H), 6.8 (1H), 6.95 (2H), 7.05 (1H), 7.25 (1H), 7.3 (1H), 7.65 (1H), 7.7 (1H) and 8.05 (3H) ppm.

Example 161

4-(4-Propyl-piperazine-1-yl)-piperidine-1-carboxylic acid-[5-cyano-1-(2-fluoro-benzenesulfonyl)-3-(2-ethoxy-phenyl)-2-oxo-2,3-dihydro-1H-indole-3-yl] ester $^1$H-NMR (CDCl$_3$): δ=0.9 (3H), 1.1 (1H), 1.3 (3H), 1.35-1.75 (4H), 1.75-1.95 (1H), 2.25-2.75 (12H), 2.9 (1H), 3.55 (1H), 3.8 (1H), 4.0 (1H), 4.2 (1H), 6.8 (1H), 7.0 (1H), 7.15 (1H), 7.2-7.4 (3H), 7.6 (1H), 7.7 (2H) and 8.15 (2H) ppm.

Example 162

4-(4-Propyl-piperazine-1-yl)-piperidine-1-carboxylic acid-[5-cyano-1-benzenesulfonyl-3-(2-ethoxy-phenyl)-2-oxo-2,3-dihydro-1H-indole-3-yl] ester $^1$H-NMR (CDCl$_3$): δ=0.9 (3H), 1.2 (1H), 1.25 (3H), 1.35-1.75 (6H), 1.85 (1H), 2.25-2.75 (10H), 2.95 (1H), 3.5 (1H), 3.8 (1H), 4.0 (1H), 4.2 (1H), 6.8 (1H), 7.0 (1H), 7.25 (1H), 7.3 (1H), 7.5 (2H), 7.65 (2H), 7.7 (1H) and 8.05-8.2 (3H) ppm.

Example 163

4-(4-Propyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] amide $^1$H-NMR (CDCl$_3$): δ=0.9 (3H), 1.35 (2H), 1.45-1.6 (5H), 1.75 (2H), 2.3 (2H), 2.35 (1H), 2.4-2.8 (10H), 3.7 (2H), 3.85 (3H), 4.1 (1H), 4.2 (1H), 6.5 (1H), 6.85-7.0 (4H), 7.1 (1H), 7.3 (1H), 7.5 (1H), 7.6 (1H), 8.05 (1H) and 8.1 (2H) ppm.

Example 164

4-(4-Propyl-piperazine-1-yl)-piperidine-1-carboxylic acid-[5-cyano-1-(2-fluoro-benzenesulfonyl)-3-(2-ethoxy-phenyl)-2-oxo-2,3-dihydro-1H-indole-3-yl] amide $^1$H-NMR (CDCl$_3$): δ=0.9 (3H), 1.25 (1H), 1.35 (1H), 1.45-1.65 (5H), 1.75 (2H), 2.2-2.35 (3H), 2.35-2.8 (10H), 3.7 (2H), 4.1 (1H), 4.2 (1H), 6.45 (1H), 6.9 (2H), 7.1 (1H), 7.15 (1H), 7.3 (2H), 7.5 (1H), 7.55-7.65 (2H), 8.1 (1H) and 8.15 (1H) ppm.

Example 165

4-(4-Propyl-piperazine-1-yl)-piperidine-1-carboxylic acid-[5-cyano-1-(2,4-difluoro-benzenesulfonyl)-3-(2-ethoxy-phenyl)-2-oxo-2,3-dihydro-1H-indole-3-yl] amide $^1$H-NMR (CDCl$_3$): δ=0.9 (3H), 1.25 (1H), 1.35 (1H), 1.45-1.65 (5H), 1.75 (2H), 2.2-2.35 (3H), 2.4-2.8 (10H), 3.7 (2H), 4.1 (1H), 4.2 (1H), 6.4 (1H), 6.8-7.05 (4H), 7.15 (1H), 7.3 (1H), 7.5 (1H), 7.6 (1H), 8.1 (1H) and 8.15 (1H) ppm.

Example 166

4-(4-Propyl-piperazine-1-yl)-piperidine-1-carboxylic acid-[5-cyano-1-(2-methoxy-benzenesulfonyl)-3-(2-ethoxy-phenyl)-2-oxo-2,3-dihydro-1H-indole-3-yl] ester $^1$H-NMR (CDCl$_3$): δ=0.9 (3H), 1.1 (1H), 1.25 (3H), 1.4-1.95 (10H), 2.25-2.75 (11H), 2.95 (1H), 3.55 (4H), 3.8 (1H), 4.05 (1H), 4.2 (1H), 6.8 (1H), 6.95 (1H), 7.05 (2H), 7.25 (1H), 7.3 (1H), 7.55 (1H), 7.65 (2H) and 8.1 (2H) ppm.

Example 167

4-(4-Methyl-piperazine-1-yl)-piperidine-1-carboxylic acid-[5-cyano-1-benzenesulfonyl-3-(2-ethoxy-phenyl)-2-oxo-2,3-dihydro-1H-indole-3-yl] ester dihydrochloride $^1$H-NMR (D$_6$-DMSO): δ=0.95 (3H), 1.35 (1H), 1.6 (1H), 1.95 (1H), 2.1 (2H), 2.6 (2H), 2.8 (3H), 3.0 (1H), 3.2-3.9 (12H), 4.25 (1H), 6.95 (1H), 7.1 (1H), 7.4 (1H), 7.6-7.75 (3H), 7.8 (2H), 7.9 (2H), 8.0 (1H) and 8.05 (1H) ppm.

Example 168

4-(4-Methyl-piperazine-1-yl)-piperidine-1-carboxylic acid-[5-cyano-1-(2,4-difluoro-benzenesulfonyl)-3-(2-ethoxy-phenyl)-2-oxo-2,3-dihydro-1H-indole-3-yl] ester dihydrochloride $^1$H-NMR (D$_6$-DMSO): δ=1.2 (3H), 1.35-1.7 (2H), 1.85-2.2 (2H), 2.6 (1H), 2.8 (3H), 3.0 (1H), 3.2-3.8 (11H), 3.95 (1H), 4.25 (1H), 7.0 (1H), 7.1 (1H), 7.3-7.5 (2H), 7.5-7.7 (2H), 7.8 (1H), 7.95 (2H) and 8.1 (1H) ppm.

Example 169

4-(4-Methyl-piperazine-1-yl)-piperidine-1-carboxylic acid-[5-cyano-1-(2-fluoro-benzenesulfonyl)-3-(2-ethoxy-phenyl)-2-oxo-2,3-dihydro-1H-indole-3-yl] ester $^1$H-NMR (CDCl$_3$): δ=1.25 (3H), 1.3-1.9 (5H), 2.25-2.7 (12H), 2.9 (1H), 3.55 (1H), 3.8 (1H), 4.05 (1H), 4.2 (1H), 6.8 (1H), 7.05 (1H), 7.15 (1H), 7.2-7.4 (3H), 7.6 (1H), 7.7 (2H) and 8.15 (2H) ppm.

Example 170

4-(4-Methyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] ester $^1$H-NMR (CDCl$_3$): δ=1.15-1.3 (4H), 1.4-1.9 (4H), 2.3-2.75 (12H), 2.95 (1H), 3.55 (1H), 3.8 (1H), 3.85 (3H), 3.95 (1H), 4.2 (1H), 6.8 (1H), 6.95 (2H), 7.05 (1H), 7.25 (1H), 7.3 (1H), 7.65 (1H), 7.7 (1H) and 8.05 (3H) ppm.

Example 171

4-(4-Methyl-piperazine-1-yl)-piperidine-1-carboxylic acid-[5-cyano-1-(2-methoxy-benzenesulfonyl)-3-(2-ethoxy-phenyl)-2-oxo-2,3-dihydro-1H-indole-3-yl] ester $^1$H-NMR (CDCl$_3$): δ=1.1 (1H), 1.25 (3H), 1.3-1.9 (4H), 2.25-3.2 (12H), 2.95 (1H), 3.5-3.65 (4H), 3.8 (1H), 4.05 (1H), 4.2 (1H), 6.8 (1H), 6.9 (1H), 7.0-7.1 (2H), 7.3 (1H), 7.55 (1H), 7.65 (2H) and 8.1 (2H) ppm.

Example 172

4-(4-Methyl-piperazine-1-yl)-piperidine-1-carboxylic acid-[5-cyano-1-(2,4-dimethoxy-benzenesulfonyl)-3-(2-ethoxy-phenyl)-2-oxo-2,3-dihydro-1H-indole-3-yl] ester dihydrochloride $^1$H-NMR (CF$_3$COOD): δ=0.5 (3H), 1.8 (2H), 2.0 (2H), 2.5 (3H), 2.75 (2H), 3.05 (3H), 3.1-3.6 (16H), 6.0 (1H), 6.1 (1H), 6.2 (1H), 6.45 (1H), 6.75 (1H), 7.2 (1H), 7.35 (1H), 7.4 (1H) and 7.5 (1H) ppm.

Example 173

4-(4-Propargyl-3-yl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] ester $^1$H-NMR (CDCl$_3$): δ=1.3-1.5 (2H), 1.5 (3H), 1.7-1.85 (2H), 2.25 (1H), 2.5-2.8 (10H), 3.3 (2H), 3.5 (3H), 3.8 (2H), 3.85 (3H), 4.1-4.3 (2H), 6.4 (1H), 6.55 (1H), 6.7 (1H), 6.85 (1H), 6.9-7.0 (2H), 7.3 (1H), 7.6 (2H) and 8.1 (2H) ppm.

Example 174

4-(4-Isopropyl-piperazine-1-yl)-piperidine-1-carboxylic acid-[5-cyano-1-benzenesulfonyl-3-(2-ethoxy-phenyl)-2-oxo-2,3-dihydro-1H-indole-3-yl] ester $^1$H-NMR (CDCl$_3$): δ=1.1 (6H), 1.2 (3H), 1.35-1.75 (5H), 1.75-1.95 (1H), 2.25-2.8 (9H), 2.95 (1H), 3.5 (2H), 3.8 (1H), 4.0 (1H), 4.2 (1H), 6.8 (1H), 7.05 (1H), 7.2 (1H), 7.35 (1H), 7.5 (1H), 7.6-7.7 (3H) and 8.05-8.15 (3H) ppm.

Example 175

4-(4-Isopropyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] ester $^1$H-NMR (CDCl$_3$): δ=1.1 (6H), 1.25 (3H), 1.35-1.75 (5H), 1.75-1.95 (1H), 2.35 (1H), 2.4-2.8 (8H), 2.95 (1H), 3.55 (1H), 3.75 (1H), 3.85 (3H), 4.0 (1H), 4.2 (1H), 6.8 (1H), 6.95 (2H), 7.05 (1H), 7.2 (1H), 7.3 (1H), 7.65 (1H), 7.7 (1H) and 8.05-8.15 (3H) ppm.

Example 176

4-(4-Allyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] ester $^1$H-NMR (CDCl$_3$): δ=1.3-1.5 (2H), 1.5-1.7 (5H), 1.7-1.85 (2H), 2.3-2.8 (9H), 3.05 (2H), 3.5 (3H), 3.75 (2H), 3.85 (3H), 4.1-4.3 (2H), 5.1-5.3 (2H), 5.9 (1H), 6.4 (1H), 6.55 (1H), 6.7 (1H), 6.85 (1H), 6.9 (1H), 6.95 (1H), 7.25 (1H), 7.6 (2H) and 8.1 (2H) ppm.

Example 177

4-(4-Isopropyl-piperazine-1-yl)-piperidine-1-carboxylic acid-[5-cyano-1-(2-methoxy-benzenesulfonyl)-3-(2-ethoxy-phenyl)-2-oxo-2,3-dihydro-1H-indole-3-yl] ester $^1$H-NMR (CDCl$_3$): δ=1.1 (6H), 1.25 (3H), 1.35-1.95 (6H), 2.35 (1H), 2.4-2.8 (9H), 2.95 (1H), 3.55 (3H), 3.8 (1H), 4.05 (1H), 4.2 (1H), 6.8 (1H), 6.95 (1H), 7.0-7.1 (2H), 7.25 (1H), 7.3 (1H), 7.55 (1H), 7.7 (2H) and 8.1 (2H) ppm.

Example 178

4-(4-Ethyl-piperazine-1-yl)-piperidine-1-carboxylic acid-[5-cyano-1-benzenesulfonyl-3-(2-ethoxy-phenyl)-2-oxo-2,3-dihydro-1H-indole-3-yl] amide $^1$H-NMR (CDCl$_3$): δ=1.1 (3H), 1.35 (2H), 1.5 (3H), 1.75 (2H), 2.25-2.8 (13H), 3.8 (2H), 4.1 (1H), 4.2 (1H), 6.45 (1H), 6.9 (2H), 7.1 (2H), 7.3 (1H), 7.5 (3H), 7.55-7.7 (2H), 8.0 (1H) and 8.15 (2H) ppm.

Example 179

4-(4-Ethyl-piperazine-1-yl)-piperidine-1-carboxylic acid-[5-cyano-1-(2-methoxy-benzenesulfonyl)-3-(2-ethoxy-phenyl)-2-oxo-2,3-dihydro-1H-indole-3-yl] amide $^1$H-NMR (CDCl$_3$): δ=1.1 (3H), 1.35 (2H), 1.5 (3H), 1.75 (2H), 2.25-2.8 (13H), 3.55 (3H), 3.75 (2H), 4.15 (1H), 4.25 (1H), 6.65 (1H), 6.85 (1H), 6.9 (2H), 6.95 (1H), 7.05 (1H), 7.3 (1H), 7.55 (1H), 7.6 (2H), 8.1 (1H) and 8.15 (1H) ppm.

Example 180

4-(4-Ethyl-piperazine-1-yl)-piperidine-1-carboxylic acid-[5-cyano-1-(2-fluoro-benzenesulfonyl)-3-(2-ethoxy-phenyl)-2-oxo-2,3-dihydro-1H-indole-3-yl] amide $^1$H-NMR (CDCl$_3$): δ=1.1 (3H), 1.25 (1H), 1.35 (1H), 1.5 (3H), 1.55 (2H), 1.75 (2H), 2.25-2.8 (13H), 3.5 (3H), 3.7

(2H), 4.1 (1H), 4.2 (1H), 6.45 (1H), 6.9 (2H), 7.1 (1H), 7.15 (1H), 7.3 (2H), 7.5 (1H), 7.6 (2H), 8.1 (1H) and 8.15 (1H) ppm.

Example 181

4-(4-Propyl-piperazine-1-yl)-piperidine-1-carboxylic acid-[5-cyano-1-(2,4-dimethoxy-benzenesulfonyl)-3-(2-isopropoxy-phenyl)-2-oxo-2,3-dihydro-1H-indole-3-yl] amide $^1$H-NMR (CDCl$_3$): δ=0.9 (3H), 1.25-1.4 (5H), 1.45-1.65 (5H), 1.75 (2H), 2.25-2.8 (13H), 3.5 (3H), 3.7 (2H), 3.9 (3H), 4.75 (1H), 6.4 (1H), 6.55 (1H), 6.65 (1H), 6.85 (1H), 6.9 (1H), 7.0 (1H), 7.25 (1H), 7.6 (1H), 7.65 (1H) and 8.1 (2H) ppm.

Example 182

4-(4-Propyl-piperazine-1-yl)-piperidine-1-carboxylic acid-[5-cyano-1-(2-methoxy-benzenesulfonyl)-3-(2-isopropoxy-phenyl)-2-oxo-2,3-dihydro-1H-indole-3-yl] amide $^1$H-NMR (CDCl$_3$): δ=0.9 (3H), 1.25-1.4 (5H), 1.45-1.65 (5H), 1.75 (2H), 2.25-2.8 (13H), 3.5 (3H), 3.75 (2H), 4.75 (1H), 6.65 (1H), 6.85 (1H), 6.9 (2H), 7.0 (1H), 7.05 (1H), 7.25 (1H), 7.55 (1H), 7.6 (1H), 7.65 (1H), 8.1 (1H) and 8.1 (1H) ppm.

Example 183

4-(4-Propyl-piperazine-1-yl)-piperidine-1-carboxylic acid-[5-cyano-1-(4-methoxy-benzenesulfonyl)-3-(2-isopropoxy-phenyl)-2-oxo-2,3-dihydro-1H-indole-3-yl] amide $^1$H-NMR (CDCl$_3$): δ=0.9 (3H), 1.3 (3H), 1.35 (2H), 1.45 (3H), 1.5 (2H), 1.75 (2H), 2.25-2.8 (13H), 3.7 (2H), 3.85 (3H), 4.7 (1H), 6.4 (1H), 6.8-7.0 (4H), 7.1 (1H), 7.25 (1H), 7.5 (1H), 7.6 (1H) and 8.0-8.1 (3H) ppm.

Example 184

4-(4-Propyl-piperazine-1-yl)-piperidine-1-carboxylic acid-[5-cyano-1-(4-fluoro-benzenesulfonyl)-3-(2-isopropoxy-phenyl)-2-oxo-2,3-dihydro-1H-indole-3-yl] amide $^1$H-NMR (CDCl$_3$): δ=0.9 (3H), 1.25-1.4 (5H), 1.4-1.65 (5H), 1.75 (2H), 2.25-2.8 (13H), 3.7 (2H), 4.7 (1H), 6.35 (1H), 6.8 (2H), 7.1-7.2 (3H), 7.3 (1H), 7.45 (1H), 7.6 (1H), 8.05 (1H) and 8.1 (2H) ppm.

Example 185

4-(4-Isopropyl-piperazine-1-yl)-piperidine-1-carboxylic acid-[5-cyano-1-(2,4-dimethoxy-benzenesulfonyl)-3-(2-ethoxy-phenyl)-2-oxo-2,3-dihydro-1H-indole-3-yl] ester $^1$H-NMR (CDCl$_3$): δ=1.1 (6H), 1.15-1.35 (4H), 1.4-1.7 (1H), 1.7-1.9 (2H), 2.4 (1H), 2.45-2.8 (10H), 2.95 (1H), 3.5 (3H), 3.6 (1H), 3.8 (1H), 3.85 (3H), 4.05 (1H), 4.2 (1H), 6.4 (1H), 6.55 (1H), 6.75 (1H), 7.0 (1H), 7.2-7.35 (2H), 7.6-7.7 (2H), 8.05 (1H) and 8.1 (1H) ppm.

Example 186

4-(4-Isopropyl-piperazine-1-yl)-piperidine-1-carboxylic acid-[5-cyano-1-(2,4-difluoro-benzenesulfonyl)-3-(2-ethoxy-phenyl)-2-oxo-2,3-dihydro-1H-indole-3-yl] ester $^1$H-NMR (CDCl$_3$): δ=1.1 (6H), 1.25 (3H), 1.4-1.95 (4H), 2.35 (1H), 2.4-2.9 (10H), 2.95 (1H), 3.5 (1H), 3.8 (1H), 4.0 (1H), 4.2 (1H), 6.8 (1H), 6.9 (1H), 7.0 (2H), 7.25 (1H), 7.3 (1H), 7.7 (2H) and 8.15 (2H) ppm.

Example 187

4-(4-Isopropyl-piperazine-1-yl)-piperidine-1-carboxylic acid-[5-cyano-1-(2-fluoro-benzenesulfonyl)-3-(2-ethoxy-phenyl)-2-oxo-2,3-dihydro-1H-indole-3-yl] ester $^1$H-NMR (CDCl$_3$): δ=1.1 (6H), 1.25 (3H), 1.35-1.95 (6H), 2.35-3.05 (10H), 3.5 (1H), 3.8 (1H), 4.0 (1H), 4.2 (1H), 6.8 (1H), 7.0 (1H), 7.15 (1H), 7.2-7.4 (3H), 7.6 (1H), 7.65 (2H) and 8.15 (2H) ppm.

Example 188

4-(4-Isopropyl-piperazine-1-yl)-piperidine-1-carboxylic acid-[5-cyano-1-(4-fluoro-benzenesulfonyl)-3-(2-ethoxy-phenyl)-2-oxo-2,3-dihydro-1H-indole-3-yl] ester $^1$H-NMR (CDCl$_3$): δ=1.1 (6H), 1.25 (3H), 1.35-1.95 (4H), 2.35 (1H), 2.4-2.8 (10H), 2.95 (1H), 3.5 (1H), 3.8 (1H), 4.0 (1H), 4.2 (1H), 6.8 (1H), 7.05 (1H), 7.15-7.4 (4H), 7.6-7.75 (2H) and 8.1-8.2 (3H) ppm.

Example 189

4-(4-Propyl-piperazine-1-yl)-piperidine-1-carboxylic acid-[5-cyano-1-(4-fluoro-benzenesulfonyl)-3-(2-ethoxy-phenyl)-2-oxo-2,3-dihydro-1H-indole-3-yl] ester $^1$H-NMR (CDCl$_3$): δ=0.9 (3H), 1.1-1.35 (4H), 1.35-1.8 (5H), 1.9 (1H), 2.2-2.85 (11H), 2.95 (1H), 3.5 (1H), 3.8 (1H), 4.0 (1H), 4.2 (1H), 6.8 (1H), 7.05 (1H), 7.15-7.3 (3H), 7.35 (1H), 7.6-7.75 (2H) and 8.0-8.15 (3H) ppm.

Example 190

3-(2-Ethoxy-phenyl)-1-benzenesulfonyl-2-oxo-3-{2-oxo-2-[4-(4-propyl-piperazine-1-yl)-piperidine-1-yl]-ethyl}-2,3-dihydro-1H-indole-5-carboxylic-acid nitrile $^1$H-NMR (CDCl$_3$): δ=0.9 (3H), 1.0-1.2 (1H), 1.2-1.35 (3H), 1.35 (1H), 1.45-1.8 (4H), 1.85 (1H), 2.2 (1H), 2.25-2.8 (10H), 2.9 (1H), 3.3 (1H), 3.65 (1H), 3.75-4.1 (4H), 6.8 (1H), 6.95 (1H), 7.25 (2H), 7.35 (1H), 7.45-7.7 (4H), 8.05 (1H) and 8.15 (2H) ppm.

Example 191

3-(2-Ethoxy-phenyl)-1-(2-methoxy-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile $^1$H-NMR (CDCl$_3$): δ=0.9 (3H), 1.2 (1H), 1.4 (4H), 1.5-1.9 (5H), 2.2-2.75 (11H), 2.9 (1H), 3.25 (1H), 3.6 (3H), 3.75-3.85

(2H), 3.9-4.05 (2H), 4.15 (1H), 6.75-6.95 (3H), 7.05 (1H), 7.15-7.3 (3H), 7.5-7.65 (2H), 8.1 (1H) and 8.15 (1H) ppm.

Example 192

3-(2-Ethoxy-phenyl)-1-(4-methoxy-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile a) 4-(4-Propyl-piperazine-1-yl)-piperidine-1-carboxylic acid-tert-butylester 42 g (0.50 mol) sodium acetate were added in portions to 73 g (0.25 mol) N-propylpiperazine dihydrobromide in 1 l methanol at 40° C. Subsequently, this was cooled to 0° C. and 50 g (0.25 mol) Boc-4-piperidon and 16 g (0.25 mol) sodium cyanoborohydride, in portions, were added, one after the other. Everything was then stirred at room temperature for 16 h. The reaction mixture was concentrated in a vacuum and then distributed between ethyl acetate and 1M NaOH. The organic phase was separated, washed with 1M NaOH, $H_2O$ and conc. NaCl solution, dried and concentrated in a vacuum. The residue was chromatographically purified over silica gel (mobile phase: $MeOH/CH_2Cl_2=1/15$). 43.6 g of the product were obtained.

b) 1-Piperidine-4-yl-4-propyl-piperazine trihydrochloride 43.5 g (0.14 mol) of the intermediate product 192a were dissolved in 500 ml methanol and then 100 ml 5-6 M isopropanolic HCl were slowly added at 40° C., wherein intermittently a powerful gas development began and the product partially crystallised. The gas development had ended after 30 minutes. After this, another 50 ml 5-6 M isopropanolic HCl were added, and everything was stirred for 1 h at 40° C. It was allowed to cool, and the precipitated product was isolated. 34 g of the product were obtained.

c) 3-(2-Ethoxy-phenyl)-3-hydroxy-5-iodo-1,3-dihydro-indole-2-one 8.0 g (1.65 mol) magnesium shavings were overlaid with 40 ml ether, and after the addition of a small quantity iodine, were carefully heated until the reaction kicked off. 66.3 g (0.33 mol) 2-bromo-1-ethoxybenzene dissolved in 200 ml ether was dropped in to the boiling solution so slowly that the reaction continually proceeded at a low boil. Subsequently, with slight cooling to 20° C., 30 g (0.11 mol) 5-iodine-isatin in 800 ml water-free tetrahydrofurane was added in by drops. After this, everything was stirred for 30 minutes more at room temperature. The reaction solution was poured into an aqueous $NH_4Cl$ solution while being stirred. This aqueous phase was extracted a number of times with ethyl acetate and the combined aqueous phases were washed with water four times, dried and concentrated in a vacuum, after which a solid precipitated slowly, which was isolated and dried. 33.6 g of the intermediate product were obtained.

d) 3-(2-Ethoxy-phenyl)-3-hydroxy-2-oxo-2,3-dihydro-1H-indole-5-carboxylic-acid nitrile 37 g (94 mmol) of the intermediate product 192c and 11 g (94 mmol) zinc cyanide were placed in 300 ml DMF and all were rapidly heated to 90-95° C. After this, 1.6 g (1.4 mmol) $Pd[Ph_3P]_4$ were added in two portions within 20 minutes. After an additional 30 minutes, the reaction mixture was poured on to icy water and extracted with ethyl acetate. The organic phase was washed with water and saturated NaCl in isolation, dried and concentrated in a vacuum. The residue obtained was crystallised from a little ethyl acetate and the crystals were isolated. 24 g of the product were obtained.

e) 3-Chloro-3-(2-ethoxy-phenyl)-2-oxo-2,3-dihydro-1H-indole-5-carboxylic-acid nitrile 10 g (34 mmol) of the intermediate product 192d and 5.6 ml (68 mmol) pyridine were dissolved in 120 ml $CH_2Cl_2$. After this, everything was cooled to 0° C. and 3.7 ml (51 mmol) $SOCl_2$ were added by drops. The reaction mixture was stirred for 1 h more. Then everything was carefully placed in icy water, the organic phase was separated, washed a number of times with $H_2O$, dried and concentrated in a vacuum. The residue obtained was treated with n-pentane and the resulting solid was isolated, after which 9.9 g of the product were obtained.

f) 2-[5-Cyano-3-(2-ethoxy-phenyl)-2-oxo-2,3-dihydro-1H-indole-3-yl]-malonic acid dimethylester 3.8 g (96 mmol) NaH (60%) were carefully added to 200 ml water-free DMF. Then 12 ml (105 mmol) malonic acid dimethylester were added slowly by drops at 10° C. Everything was stirred for 30 minutes more at room temperature. Subsequently, 10 g (32 mmol) of the intermediate product 192e was added in portions and the reaction mixture was stirred for 15 minutes more. This mixture was carefully mixed in by stirring to 1 M HCl and then everything was cooled, wherein a precipitate resulted, which was isolated and recrystallised from $CH_2Cl_2$/pentane. 10.7 g of the product were obtained.

g) [5-Cyano-3-(2-ethoxy-phenyl)-2-oxo-2,3-dihydro-1H-indole-3-yl]-methyl acetate 10.7 g (26 mmol) of the intermediate product 192f were dissolved in 10 ml ethanol. 100 ml 2 M caustic soda solution was added, and the mixture was stirred at room temperature for 1 h. The reaction batch was mixed in by stirring to 1 M HCl, wherein a precipitate formed that was isolated and dried. This solid was transferred to a 1-l container and heated to 150° C., wherein this foamed as a result of a gas development. It was allowed to cool after the reaction had completed. The residue was treated with methanol and the precipitate obtained was isolated. 6.4 g of the product were obtained.

h) [5-Cyano-3-(2-ethoxy-phenyl)-2-oxo-2,3-dihydro-1H-indole-3-yl]-ethanoic acid 36 ml 2 M NaOH were added to 5.9 g (16.8 mmol) of the intermediate product 192 g in 25 ml ethanol, and everything was stirred at room temperature for 3 h. Then the reaction mixture was acidified with 6 ml ethanoic acid and diluted with water. A solid precipitated overnight, which was isolated and dried. 5.2 g of the product were obtained.

i) 3-(2-Ethoxy-phenyl)-2-oxo-3-{2-oxo-2-[4-(4-propyl-piperazine-1-yl)-piperidine-1-yl]-ethyl}-2,3-dihydro-1H-indole-5-carboxylic-acid nitrile 1.8 g (16.3 mmol) t-BuOK were carefully added to 1.9 g (5.4 mmol) of the intermediate product 192b in 25 ml water-free DMF at 0° C. Then 2 g (5.4 mmol) of the intermediate product 192 h, 0.8 g (5.4 mmol) HOBT, 2.9 ml (20.9 mmol)

Et₃N and finally, in portions, 1.1 g (5.4 mmol) EDAC were added, one after the other. The reaction mixture was then stirred at room temperature for 16 h. This mixture was then mixed by stirring into a 5% $K_2CO_3$ solution, wherein a precipitate formed that was isolated and dried. 2.6 g of the product were obtained.

j) 3-(2-Ethoxy-phenyl)-1-(4-methoxy-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile 47 mg (0.42 mmol) t-BuOK were added to 0.2 g (0.38 mmol) of the intermediate product 192i in 4 ml DMF at 0° C. Everything was stirred for 1 h at 0° C. Subsequently, 86 mg (0.42 mmol) 4-methoxybenzenesulfonylchloride were added in portions at 0° C. and everything was stirred for 16 h. The reaction batch was mixed in by stirring to 1 M NaOH and the resulting precipitate was isolated. This was then recrystallised from methanol, wherein 0.15 g of the product resulted.

$^1$H-NMR (CDCl₃): δ=0.9 (3H), 1.0-1.2 (1H), 1.2-1.3 (3H), 1.35 (1H), 1.45-1.75 (4H), 1.85 (1H), 2.25 (1H), 2.3-2.8 (10H), 2.9 (1H), 3.3 (1H), 3.65 (1H), 3.75-3.95 (5H), 4.0 (1H), 6.8 (1H), 6.9-7.0 (3H), 7.25 (2H), 7.35 (1H), 7.55 (1H) and 8.0-8.15 (3H) ppm.

Example 193

3-(2-Ethoxy-phenyl)-1-(2-fluoro-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile $^1$H-NMR (CDCl₃): δ=0.9 (3H), 1.15 (1H), 1.25-1.4 (4H), 1.4-1.75 (4H), 1.8 (1H), 2.1-2.8 (11H), 2.9 (1H), 3.3 (1H), 3.65 (1H), 3.8 (1H), 3.85 (1H), 3.95 (1H), 4.0-4.15 (2H), 6.8 (1H), 6.95 (1H), 7.15 (1H), 7.2-7.4 (3H), 7.6 (2H), 8.15 (1H) and 8.2 (1H) ppm.

Example 194

3-(2-Ethoxy-phenyl)-1-(2,4-dimethoxy-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile $^1$H-NMR (CDCl₃): δ=0.9 (3H), 1.2 (1H), 1.3-1.45 (4H), 1.45-1.9 (5H), 2.2-2.8 (11H), 2.9 (1H), 3.25 (1H), 3.55 (1H), 3.75-3.9 (5H), 3.95 (1H), 4.05 (1H), 4.15 (1H), 6.4 (1H), 6.55 (1H), 6.85 (1H), 6.9 (1H), 7.2 (1H), 7.25 (1H), 7.55 (2H) and 8.1 (2H) ppm.

Example 195

3-(2-Ethoxy-phenyl)-1-(2,4-difluoro-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile $^1$H-NMR (CDCl₃): δ=0.9 (3H), 1.15 (1H), 1.2-1.4 (4H), 1.4-1.75 (3H), 1.85 (1H), 2.15-2.7 (11H), 2.9 (1H), 3.3 (1H), 3.65 (1H), 3.75-4.0 (2H), 4.1 (1H), 6.8 (1H), 6.85 (1H), 6.9-7.0 (2H), 7.3 (3H), 7.6 (1H), 8.1 (1H) and 8.2 (1H) ppm.

Example 196

3-(2-Ethoxy-phenyl)-1-(4-chloro-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile $^1$H-NMR (CDCl₃): δ=0.9 (3H), 1.0 (1H), 1.15 (1H), 1.25-1.8 (4H), 1.85 (1H), 2.15-2.8 (11H), 2.95 (1H), 3.3 (1H), 3.6 (1H), 3.7-3.95 (3H), 4.0-4.15 (1H), 6.8 (1H), 6.95 (1H), 7.3 (3H), 7.45 (2H), 7.55 (1H) and 8.0-8.1 (3H) ppm.

Example 197

4-(4-Isopropyl-piperazine-1-yl)-piperidine-1-carboxylic acid-[5-cyano-1-benzenesulfonyl-3-(2-ethoxy-phenyl)-2-oxo-2,3-dihydro-1H-indole-3-yl] amide $^1$H-NMR (CDCl₃): δ=1.05 (6H), 1.3 (2H), 1.5 (3H), 1.75 (2H), 2.3 (1H), 2.5-2.8 (11H), 3.7 (2H), 4.1 (1H), 4.2 (1H), 6.45 (1H), 6.9 (2H), 7.05 (1H), 7.3 (1H), 7.5 (3H), 7.55-7.65 (2H), 8.05 (1H) and 8.15 (1H) ppm.

Example 198

4-(4-Isopropyl-piperazine-1-yl)-piperidine-1-carboxylic acid-[5-cyano-1-(2-methoxy-benzenesulfonyl)-3-(2-ethoxy-phenyl)-2-oxo-2,3-dihydro-1H-indole-3-yl] amide $^1$H-NMR (CDCl₃): δ=1.05 (6H), 1.35 (3H), 1.55 (3H), 1.75 (2H), 2.3 (1H), 2.45-2.8 (11H), 3.5 (1H), 3.75 (2H), 4.15 (1H), 4.25 (1H), 6.7 (1H), 6.85 (1H), 6.9 (2H), 6.95 (1H), 7.05 (1H), 7.25 (1H), 7.55 (1H), 7.6 (2H), 8.1 (1H) and 8.15 (1H) ppm.

Example 199

4-(4-isopropyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] amide $^1$H-NMR (CDCl₃): δ=1.05 (6H), 1.35 (3H), 1.5 (3H), 1.75 (2H), 2.3 (1H), 2.5-2.8 (11H), 3.7 (2H), 3.85 (3H), 4.0 (1H), 4.2 (1H), 6.5 (1H), 6.85-7.0 (4H), 7.05 (1H), 7.3 (1H), 7.5 (1H), 7.55 (1H) and 7.95-8.1 (3H) ppm.

Example 200

4-(4-Isopropyl-piperazine-1-yl)-piperidine-1-carboxylic acid-[5-cyano-1-(2-fluoro-benzenesulfonyl)-3-(2-ethoxy-phenyl)-2-oxo-2,3-dihydro-1H-indole-3-yl] amide $^1$H-NMR (CDCl₃): δ=1.05 (6H), 1.25 (1H), 1.35 (1H), 1.5 (3H), 1.75 (2H), 2.3 (1H), 2.45-2.8 (11H), 3.7 (2H), 4.1 (1H), 4.2 (1H), 6.45 (1H), 6.9 (2H), 7.1 (1H), 7.15 (1H), 7.3 (2H), 7.5 (1H), 7.6 (2H), 8.1 (1H) and 8.15 (1H) ppm.

Example 201

4-(4-Isopropyl-piperazine-1-yl)-piperidine-1-carboxylic acid-[5-cyano-1-(2,4-difluoro-benzenesulfonyl)-3-(2-ethoxy-phenyl)-2-oxo-2,3-dihydro-1H-indole-3-yl] amide $^1$H-NMR (D₆-DMSO): δ=1.05 (6H), 1.25 (1H), 1.35 (1H), 1.45 (3H), 1.75 (2H), 2.3 (1H), 2.5-2.8 (11H), 3.7 (2H), 4.1

(1H), 4.2 (1H), 6.4 (1H), 6.8-7.05 (4H), 7.15 (1H), 7.3 (1H), 7.5 (1H), 7.6 (1H), 8.1 (1H) and 8.2 (1H) ppm.

Example 202

4-(4-ethyl-piperazine-1-yl)-piperidine-1-carboxylic acid-[5-cyano-1-(4-methoxy-benzenesulfonyl)-3-(2-ethoxy-phenyl)-2-oxo-2,3-dihydro-1H-indole-3-yl] amide $^1$H-NMR (D$_6$-DMSO): δ=0.95 (3H), 1.1 (3H), 1.15 (2H), 1.6 (2H), 2.2-2.7 (12H), 3.75 (2H), 3.85 (3H), 3.9 (2H), 6.9-7.0 (2H), 7.1 (2H), 7.3 (1H), 7.5 (1H), 7.55 (1H), 7.6 (1H), 7.8 (1H), 7.85 (1H) and 7.95 (2H) ppm.

Example 203

4-(4-Ethyl-piperazine-1-yl)-piperidine-1-carboxylic acid-[5-cyano-1-(2,4-difluoro-benzenesulfonyl)-3-(2-ethoxy-phenyl)-2-oxo-2,3-dihydro-1H-indole-3-yl] amide $^1$H-NMR (CDCl$_3$): δ=1.1 (3H), 1.25 (1H), 1.35 (1H), 1.45 (3H), 1.75 (2H), 2.25-2.8 (12H), 3.7 (2H), 4.1 (1H), 4.2 (1H), 6.4 (1H), 6.8-7.05 (4H), 7.15 (1H), 7.35 (1H), 7.5 (1H), 7.6 (1H), 8.1 (1H) and 8.2 (1H) ppm.

Example 204

4-(4-Ethyl-piperazine-1-yl)-piperidine-1-carboxylic acid-[5-cyano-1-(4-fluoro-benzenesulfonyl)-3-(2-ethoxy-phenyl)-2-oxo-2,3-dihydro-1H-indole-3-yl] amide $^1$H-NMR (CDCl$_3$): δ=1.1 (3H), 1.3 (2H), 1.5 (3H), 1.8 (2H), 2.2-2.8 (13H), 3.7 (2H), 4.1 (1H), 4.2 (1H), 6.4 (1H), 6.9 (2H), 7.05-7.25 (3H), 7.3 (1H), 7.45 (1H), 7.6 (1H), 8.05 (1H) and 8.15 (2H) ppm.

Example 205

4-(4-Propyl-piperazine-1-yl)-piperidine-1-carboxylic acid-[5-cyano-1-(4-fluoro-benzenesulfonyl)-3-(2-ethoxy-phenyl)-2-oxo-2,3-dihydro-1H-indole-3-yl] amide $^1$H-NMR (CDCl$_3$): δ=0.9 (3H), 1.3 (2H), 1.4-1.6 (5H), 1.75 (2H), 2.2-2.8 (13H), 3.7 (2H), 4.1 (1H), 4.2 (1H), 6.4 (1H), 6.9 (2H), 7.05-7.2 (3H), 7.3 (1H), 7.45 (1H), 7.6 (1H), 8.0 (1H) and 8.15 (2H) ppm.

Example 206

4-(1-Methyl-piperidine-4-yl)-piperazine-1-carboxylic acid-[1 (4-methoxy-1-benzenesulfonyl)-5-cyano-2-oxo-3-(2-ethoxyphenyl)-2,3-dihydro-1H-indole-3-yl] ester $^1$H-NMR (CDCl$_3$): δ=1.25 (3H), 1.6-1.9 (4H), 2.1 (2H), 2.25-2.45 (4H), 2.5 (1H), 2.6 (1H), 2.9-3.2 (4H), 3.6 (2H), 3.8 (1H), 3.85 (3H), 4.0 (1H), 6.8 (1H), 6.95 (2H), 7.05 (1H), 7.25 (1H), 7.35 (1H), 7.65 (1H), 7.7 (1H) and 8.05 (2H) ppm.

Example 207

4-(4-Isopropyl-piperazine-1-yl)-piperidine-1-carboxylic acid-[5-cyano-1-(4-fluoro-benzenesulfonyl)-3-(2-ethoxy-phenyl)-2-oxo-2,3-dihydro-1H-indole-3-yl] amide $^1$H-NMR (D$_6$-DMSO): δ=1.05 (6H), 1.35 (2H), 1.5 (3H), 1.75 (2H), 2.3 (1H), 2.5-2.8 (11H), 3.7 (2H), 4.1 (1H), 4.2 (1H), 6.45 (1H), 6.9 (2H), 7.1-7.25 (3H), 7.3 (1H), 7.45 (1H), 7.6 (1H), 8.05 (1H) and 8.15 (2H) ppm.

Example 208

3-(2-Ethoxy-phenyl)-1-(4-fluoro-benzenesulfonyl)-2-oxo-3-{2-oxo-2-[4-(4-propyl-piperazine-1-yl)-piperidine-1-yl]-ethyl}-2,3-dihydro-1H-indole-5-carboxylic-acid nitrile $^1$H-NMR (CDCl$_3$): δ=0.9 (3H), 1.1 (1H), 1.15 (1H), 1.25-1.4 (4H), 1.45-1.6 (2H), 1.7 (1H), 1.85 (1H), 2.15-2.7 (12H), 2.95 (1H), 3.3 (1H), 3.65 (1H), 3.75-3.95 (3H), 4.05 (1H), 6.8 (1H), 6.95 (1H), 7.15 (2H), 7.25-7.4 (3H), 7.55 (1H), 8.05 (1H) and 8.15 (2H) ppm.

The invention claimed is:

1. A compound of the general formula (I),

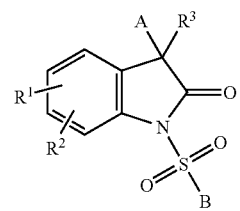

wherein

A is $C_{6-10}$-aryl, which can be substituted with a maximum of four residues $R^4$ that are selected independently of one another from the group consisting of hydrogen, chlorine, bromine, iodine, fluorine, $(CH_2)_{0-2}$—CN, CF$_3$, OCF$_3$, CONH$_2$, CONH(C$_1$-C$_4$ alkyl), CON(C$_1$-C$_4$ alkyl)(C$_1$-C$_4$ alkyl), NHCHO, NHCONH$_2$, N(C$_0$-C$_4$ alkylene)CONH$_2$, N(C$_0$-C$_4$ alkylene)CONH(C$_1$-C$_4$ alkyl), NHCOCH$_3$, NO$_2$, $(CH_2)_{0-2}$—OH, O—C$_1$-C$_6$ alkyl, $(CH_2)_{0-2}$—O—C$_1$-C$_4$ alkyl, O—C$_0$-C$_4$ alkylene-phenyl, phenyl, C$_1$-C$_6$ alkyl, C$_2$-C$_6$ alkenyl and C$_2$-C$_6$ alkynyl, B is an aromatic or partially aromatic monocyclic or bicyclic $C_{6-10}$, that can be substituted with the residues $R^6$, $R^7$, $R^8$ and/or $R^9$, wherein $R^6$, $R^7$, $R^8$ and $R^9$ are selected independently of one another from the group consisting of hydrogen, chlorine, bromine, iodine, fluorine, $(CH_2)_{0-2}$—CN, CF$_3$, OCF$_3$, CONH$_2$, CONH(C$_1$-C$_4$ alkyl), CON(C$_1$-C$_4$ alkyl)(C$_1$-C$_4$ alkyl), NHCHO, N(C$_{0-4}$ alkylene)CONH(C$_1$-C$_4$ NHCOCH$_3$, NO$_2$, OH, O—C$_1$-C$_4$ alkyl, $(CH_2)_{0-2}$—O—(CH$_2$)$_0$-3-CH$_3$, O-alkylene-phenyl, phenyl, C$_1$-C$_6$ alkyl, C$_2$-C$_6$ alkenyl and C$_2$-C$_6$ alkynyl, R¹ is hydrogen, $C_1$-$C_6$ alkyl, OH, O—($C_1$-$C_4$ alkyl), N($C_1$-$C_4$ alkyl)($C_1$-$C_4$ alkyl), CN, CONH$_2$, OCF$_3$, CF$_3$, Br, F, Cl, J, NO$_2$, NHCHO, NHCO($C_1$-$C_4$ alkyl) or NHCONH$_2$, R² is hydrogen, $C_1$-$C_4$ alkyl, O—($C_1$-$C_4$ alkyl), Cl or F, R³ is a residue (W)—(X)—(Y)—Z, wherein W is $C_1$-$C_4$ alkylene, ($C_0$-$C_4$ alkylene)-O—($C_0$-$C_4$ alkylene) or ($C_0$-$C_4$ alkylene)-NR¹⁵—($C_0$-$C_4$ alkylene), wherein R¹⁵ is hydrogen or $C_1$-$C_4$ alkyl, X is CO, SO$_2$, (C=NH) or (C=N—CN): and Y is a residue selected from the group consisting of

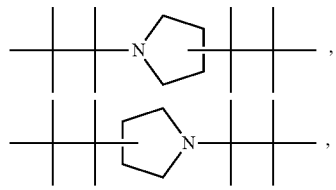

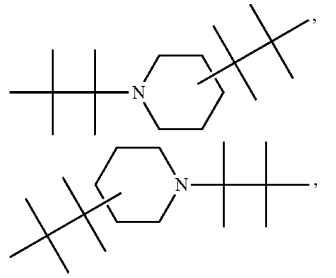

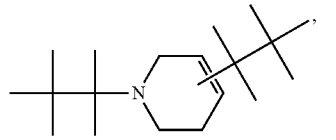

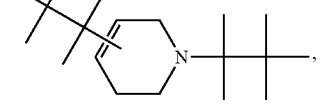

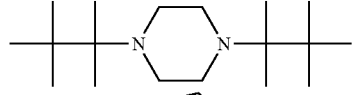

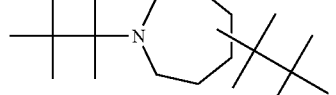

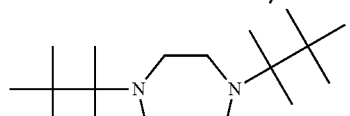

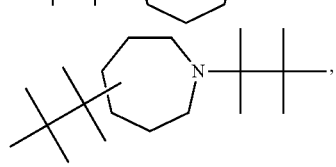

and wherein Y can additionally be substituted with R¹⁰ and/or R¹¹, wherein

R¹⁰ is hydrogen, $C_1$-$C_6$ alkyl, $C_2$-$C_6$ alkenyl, $C_2$-$C_6$ alkynyl, OH, O—$C_1$-$C_4$ alkyl, O—$C_1$-$C_4$ alkylene-phenyl, NH$_2$, NH($C_1$-$C_4$ alkyl) or N($C_1$-$C_4$ alkyl)($C_1$-$C_4$ alkyl), R¹¹ is hydrogen, $C_1$-$C_6$ alkyl, $C_2$-$C_6$ alkenyl, $C_2$-$C_6$ alkynyl, OH, O—$C_1$-$C_4$ alkyl, O—$C_0$-$C_4$ alkylene-phenyl, NH$_2$, NH($C_1$-$C_4$ alkyl) or N($C_1$-$C_4$ alkyl)($C_1$-$C_4$ alkyl), and Z is a residue selected from the group consisting of

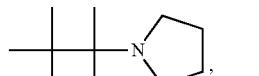

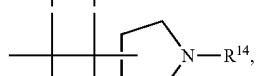

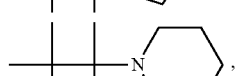

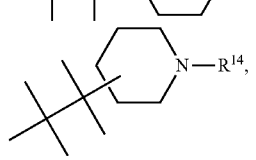

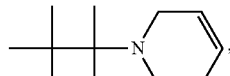

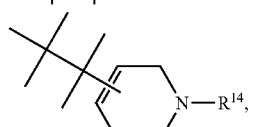

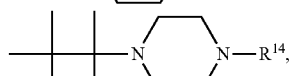

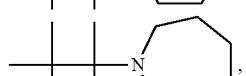

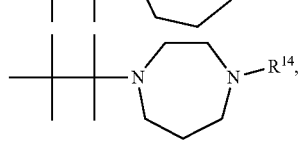

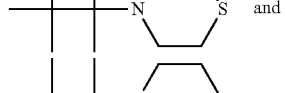 and

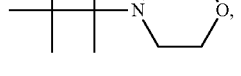

wherein Z can additionally be substituted with R¹² and/or R¹³, wherein

R¹² is hydrogen, $C_1$-$C_6$ alkyl, $C_2$-$C_6$ alkenyl, $C_2$-$C_6$ alkynyl, OH, O—$C_1$-$C_4$ alkyl, O—$C_0$-$C_4$ alkylene-phenyl, NH$_2$, NH($C_1$-$C_4$ alkyl) or N($C_1$-$C_4$ alkyl)($C_1$-$C_4$ alkyl), R¹³ is hydrogen, $C_1$-$C_6$ alkyl, $C_2$-$C_6$ alkenyl, $C_2$-$C_6$ alkynyl, OH, O($C_1$-$C_4$ alkyl), O—$C_0$-$C_4$ alkylene-phenyl, NH$_2$, NH($C_1$-$C_4$ alkyl) or N($C_1$-$C_4$ alkyl)($C_1$-$C_4$ alkyl), $R^{14}$ is hydrogen, $C_1$-$C_6$ alkyl, $C_2$-$C_6$ alkenyl, $C_2$-$C_6$ alkynyl or $C_0$-$C_4$ alkylene-phenyl, and their tautomeric, enantiomeric and/or diastereomeric forms, as well as the physiologically compatible saltsthereof.

2. The compound of claim 1, wherein A is a phenyl ring that can be substituted with a maximum of four residues $R^4$ and B is a phenyl ring that can be substituted with the residues $R^6$, $R^7$, $R^8$ and/or $R^9$, wherein the residues $R^4$, $R^6$, $R^7$, $R^8$ and $R^9$ shall have the meanings cited in claim 1, and their tautomeric, enantiomeric and/or diastereomeric forms, as well as the physiologically compatible saltsthereof.

3. The compound of claim 1, wherein

A is a phenyl ring that can be substituted with a maximum of two residues $R^4$ that are selected independently of one another from the group consisting of hydrogen, chlorine, O—$C_1$-$C^4$ alkyl, $(CH_2)_{0-2}$—O—$(CH_2)_{0-2}$—CH, ad $C_1$-$C_6$ alkyl, B is a phenyl ring that can be substituted with the residues $R^6$, $R^7$, $R^8$ and/or $R^9$, wherein $R^6$, $R^7$, $R^8$ and $R^9$ are selected independently of one another from the group consisting of hydrogen, fluorine, chlorine, O—$C_1$-$C_4$ alkyl, $(CH_2)_{0-2}$—O—$(CH_2)_{0-2}$—$CH_3$ and $C_1$-$C_6$ alkyl, $R^1$ is hydrogen, CN, F, Cl, $C_{1-4}$ alkyl, OH or O—$(C_{1-4}$ alkyl), $R^2$ is hydrogen, $R^3$ is a residue (W)—(X)—(Y)—Z, wherein W is O, $CH_2NH$, $NHCH_2$, $OCH_1$, $CH_2O$ or NH, X is CO, Y is a residue selected from the group consisting of

[structures], and

Z is a residue selected from the group consisting of

[structures]

wherein Z can additionally be substituted with $R^{12}$ and/or $R^{13}$, wherein $R^{12}$ is hydrogen or $C_1$-$C_4$ alkyl, $R^{13}$ is hydrogen or $C_1$-$C_4$ alkyl and wherein $R^{14}$ is hydrogen, $C_1$-$C_4$ alkyl, $C_2$-$C_4$ alkenyl or $C_2$-$C_4$ alkynyl, and their tautomeric, enantiomeric and/or diastereomeric forms, as well as the physiologically compatible saltsthereof.

4. The compound of claim 1, wherein

A is a phenyl ring that can be substituted with a maximum of two residues $R^4$ that are selected independently of one another from the group consisting of hydrogen, chlorine, O—$C_1$-$C_4$ alkyl, $(CH_2)_{0-2}$—O—$(CH_2)_{0-2}$—$CH_3$ and $C_1$-$C_6$ alkyl, B is a phenyl ring that can be substituted with the residues $R^6$ and/or $R^7$ wherein $R^6$ and $R^7$ are selected independently of one another from the group consisting of hydrogen, fluorine, chlorine, O—$C_1$-$C_4$ alkyl and $C_1$-$C_6$ alkyl, $R^1$ is hydrogen, F, Cl, $CH_3$, CN, $CH_2CH_3$, $OCH_3$ or $OCH_2CH_3$, $R^2$ is hydrogen, $R^3$ is a residue (W)—(X)—(Y)—Z, wherein W is O, $CH_2$, or NH, X is CO, Y is a residue selected from the group

[structure]

-continued

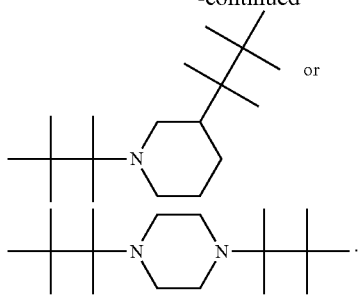

or

Z is a residue selected from the group

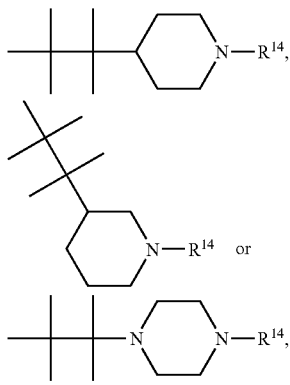

wherein Z can be substituted with $R^{12}$ and/or $R^{13}$, wherein
$R^{12}$ is hydrogen or $C_1$-$C_4$ alkyl,
$R^{13}$ is hydrogen or $C_1$-$C_4$ alkyl and
$R^{14}$ is hydrogen, $C_1$-$C_4$ alkyl, $C_2$-$C_4$ alkenyl or $C_2$-$C_4$ alkynyl,
and their tautomeric, enantiomeric and/or diastereomeric forms, as well as the physiologically compatible saltsthereof.

5. The compound of claim 1, wherein
A is a phenyl ring that can be substituted with a maximum of two residues $R^4$ that are selected independently of one another from the group consisting of hydrogen, chlorine, O—$C_1$-$C_4$ alkyl, $(CH_2)_{0-2}$—O—$(CH_2)_{0-2}$—$CH_3$, and $C_1$-$C_6$ alkyl,
B is a phenyl ring that can be substituted with the residues $R^6$ and/or $R^7$, wherein $R^6$ and $R^7$ are selected independently of one another from the group consisting of hydrogen, fluorine, chlorine, O—$C_1$-$C_4$ alkyl, and $C_1$-$C_6$ alkyl,
$R^1$ is Cl, $CH_3$, CN, $CH_2CH_3$ or $OCH_3$,
$R^2$ is hydrogen,
$R^3$ is a residue (W)—(X)—(Y)—Z, wherein
W is $CH_2$, —O or NH,
X is CO,
Y is a residue

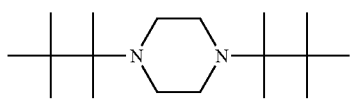

Z is a residue

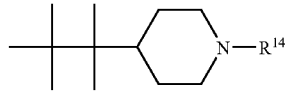

wherein
$R^{14}$ is hydrogen, $C_1$-$C_4$ alkyl, $C_2$-$C_4$ alkenyl or $C_2$-$C_4$ alkynyl,
and their tautomeric, enantiomeric and/or diastereomeric forms, as well as the physiologically compatible saltsthereof.

6. The compound of claim 1, wherein
A is a phenyl ring that can be substituted with a maximum of two residues $R^4$ that are selected independently of one another from the group consisting of hydrogen, chlorine, O—$C_1$-$C_4$ alkyl and $C_1$-$C_4$ alkyl,
B is a phenyl ring that is substituted with the residues $R^6$ and/or $R^7$, wherein $R^6$ and $R^7$ are selected independently of one another from the group consisting of hydrogen, fluorine, chlorine, O—$C_1$-$C_4$ alkyl, and $C_1$-$C_6$ alkyl,
$R^1$ is hydrogen, Cl, $CH_3$, CN, $CH_2CH_3$, OCH, or $OCH_2CH_3$,
$R^2$ is hydrogen,
$R^3$ is a residue (W)—(X)—(Y)—Z, wherein
W is $CH_2$, O or NH,
X is CO,
Y is a residue

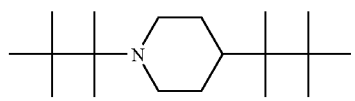

and
Z is a residue

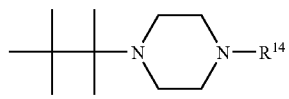

wherein $R^{14}$ is hydrogen, $C_1$-$C_4$ alkyl, $C_2$-$C_4$ alkenyl or $C_1$-$C_4$ alkynyl,
and their tautomeric, enantiomeric and/or diastereomeric forms, as well as the physiologically compatible saltsthereof.

7. A method for treating a disease selected from the group consisting of hypertension, pulmonary hypertension, cardiac insufficiency, myocardial infarction, coronary spasm, unstable angina, PTCA (percutaneous transluminal coronary angioplasty), and ischemia of the heart, the method comprising administering the compound of claim 1 to a subject in need thereof.

* * * * *